(12) United States Patent
Piehl et al.

(10) Patent No.: US 11,957,886 B2
(45) Date of Patent: Apr. 16, 2024

(54) RAPID FLUID DELIVERY SYSTEM

(71) Applicant: 410 Medical, Inc., Durham, NC (US)

(72) Inventors: Mark D. Piehl, Chapel Hill, NC (US); Galen C. Robertson, Apex, NC (US); John Tyler Willis Hagler, Chapel Hill, NC (US); Robert W. Titkemeyer, Wimberley, TX (US); Frederic C. Feiler, Jr., Wilmington, NC (US)

(73) Assignee: 410 Medical, Inc., Research Triangle Park, NC (US)

( * ) Notice: Subject to any disclaimer, the term of this patent is extended or adjusted under 35 U.S.C. 154(b) by 0 days.

(21) Appl. No.: 17/959,194

(22) Filed: Oct. 3, 2022

(65) Prior Publication Data

US 2023/0144057 A1 May 11, 2023

Related U.S. Application Data

(63) Continuation of application No. 16/548,490, filed on Aug. 22, 2019, now Pat. No. 11,458,256, which is a
(Continued)

(51) Int. Cl.
*A61M 5/142* (2006.01)
*A61M 5/00* (2006.01)
(Continued)

(52) U.S. Cl.
CPC ........ *A61M 5/31581* (2013.01); *A61M 5/002* (2013.01); *A61M 5/007* (2013.01);
(Continued)

(58) Field of Classification Search
CPC .............. A61M 5/1782; A61M 5/1413; A61M 5/1456; A61M 5/204; A61M 2005/3114; A61D 1/025; A61D 7/00
See application file for complete search history.

(56) References Cited

U.S. PATENT DOCUMENTS 4,065,230 A 12/1977 Gezari
4,202,333 A * 5/1980 Thill .................... A61M 5/1454
604/135
(Continued)

FOREIGN PATENT DOCUMENTS

DE 10326306 A1 12/2004
EP 3854432 A1 7/2021
(Continued)

OTHER PUBLICATIONS

Machine Translation of FR 2690839 A1 created Feb. 7, 2023. (Year: 1993).*
(Continued)

*Primary Examiner* — Laura A Bouchelle

(57) ABSTRACT

A system includes a tubing set and a drive assembly. The tubing set includes inlet tubing couplable to a source of fluid, a valve coupled to the inlet tubing, a syringe coupled to the inlet tubing via the valve, and outlet tubing coupled to the valve. The valve is configured to allow fluid to be drawn from the source of fluid via the inlet tubing into a syringe body of the syringe and to be expelled from the syringe body and through the outlet tubing, and to prevent fluid from being drawn from the outlet tubing into the syringe body and to prevent fluid expelled from the syringe body from flowing through the inlet tubing. The drive assembly is configured to reversibly receive the tubing set such that a drive mechanism is engaged with a plunger of the syringe to reciprocally translate the plunger relative to the syringe body.

20 Claims, 48 Drawing Sheets

Related U.S. Application Data continuation of application No. 15/612,668, filed on Jun. 2, 2017, now Pat. No. 10,391,257, which is a continuation of application No. PCT/US2016/019167, filed on Feb. 23, 2016.

(60) Provisional application No. 62/274,566, filed on Jan. 4, 2016, provisional application No. 62/187,367, filed on Jul. 1, 2015, provisional application No. 62/120,021, filed on Feb. 24, 2015.

(51) Int. Cl.

| | | |
|---|---|---|
| *A61M 5/14* | (2006.01) | |
| *A61M 5/145* | (2006.01) | |
| *A61M 5/178* | (2006.01) | |
| *A61M 5/19* | (2006.01) | |
| *A61M 5/20* | (2006.01) | |
| *A61M 5/31* | (2006.01) | |
| *A61M 5/315* | (2006.01) | |
| *A61M 5/48* | (2006.01) | |
| *A61M 39/10* | (2006.01) | |
| *A61M 39/24* | (2006.01) | |
| *A61M 39/28* | (2006.01) | |

(52) U.S. Cl.
CPC ...... *A61M 5/1413* (2013.01); *A61M 5/14244* (2013.01); *A61M 5/1456* (2013.01); *A61M 5/1782* (2013.01); *A61M 5/19* (2013.01); *A61M 5/2033* (2013.01); *A61M 5/3146* (2013.01); *A61M 5/3158* (2013.01); *A61M 5/31586* (2013.01); *A61M 5/486* (2013.01); *A61M 5/488* (2013.01); *A61M 39/10* (2013.01); *A61M 39/105* (2013.01); *A61M 39/24* (2013.01); *A61M 39/28* (2013.01); *A61M 2005/202* (2013.01); *A61M 2005/2026* (2013.01); *A61M 2005/2073* (2013.01); *A61M 2005/3128* (2013.01); *A61M 2005/31588* (2013.01); *A61M 2039/2493* (2013.01); *A61M 2205/332* (2013.01); *A61M 2205/3331* (2013.01); *A61M 2205/3379* (2013.01); *A61M 2205/3584* (2013.01); *A61M 2205/50* (2013.01)

(56) References Cited

U.S. PATENT DOCUMENTS

| | | |
|---|---|---|
| 4,569,662 A | 2/1986 | Dragan |
| 4,594,073 A | 6/1986 | Stine |
| 4,687,472 A | 8/1987 | Gross |
| 4,758,233 A | 7/1988 | Phillips et al. |
| 4,808,077 A | 2/1989 | Kan et al. |
| 4,896,678 A | 1/1990 | Ogawa |
| 4,919,649 A | 4/1990 | Timothy et al. |
| 4,968,303 A | 11/1990 | Clarke et al. |
| 5,139,488 A | 8/1992 | Klein |
| 5,141,504 A | 8/1992 | Herweck et al. |
| 5,203,839 A | 4/1993 | Skaggs |
| 5,304,147 A | 4/1994 | Johnson et al. |
| 5,389,070 A | 2/1995 | Morell |
| 5,395,375 A | 3/1995 | Turkel et al. |
| 5,733,258 A | 3/1998 | Lane |
| 5,807,340 A * | 9/1998 | Pokras ............... A61M 5/204 604/209 |
| 5,865,805 A | 2/1999 | Ziemba |
| 5,913,874 A | 6/1999 | Berns et al. |
| 5,924,206 A | 7/1999 | Cote et al. |
| 6,068,624 A | 5/2000 | Benecke et al. |
| 6,117,158 A | 9/2000 | Measamer et al. |
| 6,142,974 A | 11/2000 | Kistner et al. |
| 6,213,984 B1 | 4/2001 | Lane et al. |
| 6,257,265 B1 | 7/2001 | Brunner et al. |
| 6,260,737 B1 | 7/2001 | Gruendeman |
| 6,439,439 B1 | 8/2002 | Rickard et al. |
| 6,475,193 B1 | 11/2002 | Park |
| 6,585,696 B2 | 7/2003 | Petersen et al. |
| 6,716,195 B2 | 4/2004 | Nolan, Jr. et al. |
| 6,802,824 B2 | 10/2004 | Mickley et al. |
| 6,989,000 B2 | 1/2006 | Schreijag et al. |
| 7,041,084 B2 | 5/2006 | Fojtik |
| 7,160,087 B2 | 1/2007 | Fathallah et al. |
| 7,553,294 B2 | 6/2009 | Lazzaro et al. |
| 7,570,314 B2 | 8/2009 | Lee |
| 7,637,279 B2 | 12/2009 | Amley et al. |
| 7,691,085 B2 | 4/2010 | Dedig et al. |
| 7,833,204 B2 | 11/2010 | Picha |
| 7,846,130 B2 | 12/2010 | Elazari-Volcani et al. |
| 7,951,112 B2 | 5/2011 | Patzer |
| 7,988,677 B2 | 8/2011 | Fojtik |
| 8,047,407 B2 | 11/2011 | Wheeler et al. |
| 8,066,629 B2 | 11/2011 | Dlugos |
| 8,133,203 B2 | 3/2012 | Hack |
| 8,142,365 B2 | 3/2012 | Miller |
| 8,357,147 B2 | 1/2013 | Burkinshaw et al. |
| D679,011 S | 3/2013 | Kitayama et al. |
| 8,415,407 B2 | 4/2013 | Beyar et al. |
| 8,486,155 B2 | 7/2013 | McAlister et al. |
| D687,549 S | 8/2013 | Johnson et al. |
| 8,539,644 B2 | 9/2013 | Fojtik |
| 8,574,200 B2 | 11/2013 | Hack |
| 8,631,935 B2 | 1/2014 | Tomes et al. |
| 8,672,900 B2 | 3/2014 | Fojtik |
| 8,746,452 B2 | 6/2014 | Tomes et al. |
| 8,747,356 B2 | 6/2014 | Cocker et al. |
| 9,057,363 B2 | 6/2015 | Capone et al. |
| 9,107,986 B2 | 8/2015 | Bonnette et al. |
| D744,099 S | 11/2015 | Osada |
| 9,192,711 B2 | 11/2015 | Barnes |
| 9,220,835 B2 | 12/2015 | Cane' |
| D750,244 S | 2/2016 | Osada |
| 9,267,498 B2 | 2/2016 | Kolln |
| 9,283,352 B2 | 3/2016 | Tomes et al. |
| 9,295,778 B2 * | 3/2016 | Kamen ............... G16H 20/17 |
| 9,522,753 B2 | 12/2016 | Tomes et al. |
| 10,004,846 B2 | 6/2018 | Bonnette et al. |
| 10,016,564 B2 | 7/2018 | Piehl et al. |
| 10,322,227 B2 | 6/2019 | Piehl et al. |
| 10,391,257 B2 | 8/2019 | Piehl et al. |
| 10,661,029 B2 | 5/2020 | Robertson et al. |
| 10,780,258 B2 | 9/2020 | Pettini et al. |
| 11,458,256 B2 | 10/2022 | Piehl et al. |
| 2002/0116021 A1 | 8/2002 | Gordon |
| 2004/0039344 A1 | 2/2004 | Baldwin et al. |
| 2004/0116873 A1 | 6/2004 | Fojtik |
| 2004/0133152 A1 | 7/2004 | Reilly et al. |
| 2004/0138677 A1 | 7/2004 | Little et al. |
| 2005/0137575 A1 | 6/2005 | Thompson et al. |
| 2005/0148934 A1 | 7/2005 | Martens et al. |
| 2005/0215976 A1 | 9/2005 | Wallen |
| 2005/0261633 A1 | 11/2005 | Khalaj |
| 2005/0261693 A1 | 11/2005 | Miller et al. |
| 2006/0184124 A1 | 8/2006 | Cowan et al. |
| 2006/0206144 A1 | 9/2006 | Miersch |
| 2006/0247578 A1 | 11/2006 | Arguedas et al. |
| 2006/0293560 A1 | 12/2006 | Nguyen et al. |
| 2007/0235083 A1 | 10/2007 | Dlugos |
| 2008/0083813 A1 | 4/2008 | Zemlok et al. |
| 2008/0098564 A1 | 5/2008 | Fojtik |
| 2008/0132850 A1 | 6/2008 | Fumiyama et al. |
| 2008/0269671 A1 | 10/2008 | Lin et al. |
| 2008/0287872 A1 | 11/2008 | Patzer |
| 2008/0287910 A1 | 11/2008 | Picha |
| 2009/0088702 A1 | 4/2009 | Fojtik |
| 2009/0112164 A1 | 4/2009 | Reilly et al. |
| 2010/0204649 A1 | 8/2010 | Miller et al. |
| 2010/0217122 A1 | 8/2010 | Fumiyama et al. |
| 2010/0249719 A1 | 9/2010 | Fojtik |
| 2010/0264194 A1 | 10/2010 | Huang et al. |
| 2011/0208158 A1 | 8/2011 | Sigmon, Jr. et al. |
| 2011/0282197 A1 | 11/2011 | Martz |

(56) References Cited

U.S. PATENT DOCUMENTS

| | | | |
|---|---|---|---|
| 2011/0282324 A1 | 11/2011 | Kurokawa et al. | |
| 2011/0282382 A1 | 11/2011 | McAlister et al. | |
| 2011/0313351 A1 | 12/2011 | Kamen et al. | |
| 2013/0237955 A1 | 9/2013 | Neta et al. | |
| 2013/0345644 A1 | 12/2013 | Fojtik | |
| 2014/0291355 A1 | 10/2014 | Fago | |
| 2014/0316369 A1 | 10/2014 | Centeno et al. | |
| 2014/0323984 A1 | 10/2014 | Bruce et al. | |
| 2015/0025500 A1 | 1/2015 | Piehl et al. | |
| 2015/0209821 A1 | 7/2015 | Pfahnl et al. | |
| 2015/0335530 A1 | 11/2015 | Aguerre et al. | |
| 2016/0166761 A1 * | 6/2016 | Piehl | A61B 17/3498 |
| | | | 604/207 |
| 2017/0021951 A1 | 1/2017 | Teague | |
| 2017/0281875 A1 | 10/2017 | Piehl et al. | |
| 2017/0319783 A1 | 11/2017 | Piehl et al. | |
| 2018/0295762 P1 | 10/2018 | Shaw et al. | |
| 2018/0296752 A1 | 10/2018 | Bonnette et al. | |
| 2019/0365567 A1 | 12/2019 | Balkenbush et al. | |
| 2019/0374724 A1 | 12/2019 | Piehl et al. | |
| 2020/0282135 A1 | 9/2020 | Breitweiser et al. | |
| 2022/0313901 A1 | 10/2022 | Lane et al. | |

FOREIGN PATENT DOCUMENTS

| | | | | |
|---|---|---|---|---|
| FR | 2690839 A1 * | 11/1993 | | A61D 1/025 |
| GB | 2233234 A * | 1/1991 | | A61D 1/025 |
| JP | H06503271 A | 4/1994 | | |
| JP | 2001521417 A | 11/2001 | | |
| JP | 2004527333 A | 9/2004 | | |
| JP | 2013507191 A | 3/2013 | | |
| NL | 8006197 A | 6/1982 | | |
| WO | WO-9306940 A1 | 4/1993 | | |
| WO | WO-9843690 A1 | 10/1998 | | |
| WO | WO-9917833 A1 | 4/1999 | | |
| WO | WO-02094343 A2 | 11/2002 | | |
| WO | WO-2008024814 A2 | 2/2008 | | |
| WO | WO-2010048753 A1 | 5/2010 | | |
| WO | WO-2011044343 A2 | 4/2011 | | |
| WO | WO-2012058070 A2 | 5/2012 | | |
| WO | WO-2014074807 A1 | 5/2014 | | |
| WO | WO-2014145354 A1 | 9/2014 | | |
| WO | WO-2016138018 A2 | 9/2016 | | |
| WO | WO-2022192285 A1 | 9/2022 | | |

OTHER PUBLICATIONS

Notice of Allowance for U.S. Appl. No. 17/845,560 dated May 30, 2023, 9 pages.
Examination Report, dated Apr. 28, 2022, for Canadian Patent Application No. 2,977,652 (4 total pages).
Examination Report, dated Nov. 14, 2019, for European Patent Application No. 16708327.8 (4 total pages).
Examination Report No. 1 dated Nov. 6, 2019, for Australian Application No. 2016222871, 3 pages.
Final Office Action, dated Jul. 18, 2018, for U.S. Appl. No. 15/612,668 (24 pages).
Final Office Action issued by The United States Patent and Trademark Office for U.S. Appl. No. 14/214,977, dated Aug. 31, 2017, 51 pages.
Final Office Action issued by The United States Patent and Trademark Office for U.S. Appl. No. 14/214,977, dated Dec. 18, 2015, 30 pages.
Final Office Action issued by The United States Patent and Trademark Office for U.S. Appl. No. 15/051,456, dated Sep. 27, 2018, 27 pages.
Final Office Action, dated Oct. 8, 2021, for U.S. Appl. No. 16/548,490 (33 total pages).
International Preliminary Report on Patentability issued by the International Searching Authority for Application No. PCT/US2014/030097, dated Sep. 15, 2015, 9 pages.
International Preliminary Report on Patentability, dated Sep. 8, 2017, corresponding to International Patent Application No. PCT/US2016/019167 (9 pages).
International Search Report and the Written Opinion of the International Searching Authority, dated Aug. 26, 2016, corresponding to International Patent Application No. PCT/US2016/019167 (13 pages).
International Search Report and Written Opinion for Application No. PCT/US2022/019381, dated Jul. 26, 2022, 10 pages.
International Search Report and Written Opinion issued by the International Searching Authority for Application No. PCT/US2014/030097, dated Aug. 6, 2014, 12 pages.
Invitation to Pay Additional Fees and, Where Applicable, Protest Fee, dated Jun. 22, 2016, for International Application No. PCT/US2016/019167 (6 total pages).
Invitation to Pay Fee for International Application No. PCT/US2022/019381 dated May 26, 2022, 2 pages.
MULTI-AD® Transfer Set (MAT4100), Braun, product description, http://us.bbraunoem.com/cgs/rde/xchg/oem-bbraunoem-en-us . . . , date unknown but believed to be before the priority date of the present application, printed from the internet Sep. 21, 2015, 1 page.
Non-Final Office Action for U.S. Appl. No. 17/845,560, dated Nov. 7, 2022, 15 pages.
Non-Final Office Action, dated Dec. 16, 2016, for U.S. Appl. No. 14/214,977 (55 total pages).
Non-Final Office Action, dated Jan. 14, 2021, for U.S. Appl. No. 16/548,490 (33 total pages).
Non-Final Office Action issued by The United States Patent and Trademark Office for U.S. Appl. No. 14/214,977, dated Jul. 13, 2015, 27 pages.
Non-Final Office Action issued by The United States Patent and Trademark Office for U.S. Appl. No. 14/214,977, dated Jun. 10, 2016, 42 pages.
Non-Final Office Action issued by The United States Patent and Trademark Office for U.S. Appl. No. 15/051,456, dated Dec. 26, 2017, 50 pages.
Non-Final Office Action issued by The United States Patent and Trademark Office for U.S. Appl. No. 15/612,668, dated Feb. 15, 2018, 75 pages.
Non-Final Office Action issued by The United States Patent and Trademark Office for U.S. Appl. No. 15/612,668, dated Feb. 7, 2019, 24 pages.
Non-Final Office Action issued by The United States Patent and Trademark Office for U.S. Appl. No. 15/612,668, dated Oct. 18, 2017, 26 pages.
Non-Final Office Action issued by The United States Patent and Trademark Office for U.S. Appl. No. 15/612,709, dated Sep. 18, 2017, 39 pages.
Notice of Allowance, dated May 31, 2022, for U.S. Appl. No. 16/548,490 (12 total pages).
Notice of Allowance issued by the United States Patent and Trademark Office for U.S. Appl. No. 15/051,456, dated Feb. 21, 2019, 11 pages.
Notice of Allowance issued by the United States Patent and Trademark office for U.S. Appl. No. 15/612,668, dated May 23, 2019, 10 pages.
Notice of Allowance issued by The United States Patent and Trademark Office for U.S. Appl. No. 15/612,709, dated Jun. 6, 2018, 14 pages.
Office Action issued in Japanese Patent Application No. 2017-562966, dated Aug. 4, 2020, 13 pages.
Office Action issued in Japanese Patent Application No. 2017-562966, dated Jan. 21, 2020, 10 pages.

* cited by examiner

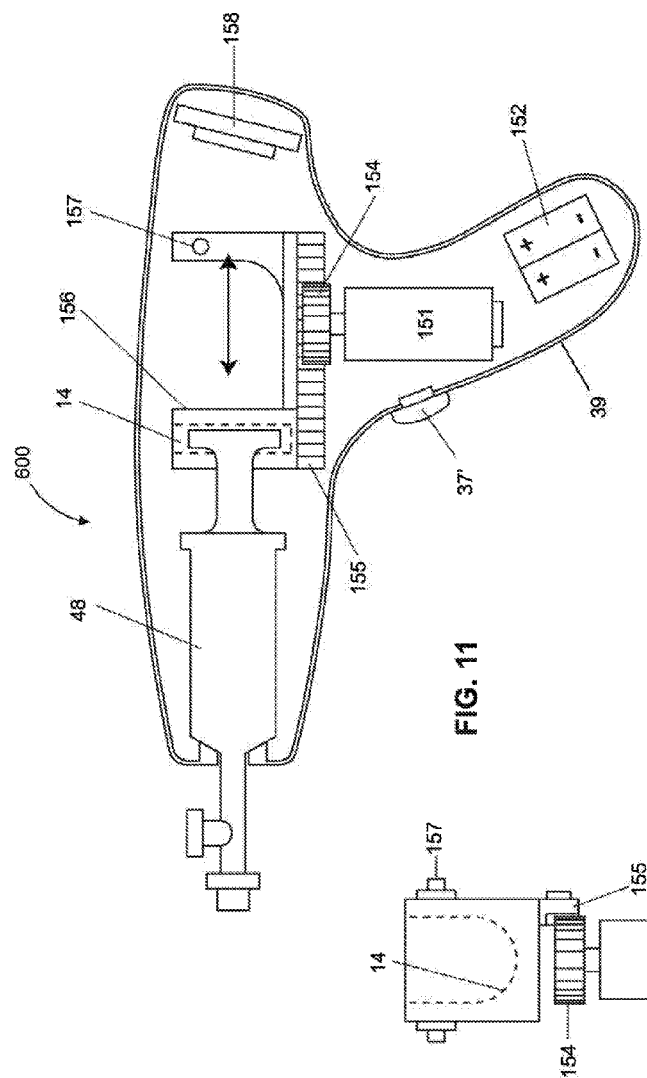
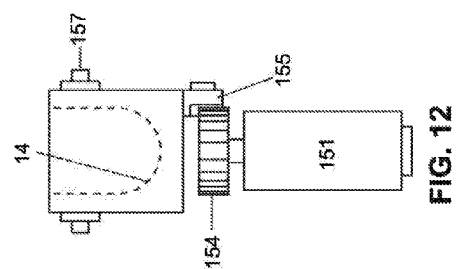

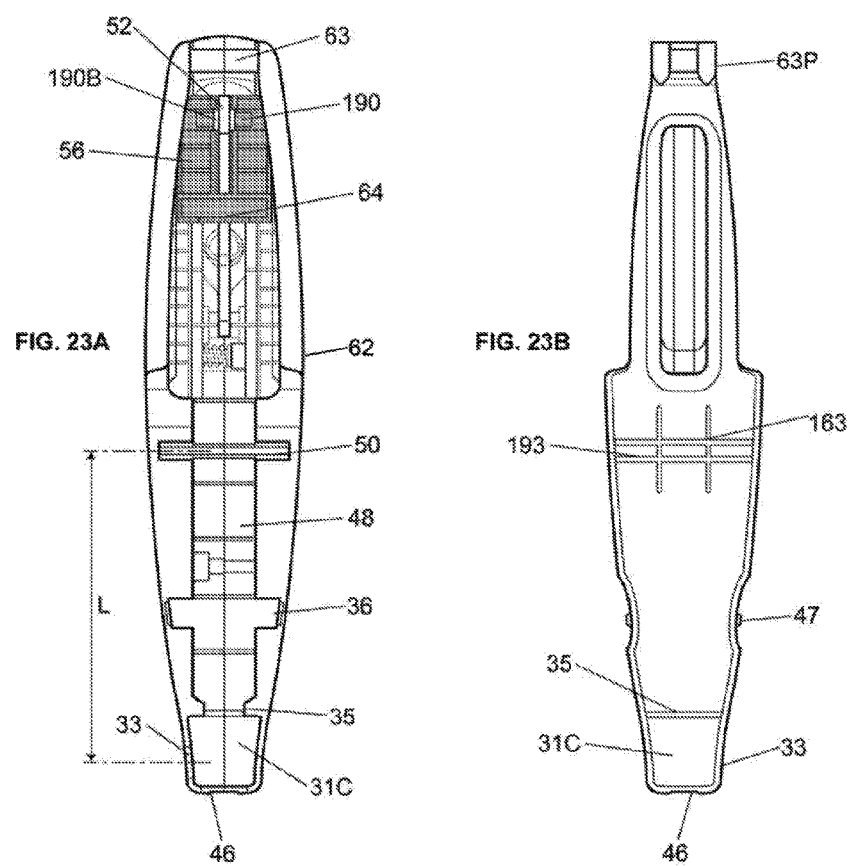

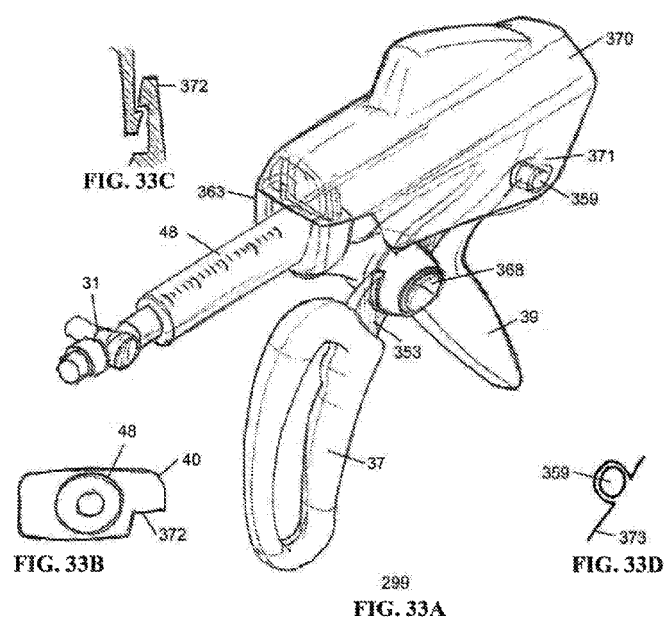

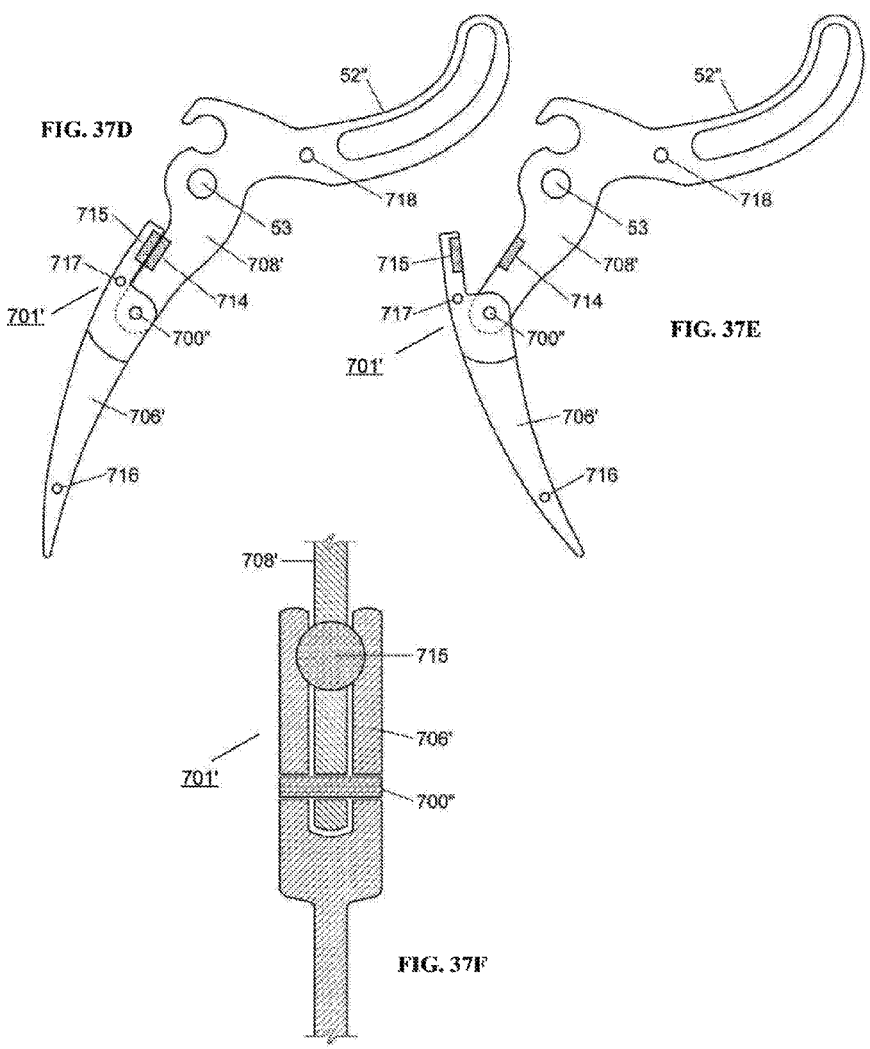

RAPID FLUID DELIVERY SYSTEM

CROSS-REFERENCE TO RELATED APPLICATIONS

This application is a continuation of U.S. patent application Ser. No. 16/548,490, filed Aug. 22, 2019, entitled "Apparatus and Kits for Fluid Infusion," now U.S. Pat. No. 11,458,256, which is a continuation of U.S. patent application Ser. No. 15/612,668, filed Jun. 2, 2017, entitled "Apparatus and Kits for Fluid Infusion," now U.S. Pat. No. 10,391,257, which is a continuation application of International Application No. PCT/US2016/019167, filed Feb. 23, 2016, entitled "Apparatus and Kits for Fluid Infusion," which claims the benefit of and priority to U.S. Provisional Application No. 62/274,566, filed Jan. 4, 2016, entitled "Apparatus and Method for Rapid Intraosseous Fluid Infusion," and U.S. Provisional Application No. 62/187,367, filed Jul. 1, 2015, entitled "Apparatus and Method for Rapid Intraosseous Fluid Infusion," and U.S. Provisional Application No. 62/120,021, filed Feb. 24, 2015, entitled "Apparatus and Method for Rapid Intraosseous Fluid Infusion," the contents of each of which are hereby incorporated by reference as if recited in full herein.

TECHNICAL FIELD

The present disclosure relates to dispensing medical fluid from a syringe. More particularly, the present disclosure relates to mechanisms and methods for syringe loading and dispensing fluid with assistance.

BACKGROUND

Rapid fluid administration is essential for patients suffering from shock, a life-threatening illness resulting from a variety of conditions including bacterial sepsis, hemorrhage, trauma, severe dehydration, and anaphylaxis. The American Heart Association's Pediatric Advanced Life Support (PALS) guidelines, the American College of Critical Care Medicine, and the Surviving Sepsis Campaign guidelines for adults recommend rapid fluid resuscitation as a key element of initial therapy. For example, PALS calls for 20 ml per kilogram of body weight to be infused over 5 minutes, and up to 60 ml/kg in the first 15 minutes.

In practice timely infusion of recommended fluid volumes is rarely achieved. This is often due to the difficulty of obtaining intravenous (IV) access in the setting of critical illness, and to the technical barriers to the infusion of large volumes of fluid. When IV access is difficult to obtain, the preferred technique is now intraosseous (IO) access, in which a needle is drilled directly into one of the long bones the arm or leg, and fluid is administered through the bone marrow into the central circulation. While IO infusion has revolutionized the approach to rapid access for fluid and medication administration in emergency medicine, it presents an additional challenge due to the resistance of the bone marrow, which makes rapid infusion of fluid difficult. These challenges are particularly common in children.

The increased resistance of bone marrow is similar to flow through small-bore or long IV catheters, and limits the ability of healthcare providers to deliver recommended volumes of resuscitation fluids rapidly.

Healthcare providers use several methods used to deliver fluid rapidly in these situations, include gravity, infusion pumps, pressure bags applied to the fluid reservoir, and hand-operated syringes, and mechanical rapid-infusion systems.

The fastest and most practical methods in higher-resistance situations are the hand-operated syringe techniques. The standard set of components used includes a fluid reservoir, a syringe, a three-way stopcock, and IV tubing linking these components with the IO or IV port. The user withdraws the plunger to fill the syringe from the fluid reservoir, turns the stopcock, and then depresses the plunger to drive the fluid through the IO or IV port and into the patient. The process is repeated multiple times until the desired volume has been delivered. Alternatively, one provider fills syringes from the IV fluid bag, while another connects the syringe, administers the fluid, disconnects the empty syringe, and repeats the process.

Both of these methods require emergency healthcare providers to either: 1) use great force with a large-volume syringe, often with two hands, and quickly resulting in user fatigue, or 2) to refill a small-bore syringe multiple times to achieve adequate volume, resulting in slow administration times and significant distraction for one or more workers. In either case two providers are often necessary, with one user infusing the fluid, and the other refilling syringes or operating the stopcock, and adequate fluid volumes are rarely achieved within the recommended time period.

Consider the example of a 40 kg child with traumatic injury and massive blood loss, who has a tibial IO needle as his only access. This child may require rapid infusion of 40-80 ml/kg of blood products, for a total of 1600-3200 ml. Repeated doses using a standard technique and 20 ml syringe would require 80-160 injections and the full attention of two healthcare workers, resulting in slow resuscitation and inefficient use of resources. The total infusion time could be 15-20 minutes, well outside the range of recommended rates, particularly in an actively bleeding child.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In some embodiments, an infusion device includes a housing with an interior chamber that is sized and configured to hold at least a flange and plunger of a syringe, a trigger held by the housing, and a lever in communication with the trigger and comprising an upwardly extending cam with a cam path having an upper end. The cam is in communication with the flange of the syringe. In response to actuation of the trigger to dispense fluid from the syringe, the upper end of the cam travels upward above the syringe and longitudinally toward a dispensing end of the syringe to linearly translate the plunger of the syringe in a first direction to dispense fluid from the syringe. To refill fluid into the syringe, the upper end of the cam travels downward and longitudinally away from the dispensing end of the syringe to linearly translate the plunger in a second opposing direction to intake fluid into the syringe.

The housing may include a lower housing member and a lid attached to the lower housing member. The lid may increase in height between longitudinally opposing ends of the housing to define an interior cavity that encases the upward end of the cam.

The cam may include a slot inside a closed perimeter that defines the cam path, and may further include a laterally extending pin extending through the slot of the cam. The cam and the pin may cooperate to move the syringe in the first direction to dispense fluid and to move the syringe in the opposing direction to intake the fluid. Optionally, the slot may have upper and lower arcuate ends.

The infusion device may further include a shuttle attached to a laterally extending bracket that engages the upper end of the cam to move the syringe in the first direction to dispense fluid and to move the syringe in the opposing direction to intake the fluid. Optionally, the bracket may include a first cross bar and a longitudinally spaced apart second cross bar which together define an opening above which the upper end of the cam can extend.

The interior chamber may be sized and configured to hold at least the flange and plunger of a respective syringe with a volumetric capacity in a range of 5 ml to 30 ml. The upper end of the cam may be configured to travel up and down a distance of between about 1.25 inches and about 2.25 inches in the enclosed cavity during operative use of the infusion device. The cam may include a concave shape that faces the syringe.

The housing may be sized and configured to hold an elongate syringe body of the syringe in the interior chamber. The housing may have an upper portion that is visually transmissive over at least a portion thereof that resides above the interior chamber. The device may further include a dual check valve attached to the dispensing end of the syringe with an inlet tube of the dual check valve extending out of one side of the housing to orient the syringe to have visual indicia of fluid volume facing upward. The inlet tube may extend outward perpendicular to the axially extending valve body to be parallel with a laterally extending plane of the flange of the syringe. Optionally, the flange may reside a distance between 3 and 5 inches from an axially extending centerline of the inlet tube. Optionally, the inlet tube may be fixedly or releasably attached to a length of large bore tubing.

The infusion device may further include a dual check valve attached to the dispensing end of the syringe with an inlet tube of the dual check valve extending out of one side of the housing. The lid may include a plurality of spaced apart downwardly facing apertures on or adjacent a front end thereof adjacent a dispensing end of the syringe, including a first forwardmost aperture sized and configured to extend about a tubular exit port of the dual check valve body and at least one second aperture positioned on a right and/or left sidewall of the lid to be adjacent, but spaced longitudinally apart from, the first forwardmost aperture. The spacing may be in a distance of between 0.5 inches to 1 inch, optionally about 0.8 inches.

The at least one second aperture on the right and/or left sidewall may include a pair of second apertures that are symmetrically positioned across from one another on the right and left sidewalls of the lid.

The lid may have opposing front and rear ends. The front end may have a tip with a semicircular aperture. A front end of the lower housing member may also include a tip with a semicircular aperture facing the semicircular aperture in the tip of the lid to form a circular aperture when the lid is closed against the lower housing member.

The lid may have a front end having a tip with an aperture and at least one sidewall proximate the tip may also have an aperture. The lower housing member may have a front end including a tip with an aperture facing the aperture in the tip of the lid and an aperture on at least one upwardly extending sidewall facing a respective aperture in a corresponding sidewall of the lid. Respective pairs of apertures from the lid and lower housing member may align to form respective ports when the lid is closed against the lower housing member.

A front end of the lid may have a tip with a downwardly extending semicircular aperture and at least one sidewall proximate the tip that also may have a downwardly extending semicircular aperture. The lower housing member may have a front end residing under the front end of the lid. The front end of the lower housing member may include a tip with an upwardly extending semicircular aperture facing the semicircular aperture in the tip of the lid and an upwardly facing semicircular aperture on at least one upwardly extending sidewall facing a respective semicircular aperture in the sidewall of the lid. Respective pairs of semicircular apertures in the lid and lower housing member may form circular apertures when the lid is closed against the lower housing member.

A center of an aperture formed by at least one pair of aligned apertures of a sidewall of the lid and lower housing member may reside spaced apart a distance in a range of 0.7 inches to 1 inch from a syringe neck holding segment in the interior chamber to thereby provide a positive orientation of a check valve with respect to visual indicia on a syringe when mounted inside the interior chamber.

The interior chamber may have a first compartment sized and configured to hold a syringe body that merges into a smaller region for a length that is sized and configured to hold a neck of a respective syringe. The interior chamber first compartment may merge into a second compartment that extends to a tip and can be sized and configured to hold a dual check valve body therein so that an exit port extends out of the tip of the lid and an underlying lower housing member and an inlet tube extends out of a side of the lid and the underlying lower housing member, adjacent the tip. Optionally, a length of large bore tubing may be releasably or fixedly attached to the inlet tube and resides external to the device.

A respective port formed by the aligned apertures of the front end of the lid and lower housing may be larger than the port formed by the aligned apertures on the right and/or left sidewall.

The cam may engage a shuttle to linearly translate the plunger. The cam may be pivotably attached to the lever about a fixed pivot point in the housing under the shuttle. The trigger may include either a downwardly extending hand grip with a manually operable trigger or an electronic trigger.

The curvilinear cam may have a downwardly extending segment or extension that contacts the trigger or is integral to the trigger and extends below the fixed pivot point. The device may further include a torsion spring attached to a trigger anchor held adjacent the fixed pivot point for biasing the trigger to a return position. The downwardly extending segment or extension of the cam may include an arcuate open space above the fixed pivot point and a laterally extending and slidable pin lock member that may be slidably received in the arcuate open space to thereby lock and unlock the trigger.

The trigger may include a manual lever that has a stroke distance that is the same or no more than 20% longer than a plunger stroke distance of the syringe in the housing.

The infusion device may further include a syringe configured to be held by the housing with at least the flange in the interior chamber of the housing, a valve attached to the syringe and held by the housing, large bore tubing having an inner diameter greater than 3 mm and less than or equal to 6 mm and a length in a range of 4 feet to 10 feet, a small bore tubing assembly with a length of small bore tubing having an inner diameter of between 3 mm to 1 mm configured to attach to the exit port of the valve body, a clamp attached to the small bore tubing, and a Y connector attaching adjacent ends of first and second lengths of the small bore tubing. The syringe may have a syringe body with a liquid chamber having a volumetric capacity in a range of 5 ml to 30 ml, the syringe having an external surface with visual indicia of volume and a plunger that can slidably extend into and retract at least partially from the syringe body. The valve may include an axially extending valve body with opposing first and second ends, the valve body including (a) an inlet tube residing between the first and second ends of the valve body and (b) an exit port on the first end of the valve body. The second end of the valve body may reside adjacent or inside the syringe and is in fluid communication with the liquid chamber. The large bore tubing may have opposing longitudinally spaced apart first and second ends, with the first end of the large bore tubing attached to the inlet tube and the second end comprising a spike. The first and second lengths of small bore tubing may each have a free end of the tubing, away from the Y connector, one with a male luer connector and one with a female luer connector. The syringe with the attached valve, the large bore tubing attached to the inlet tube of the valve body, and the small bore tubing attached to the exit port of the valve body may all be held in a sterile package prior to use in the infusion device to thereby be provided in a sterile and ready-to-use assembly.

The infusion device may further include a syringe held by the housing, a dual check valve attached to a dispensing end of the syringe and in fluid communication with the liquid chamber of the syringe, and either or both: (a) a small bore tubing assembly with a length having an inner diameter of between 3 mm to 1 mm configured to attach to an exit port of the dual check valve, a clamp attached to the small bore tubing, a Y connector attaching adjacent ends of first and second lengths of small bore tubing, the first and second lengths of small bore tubing each having a respective free end away from the Y connector, one having a male luer connection and one having a female luer connector, optionally for a needleless valve configuration, or (b) a small bore tubing assembly with a length of small bore tubing having an inner diameter of 3 mm to 1 mm configured to attach to an exit port of the dual check valve and having a male luer connection on an end of the small bore tubing away from the end attached to the exit port. The syringe may have a syringe body with a liquid chamber having a volumetric capacity in a range of 5 ml to 30 ml.

The infusion device may further include a syringe held by the housing, a dual check valve attached to a dispensing end of the syringe and in fluid communication with the liquid chamber of the syringe, and one or more of the following: (i) a contrast agent tubing sub-assembly with first and second segments of inlet tubing, with at least one segment including a length of large bore tubing, each of the first and second segments of inlet tubing having one end with a spike, the first and second segments connected by a two-way selector valve configured to attach to the inlet port of the inlet tube for a cardiology infusion procedure; (ii) a length of small bore outlet tubing between the exit port of the dual check valve and comprising a pressure relief valve in fluid communication with the syringe; and (iii) first and second lengths of large bore tubing, each comprising a clamp and a large bore spike inserted/insertable into a corresponding first and second pouch of liquid, where the first and second lengths of large bore tubing meet at an in-line filter adjacent a Y connector that merges into a single large bore inlet tubing segment attached to the inlet tube of the dual check valve to thereby allow a user to attach one pouch comprising blood or blood product to the first length of large bore tubing and another comprising an infusion liquid (optionally saline) to the second length of large bore tubing. The syringe may have a syringe body with a liquid chamber having a volumetric capacity in a range of 5 ml to 30 ml. The dual check valve may include an axially extending primary body and an inlet tube with an inlet port residing longitudinally spaced apart from an exit dispensing port.

The infusion device may further include a syringe held by the housing, at least one pressure load cell in the housing coupled to the syringe that generates a signal associated with a measured pressure or force being applied to the syringe by a user through the trigger, and a processor in communication with the at least one pressure load cell which is configured to determine a fluid pressure of a fluid dispensed based on the force or pressure measured by the pressure load cell. The fluid pressure may be determined based on the force or pressure measured by the pressure load cell and a diameter of the plunger of the syringe. The syringe may have a syringe body with a liquid chamber having a volumetric capacity in a range of 5 ml to 30 ml. The syringe may have a plunger that can slidably extend into and retract at least partially from the syringe body.

The infusion device may further include a syringe held by the housing, a valve attached to the syringe and held by the housing, a pressure sensor or load cell in fluid communication with the syringe and/or an fluid intake or discharge flow path, and a user interface with a display in communication with a processor. The syringe may have a syringe body with a liquid chamber having a volumetric capacity in a range of 5 ml to 30 ml, the syringe having a plunger that can slidably extend into and retract at least partially from the syringe body. The valve may include an axially extending valve body with opposing first and second ends. The valve body may include (a) an inlet tube residing between the first and second ends of the valve body and (b) an exit port on the first end of the valve body. The second end of the valve body may reside adjacent or inside the syringe and is in fluid communication with the liquid chamber. The user interface may be configured to allow a user to select a desired pressure limit associated with a type of fluid source (optionally an IV bag) attached to an inlet port of tubing attached to the inlet tube of the valve.

The infusion device may be configured to disable the plunger of the syringe when the determined fluid pressure of the fluid dispensed exceeds a defined limit.

The interior chamber may be sized and configured to releasably and serially interchangeably hold syringes of different volumes. Respective ones of the serially interchangeable syringes of different volumes may have a common length.

Respective ones of the serially interchangeable syringes of different volumes may have a common stroke length. The stroke length may be a distance traveled by a respective plunger of the syringe through the syringe body. The flange of each respective syringe of the serially interchangeable syringes of different volumes may include at least one of a common flange width, a common flange height, and a common flange thickness.

The infusion device may further include a processor held by the housing. The processor may be configured to correlate a volume of a respective syringe then held in the housing with a pressure applied to the trigger to determine a pressure of the fluid being dispensed through the outlet port. The processor may direct the device to generate an audible and/or visual alert when total fluid dispensed reaches a defined limit which can optionally be a user set limit.

The infusion device may further include a processor and at least one sensor held by the housing. The processor may communicate with the at least one sensor to identify what syringe type and/or volume is currently held in the housing based on a radial extension of the syringe.

The housing may include a tube retaining feature extending laterally across a width dimension of the housing perpendicular to longitudinal direction of the housing adjacent a forward end portion of the housing configured to releasably hold a length of large bore tubing.

The tube retaining feature may include a cross-channel in a lower portion of the housing extending from a right side of the housing to the left side of the housing between the trigger and forward end of the housing.

The tube retaining feature may include at least one retaining clamp attached to lower portion of the housing and extending downwardly configured to releasably hold a length of tubing.

The cam may include a downwardly extending lever segment that, in use, resides below the syringe and is attached to the trigger and that rotates about a fixed pivot point. The downwardly extending lever may include first and second segments that reside below the fixed pivot point that are configured to break responsive to an application of force by a user that exceeds a defined force. The downwardly extending lever may include first and second segments that reside below the fixed pivot point that are configured to disengage with a resettable hinge in response to an application of force by a user that exceeds a defined force.

The infusion device may further include an encoder in communication with the syringe to provide dispensed volume information to a user.

The infusion device may further include a kit with first and second sterile packages of components. The first sterile package may include a syringe held by the housing, the syringe having a syringe body with a liquid chamber having a volumetric capacity in a range of 5 ml to 30 ml, a dual check valve attached to a dispensing end of the syringe and in fluid communication with the liquid chamber of the syringe, and small bore tubing having an inner diameter of between 3 mm to 1 mm configured to attach to an exit port of the dual check valve, a clamp attached to the small bore tubing, and a Y connector attached to the small bore tubing. The second sterile package may include a syringe of pain medication (optionally lidocaine) for attaching to the Y connector for dispensing the pain medication to a user through the small bore tubing.

The infusion device may further include a kit with first and second sterile packages of components used with the device. The first sterile package may include a syringe to be inserted into the housing, the syringe having a syringe body with a liquid chamber having a volumetric capacity in a range of 5 ml to 30 ml, a dual check valve pre-attached to a dispensing end of the syringe and in fluid communication with the liquid chamber of the syringe, and small bore tubing having an inner diameter of between 3 mm to 1 mm configured to attach to an exit port of the dual check valve, a clamp attached to the small bore tubing, and a Y connector attached to the small bore tubing. The second sterile package may include a first syringe of a pain medication (optionally lidocaine) and a second syringe of buffer (optionally sodium bicarbonate) each configured to be in fluid communication with the Y connector to provide a buffered pain medication to a user through the small bore tubing.

In some embodiments, an infuser system includes a housing configured to hold a syringe with a plunger, a shuttle in the housing configured to engage the plunger of the syringe, and a trigger including a lever held by the housing. The lever rotates about a fixed pivot point under the syringe. The lever includes a first segment and a second segment that, during normal operation, cooperate to linearly translate the shuttle in a first direction in response to actuation of the trigger and rotation of the lever about the fixed pivot point. One or both of the first and/or second segment is configured to disengage and/or break responsive to an application of a force to the trigger by a user that exceeds a defined force. The infusion system is configured to dispense fluid from the syringe responsive to actuation of the trigger. The defined force is correlated to be above a maximal desired pressure at which the fluid is dispensed from the syringe.

The defined force may be about 70 lbf, optionally between 70 lbf and 100 lbf.

The first and/or second segment of the lever may include an aperture positioned below the fixed pivot point and adjacent an outer edge of the lever. The aperture may have a first original configuration with a wall surrounding the aperture that changes to a second deformed configuration where the wall separates about a portion of the aperture during use responsive to the application of force by the user that exceeds the defined force to thereby disengage and/or break the lever.

The aperture may be positioned to be within between 0.01 and 0.1 inches from the outer edge of the lever. Optionally, the second segment of the lever may include a first material and a second material different than the first material.

The defined force may be defined so as to disengage and/or break the first and/or second segment of the lever when the pressure of the fluid dispensed from the syringe exceeds a pressure between 5.8 PSI to 325 PSI.

The lever may include a cam with a slot residing above the first segment. The first segment may be pivotably connected to the second segment with a pivot pin below the fixed pivot point.

The first and/or second segment of the lever may be configured to reattachably disengage from each other. The device may further include a resettable hinge between the first segment and the second segment which disengages the segments when the user applies a force that is greater than or equal to the defined force.

The first segment may be pivotably connected to the second segment with a pivot pin below the fixed pivot point. The resettable hinge may include a spring-loaded plunger that resides above the pivot pin that can laterally extend and retract to respectively engage and disengage with an aligned recess. During operation of the infuser system the spring-loaded plunger may disengage from the recess when the user applies the force that is greater than or equal to the defined force.

The infuser system may further include a restraint mechanism that can be selectively engaged to the resettable hinge. The restraint mechanism may be configured to disable the resettable hinge such that the lower portion is restricted from pivoting and the first and second segments remain operatively engaged even when the user applies the force that is greater than or equal to the defined force.

The defined force may be defined so as to pivot the lower portion of the second segment of the lever away from the first segment of the lever when the pressure of the fluid dispensed from the syringe exceeds a defined pressure. The defined pressure may be between 5.8 PSI to 325 PSI.

The first segment may be pivotably connected to the second segment with a pivot pin below the fixed pivot point. The resettable hinge may include at least one magnet below the pivot pin.

The at least one magnet of the resettable hinge may include at least a first magnet on the first segment and at least a cooperating second magnet on the second segment. The first and second magnets may be configured to magnetically couple during normal operation of the infuser system and decouple when the user applies the force that is greater than or equal to the defined force.

The at least one magnet may include at least one magnet on one of the first or second segments and a cooperating ferromagnetic and/or rare earth magnet on another of the first or second segments that are configured to magnetically couple during normal operation of the infuser system and decouple when the user applies the force that is greater than or equal to the defined force.

Some embodiments of the present invention are directed to a kit of components for a medical infusion for infusion devices and infuser systems. The kits include: a syringe having a syringe body with a liquid chamber having a volumetric capacity in a range of 5 ml to 30 ml, the syringe having an external surface with visual indicia of volume and a plunger that can slidably extend into and retract at least partially from the syringe body; large bore tubing having an inner diameter greater than 3 mm and less than or equal to 6 mm and a length in a range of 4 feet to 10 feet, the large bore tubing having opposing longitudinally spaced apart first and second ends; a valve with an axially extending valve body with opposing first and second ends, the valve body including (a) an inlet tube residing between the first and second ends of the valve body and (b) an exit port on the first end of the valve body; and a package holding the syringe pre-attached to the valve body and the large bore tubing in a sterile condition separate from or pre-attached to the inlet tube to thereby provide components in a ready-to-use configuration for insertion of the syringe and valve into an infusion device.

The inlet tube may be attached to the first end of the large bore tubing. The second end of the valve body may reside adjacent or inside the syringe and is in fluid communication with the liquid chamber. The inlet tube may extend outward perpendicular to the axially extending valve body to be parallel with a laterally extending plane of the flange of the syringe. Optionally, the flange may reside a distance between 3 inches and 5 inches from an axially extending centerline of the inlet tube. An axially extending centerline of the inlet tube may be longitudinally spaced apart a distance of 0.7 inches from an exit tip of the syringe body. Attached to the inlet tube, the large bore tubing may be parallel to the flange and is oriented to position the volume indicia facing upward.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 11 is a cross sectional view of a powered delivery mechanism, according to at least one embodiment, having a powered shuttle advancement for dispensing fluid from a syringe according to embodiments of the invention.

FIG. 12 is a view of the motor and gear of FIG. 11, taken along the advancement axis, shown engaging the shuttle according to embodiments of the invention.

FIG. 23A is a top view of an example embodiment of a housing without a lid according to embodiments of the invention.

FIG. 23B is a bottom view of an example embodiment of a lid of a housing according to embodiments of the invention.

FIG. 33A is a schematic illustration of another example embodiment of a compact housing according to embodiments of the invention.

FIG. 33B is an enlarged view of an example embodiment for the compact housing of FIG. 33A of a syringe flange according to embodiments of the invention.

FIG. 33C is an enlarged view of an example embodiment for optional locking tabs for the compact housing of FIG. 33A according to embodiments of the invention.

FIG. 33D is an enlarged view of an example embodiment for optional detents of the compact housing of FIG. 33A according to embodiments of the invention.

FIG. 37D is a side view of an example embodiment of a lever with a resettable hinge with a magnetic latch according to embodiments of the invention.

FIG. 37E is a side view of the lever shown in FIG. 37D with the resettable hinge, after disengaging, according to embodiments of the invention.

FIG. 37F is a partial cross-sectional view of the example embodiment of the lever with the resettable hinge shown in FIG. 37D, according to embodiments of the invention.

DETAILED DESCRIPTION

Figure 1:
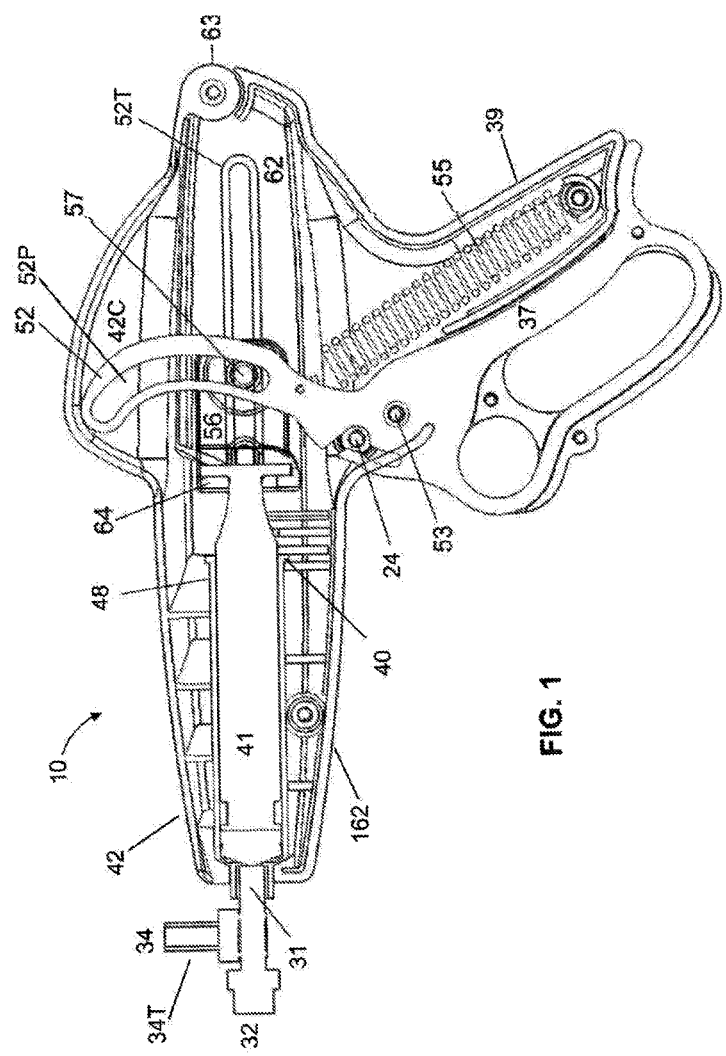
FIG. 1 is a cross sectional view of a delivery mechanism according to at least one embodiment of the invention.
Figure 2:
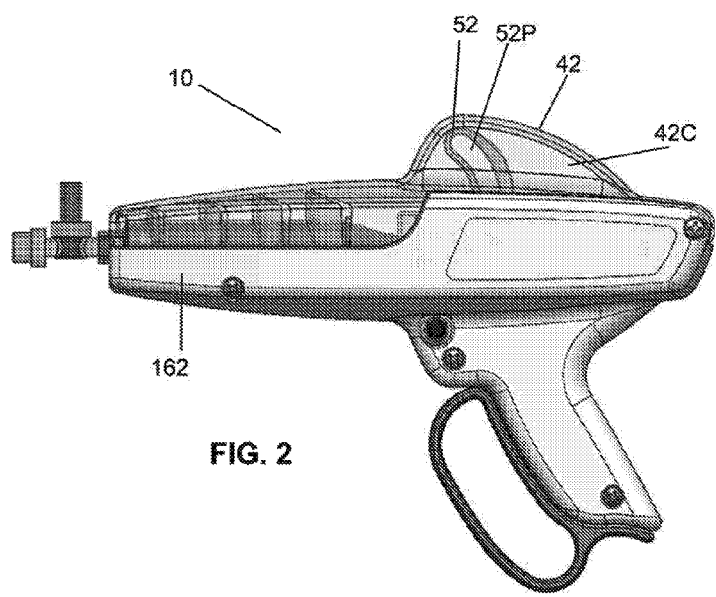
FIG. 2 is a side view of the delivery mechanism of FIG. 1 according to embodiments of the invention.
Figure 3:
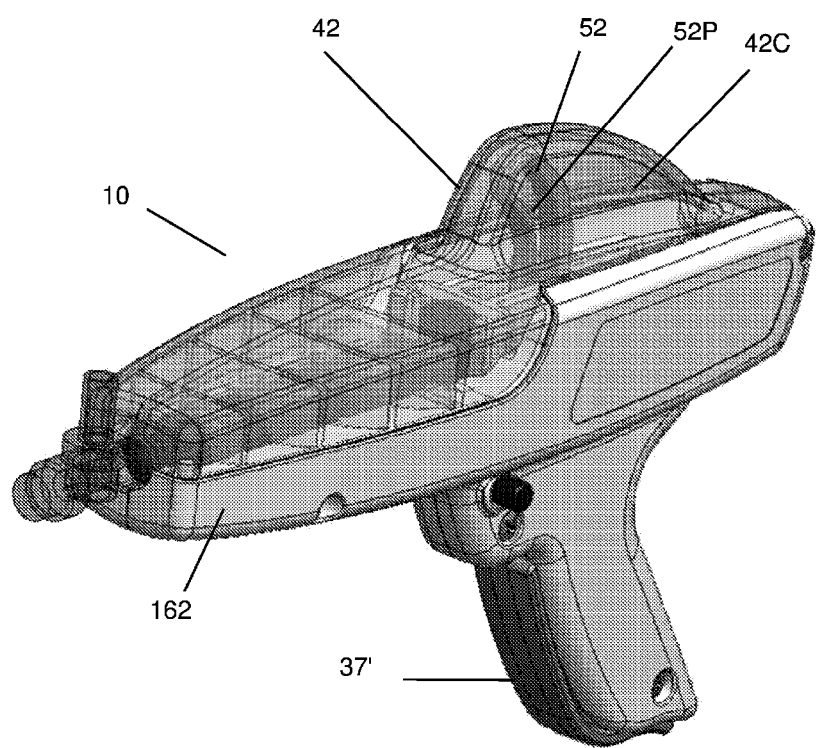
FIG. 3 is an isometric view of the delivery mechanism of FIGS. 1-2 according to embodiments of the invention.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers typically refer to like elements throughout. In the figures, the thickness of certain lines, layers, components, elements or features may be exaggerated for clarity. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y" The term "about" means that the recited parameter can vary from the noted value, typically by +/−20%.

The term "sterile" means that the noted device or material meets or exceeds defined medical guidelines (e.g., regulatory) of cleanliness such as those required by the U.S. Food and Drug Administration (FDA) and is substantially (if not totally) without contaminants so as to be suitable for medical uses. In some embodiments, sterile devices or materials may be provided in a sterile package such as, but not limited to, a flexible pouch.

The term "instructional media" refers to electronic and/or paper manuals, videos, user guides, or the like illustrating and/or describing operation of the debridement tool and/or the spinal facet debridement surgical procedure.

The term "large bore" refers to tubing or openings with an ID (inner diameter) between greater than 3 mm and less than or equal to 6 mm, typically greater than or equal to 3.5 mm and less than or equal to 6 mm. Large bore can be about 3.5 mm, about 4 mm, about 4.5 mm, about 5 mm, about 5.5 mm, or about 6 mm. The term "small bore" refers to tubing or openings with an ID between greater than or equal to 1 mm and less than or equal to 3 mm, typically between greater than or equal to 2 mm and less than or equal to 3 mm.

The term "pain medication" refers to analgesics and/or anesthetics, including medications comprising lidocaine, prilocaine, benzocaine, mepivicaine, etidocaine, articaine, bupivacaine, procaine, tetracaine, and/or marcaine. In some embodiments, a medical buffering solution may be added to pain medication to decrease pain experienced during administration of the pain medication. The medical buffering solution may include, for example, sodium bicarbonate, sodium hydroxide, calcium bicarbonate, magnesium oxide, potassium hydroxide, sodium carbonate, tris(hydroxylmethyl)aminomethane and the like.

The embodiments of the invention discussed herein may be used with both humans and animals. As such, the term "patient" refers to both human and animal patients.

FIGS. 1-5 depict a system 10 to infuse fluid. The system 10 may operate to infuse fluid from a syringe 48 in response to input from a user. In some embodiments, the syringe 48 may be serially interchangeable in the system 10. The system 10 may accept various sizes of syringes 48. For example, the system 10 can accept 5 ml, 10 ml, 15 ml, 20 ml, 25 ml, and 30 ml syringes 48, though the present invention is not limited thereto. In some embodiments, the system 10 may be configured so as to allow the user to interchange a first syringe 48 of a first size with a second syringe 48 of a second size, different from the first size, during use of the system 10. The syringe 48 can be integral to the system 10, affixed thereto or releasably attached.

The system 10 may also include a stationary grip 39 for the user to grasp the system 10 during operation. As shown in FIGS. 1-5, the system 10 may include a trigger 37 accessible to the user while holding the grip 39. The trigger 37 may be a manual/mechanical trigger 37 as shown in FIGS. 1-5 or may comprise an electronic trigger 37' (i.e., FIGS. 11, 47A) which allows a user to intake and dispense fluid from the syringe 48. In some embodiments, the trigger 37 can rotate about a fixed pivot point 53.

Figure 4:
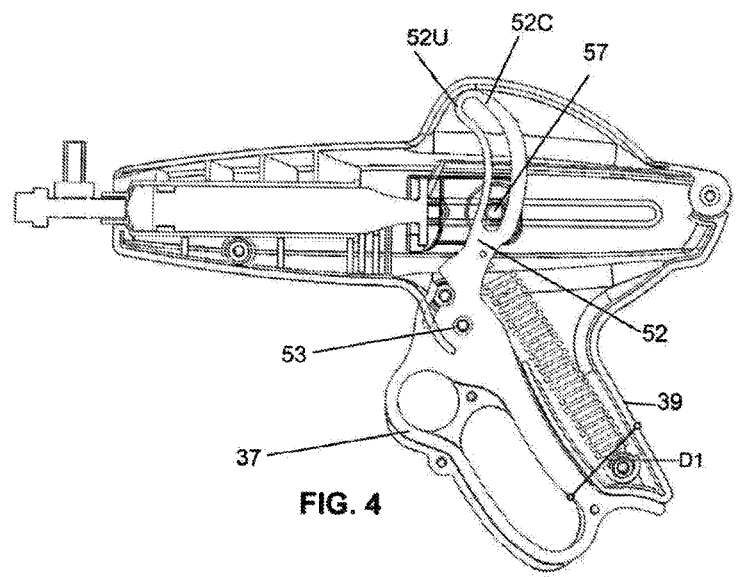
FIG. 4 is a side view of the delivery system of FIG. 1 in a closed position, showing an exemplary non-binding dimensional measurement according to embodiments of the invention.
Figure 5:
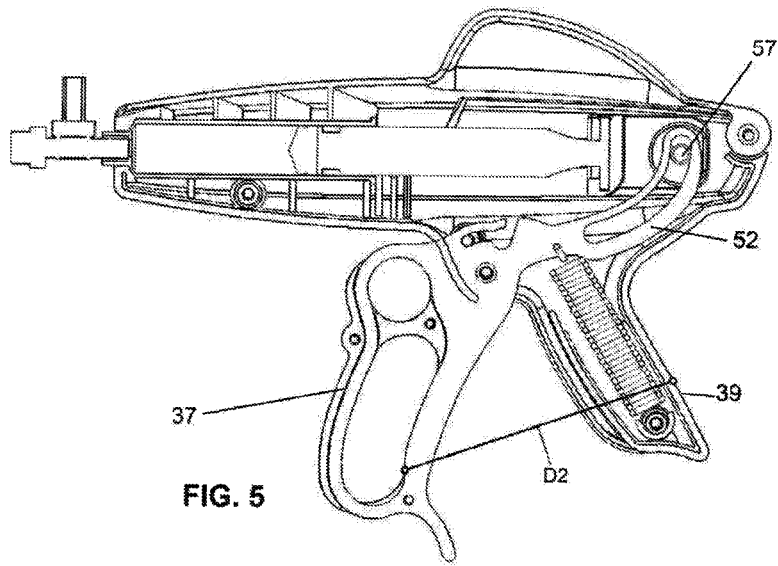
FIG. 5 is a side view of the delivery system of FIG. 1 in an open position, showing another exemplary non-binding dimensional measurement according to embodiments of the invention.

The infusion device 10 can include a lever 52. The upper part of the lever 52U (FIG. 4) is in communication with and/or includes a lever 52 containing a cam 52C which may have a closed cam path 52P that can change the rotational motion of the trigger 37 into axial motion of the shuttle mechanism 56, which, in turn, holds the plunger 41. A pin 57 or other attachment member can be fixed to the shuttle mechanism 56 and can travel along a track 52T in response to interaction with a cam 52C (FIG. 4) of the lever 52. A return spring 55 can return the trigger 37 to an extended open position (FIG. 5) when firing is complete by actuation of the trigger 37 to the retracted position (FIGS. 1-4). The return spring 55 can be connected close to the pivot point 53 on the lever 52 portion of the actuation trigger 37, and also to the housing 62 and can be contained within a stationary grip 39 of the housing 62. Trigger 37 is shown in a closed state in FIGS. 1 and 4. The shuttle mechanism 56 can have a slot 64 which accepts the outer end of the syringe plunger 41. Slot 64 can be open at the top so a syringe 48 can be dropped in from above. The body of the syringe 48 can have a flange 40 which is held by a receiving slot 50 in the housing body (illustrated in FIG. 22). This can hold the syringe 48 in place while the plunger 41 is actuated. A lid 42 can pivot open and close about a fixed pivot 63, which allows access for the syringe 48 during loading, but protects the user from all moving parts during use. Lid 42 can be held down to the lower housing member 162 with magnets or other attachments or locks. A number of different features including, but not limited to, magnets, detents, latches or other mechanisms may also be used to secure the lid 42 to the housing 62. The lid 42 may contain a lid cavity 42C. An upper portion 52U (FIG. 4) of the lever 52 can be configured to travel up and down a distance of between about 1.25 inches and about 2.25 inches in the lid cavity 42C during the use of the housing 62. The lever 52 may have a stroke distance that is the same or no more than 20% longer than the stroke distance of the plunger 41. As illustrated in FIGS. 4 and 5, the lever 52 may travel a stroke distance which may be a distance D1 to a distance D2 from a given point on the stationary grip 39. In some embodiments, the stroke distance may be from 1.25 inches to 3.5 inches. A lock button 24 can be moved transversely by the user. When moved to the locked position, the trigger 37 will be held in the closed position as shown. When the lock button 24 is moved to the unlocked position, the trigger 37 is free to move unimpeded. This can be accomplished by a large diameter present on the lock button, which enters a large diameter circular cut-out in the trigger, locking the motion. When the lock button 24 is pushed to the "unlock" position, a smaller diameter in the lock button can align with the smaller diameter cut-out in the trigger to allow unimpeded motion. The syringe 48 can be connected to a dual check valve 31. The inlet 34 of the dual check value 31 can allow fluid from the fluid reservoir to enter the syringe 48 when the plunger 41 is retracted. The outlet 32 of the dual check valve 31 can allow high pressure fluid to exit the syringe 48 when the plunger 41 is forcibly depressed, and travel to the patient.

Suitable dual check valves are currently manufactured by a number of suppliers in the medical field, including companies such as BBraun (B. Braun Medical Inc., Bethlehem, PA) and Merit (Merit Medical Systems, Inc., Salt Lake City, UT). Non-exhaustive examples of possible valves include part numbers S5401086SN, S5401096SN, and S5069200N from BBraun and part numbers 500012002, 500012003, and 500012006 from Merit. These valves provide a variety of different connection methods to the inlet tubing, outlet tubing, as well as the syringe, including slip fit, luer fit, and tubing pocket fits. In some embodiments, the infusion system can be configured to reduce the resistance to flow on the exit and/or the inflow of the fluid into the syringe. Embodiments of the invention can also or alternatively be configured to reduce the amount of turbulent flow that occurs, especially when passing blood products through the tubing. To that end, appropriate valve designs may be utilized such as to reduce the resistance to fluid flow. Check valve designs such as ball check, diaphragm check, duckbill, lift check and/or flapper valves may be used to create the dual check valve configuration for operation. Ball and cage valves are another option which may be well suited for cycling blood. Additionally or alternatively, a split flapper valve can be used. The split flapper valve can be configured to pivot open in the center and can allow the fluid to travel in a straighter path, reducing resistance to flow. Alternatively or additionally, a split valve with two pivot points located outside the main fluid travel channel with the split located in the center of the channel can also allow the fluid to travel in a straighter path. Some valves mentioned above have small bore openings when going through luer fittings and other connections to the syringe and or tubing. A syringe with a large bore opening may be used to directly integrate into at least one of the valve housings, which may also reduce resistance to fluid flow and/or decrease turbulent flow. In some embodiments, large bore openings may also be used in all fluidic inlet and/or outlets from the dual check valve.

Figure 7:
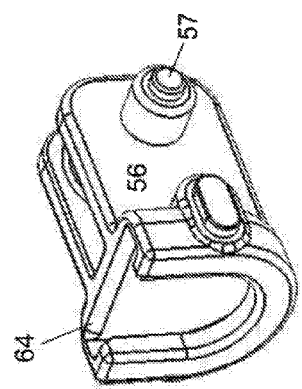
FIG. 7 is a perspective view of just the shuttle mechanism of FIG. 6 according to embodiments of the invention.
Figure 6:
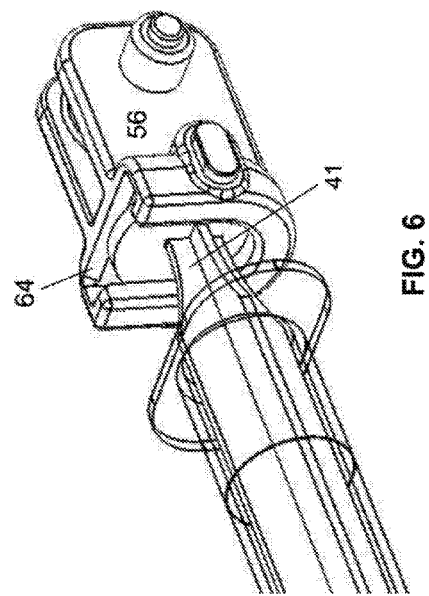
FIG. 6 is a perspective view of a shuttle mechanism of FIG. 1 engaging the operator-end of a syringe plunger according to embodiments of the invention.

FIGS. 6 and 7 depict a shuttle mechanism 56 having a slot 64 which can hold the operator end of the syringe plunger 41. Slot 64 can be configured such that the plunger 41 can be dropped into the shuttle mechanism 56 vertically from above, and then can actuate the plunger 41 while remaining in place in the shuttle mechanism 56. A view of the shuttle mechanism 56 without the plunger 41 present is also shown.

The shuttle 56 can be approximately 1.5 inches in length, 1 inch in width, and 1 inch in height. The shuttle 56 can capture the syringe plunger 41 in a slot 64 positioned at its forward end, and can be connected to the lever 52 at its rear end by a 0.25 inch diameter pin, which further slides within two 0.25 inch slots which guide the shuttle 56 parallel to the long axis of the device. The shuttle 56 can have a small groove just large enough for the plunger 41 of a 5 ml, 10 ml, 20 ml or 30 ml syringe 48 to be dropped in from the top. In some embodiments, other syringe 48 sizes may be supported. The groove can be sized to capture more than 50% of the syringe plunger 41. This can allow the syringe 48 to be dropped in freely from the top, but can securely capture the device during actuation. A similar groove can also present on the housing 62, which can capture the body of the syringe 48, and can allow the shuttle 56, when moved back and forth, to actuate the syringe 48.

Figure 8A:
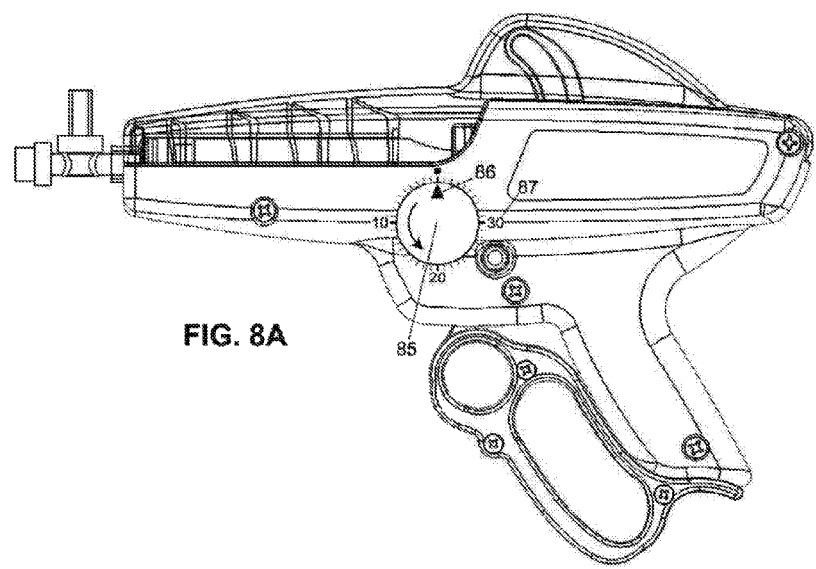
FIG. 8A is a view of a delivery mechanism having a tracking wheel for counting strokes of the trigger according to at least one embodiment according to embodiments of the invention.
Figure 8B:
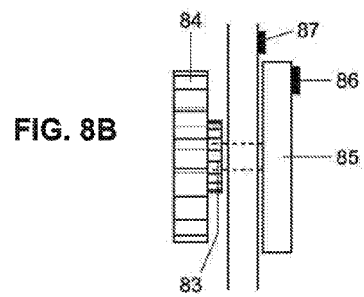
FIG. 8B is a close view of the tracking wheel of FIG. 8A, taken along the plane of the wheel according to embodiments of the invention.
Figure 8C:
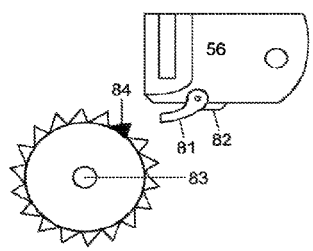
FIG. 8C is a close view of gear and pawl devices of the tracking wheel of FIGS. 8A and 8B according to embodiments of the invention.
Figure 8D:
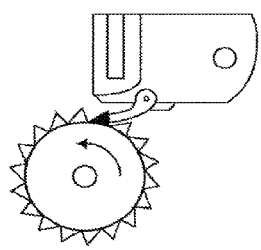
FIG. 8D is a view of the gear and pawl devices of FIG. 8C shown in a more advanced counting position, the pawl shown engaged as when advancing the gear during forward advancement of the shuttle of the delivery mechanism according to embodiments of the invention.
Figure 8E:
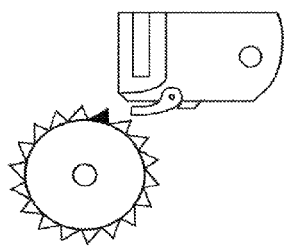
FIG. 8E is a view of the gear and pawl devices of FIGS. 8C and 8D, the pawl shown disengaged as when allowing the shuttle to retract according to embodiments of the invention.

In some embodiments, the volume of fluid dispensed from the syringe 48 can be electronically or mechanically tracked. There are multiple ways to track the volume of fluid being infused. For example, a mechanical counting mechanism can be integrated into the housing 62, which can count each full closure of the trigger 37. One embodiment of a mechanism is shown in FIGS. 8A-8E. A spring loaded pawl 81 can push a gear 84 forward, at the completion of a stroke. The pawl 81 can push into a stop 82 while in air, or when advancing the gear 84. When the shuttle 56 is being retracted, the pawl 81 can be allowed to rotate to clear gear teeth. The gear 84 can be connected to a dial wheel 85, with an indicator arrow 86 outside the housing 62, in a location visible to the user. The user can determine the number of times the device has been actuated by looking at markings 87 on the side of the housing. An additional set of gear teeth and ratchet can be incorporated into shaft 83 to prevent the wheel from moving backwards inadvertently. In FIG. 8A the dial wheel 85 can be in such a position that the indicator 86 is pointing at 0, which indicates the device has not yet been cycled. A wide variety of markings with corresponding gear sizes are possible. FIGS. 8C-8E show cross-sectional views. The user may also be able to reset the dial by pressing the dial down to bypass the additional gear teeth and ratchet and manually spinning the wheel to zero or another desired location.

Figure 9:
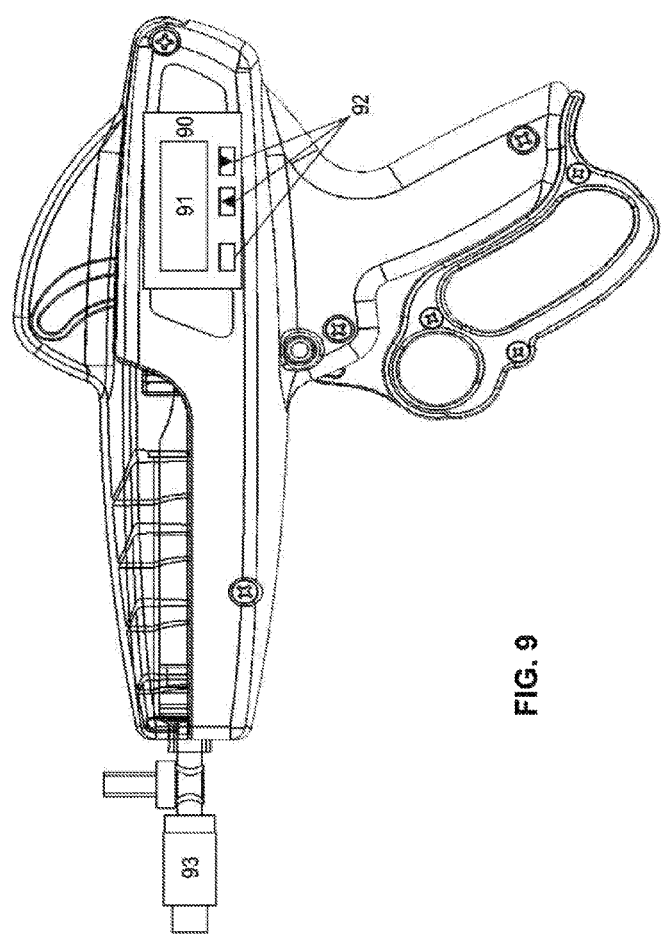
FIG. 9 is a view of a delivery mechanism of FIGS. 1-3, having an added pressure transducer and display according to embodiments of the invention.

FIG. 9 shows a display 90 integrated into the housing. The display 90 may show volume infused, number of a strokes completed, infusion pressure or other information to the user on a LCD screen, electronic ink, or other screen 91. Buttons 92 may allow the user to choose set points, change units, and or reset the values displayed on the screen. In this configuration a pressure transducer 93 is shown in communication with the patient side of the tubing and connected to the display 90. In some embodiments, a wired or wireless connection may be connected to this display 90 from an encoder tracking housing movement, or a processor calculating multiple parameters. In some embodiments, the housing may include an encoder in communication with the syringe, a processor in communication with the encoder. The processor may be configured to calculate a dispensed volume and provide the dispensed volume to the display 90. In some embodiments, the processor may be configured to direct the device to generate an alert with a defined amount of fluid has been dispensed. In some embodiment, the buttons 92 may allow the user to set a desired target dispensed volume amount. In some embodiments, a priming amount of liquid can be electronically decremented from the dispensed volume or the user reset input can direct the processor to calculate the dispensed volume after a priming operation.

Figure 10:
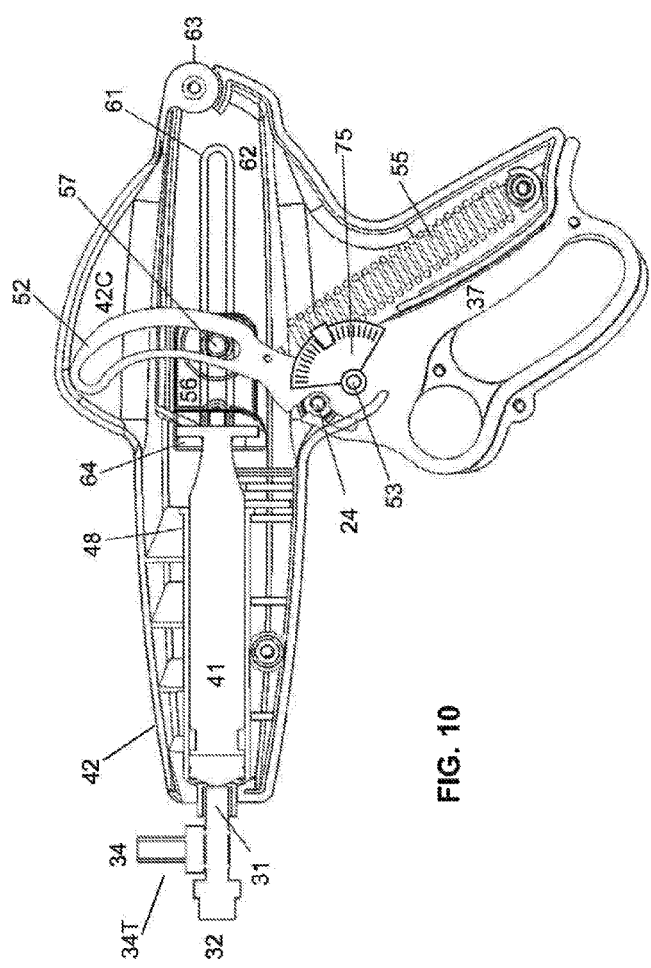
FIG. 10 is a view of the delivery mechanism of FIGS. 1-3, having and added an encoder linked to the trigger to be used to determine trigger position and optionally to calculate or confirm a volume of liquid infused according to embodiments of the invention.

FIG. 10 is a cross sectional view of a housing mechanism including a rotary encoder. In this embodiment, an optical encoder wheel 75 can be mounted to the trigger 37. The sensor can be mounted on the housing and may measure the location of the trigger 37, shuttle 56 and plunger 41 as they move together. A linear encoder attached to the shuttle can be another embodiment of this configuration. In this case the sensor can remain on the housing 62, but in a different location. Magnetic or other types of encoders can replace the optical encoders as alternate embodiments. The encoders can be connected electrically to a processor capable of calculating the total amount of travel, and can display that information to the user. The amount of travel can be used to calculate a volume of liquid infused. A zeroing button or other method of resetting the display can allow the user to start or stop the count at any point. Alternately the user may select a desired amount of fluid to infuse and the system may provide an auditory or visual alert when that level was reached, or nearly reached.

FIG. 11 depicts a system 600 with a powered (i.e., motor driven) injection mechanism. A motor 151 can actuate a series of gears, depicted as a rack 155 and pinion 154 in the embodiment shown, however a number of other gear combinations and configurations can be used, including a worm gear, a series of spur gears, planetary gears and/or bevel gears. The motor 151 is shown perpendicular to the motion of the shuttle travel, located in the grip 39. Other locations for the motor 151 can include being parallel to the motion of the shuttle, above or below the track. The motor 151 can also be located proximal to the shuttle, at the back of the housing, or in front. The rack 155 is attached to a shuttle mechanism 156. The shuttle mechanism 156 has a track 14 which holds the plunger 41 of the syringe 48, and allows for axial motion of the plunger 41. Multiple pins 157 can hold the shuttle mechanism 156 in position as the rack and pinion gears turn. The motor 151 may be either powered by a cable plugged into a standard outlet or a battery pack as depicted as 152. A trigger 37' can be an electronic control button or switch. The control button 37' can allow the user to control the flow of fluid. Additional buttons can be added if the user desires additional control inputs, such as pressure or volume targets or limits. A processor such as a CPU 158 can be used to control the actions of the motor 151, record performance, and/or modify performance based on additional inputs such as pressure transducers. An encoder or encoders can be integrated into the motor 151, to calculate the position of the shuttle mechanism 156 at all times. Alternately a linear encoder may be placed on the shuttle 156, with the sensor mounted on the housing 62. FIG. 12 depicts a closer view of the rack and pinion mechanism as shown from a rear view.

Figure 13A:
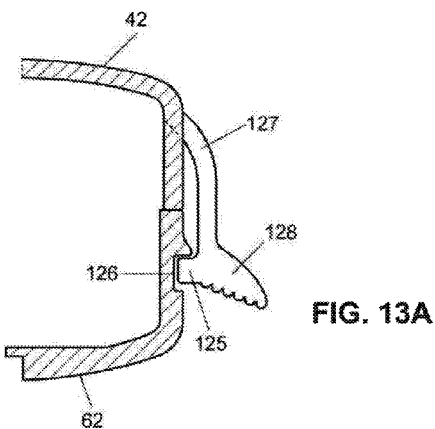
FIG. 13A is a cross-sectional view of a mechanism for locking the lid of the delivery mechanism of FIGS. 1-3 according to embodiments of the invention.
Figure 13B:
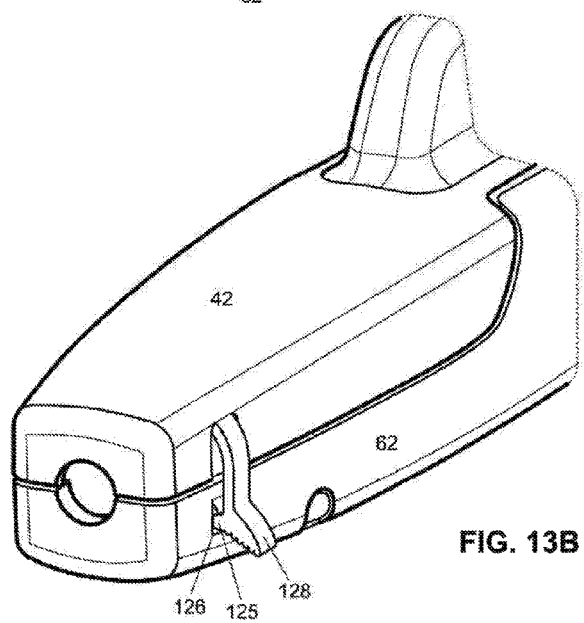
FIG. 13B is an isometric view of the locking mechanism of FIG. 13A according to embodiments of the invention.

In FIG. 13A, a cross section view is shown of the lid and a detent lever 127 to secure the lid 42 to the housing. A detent 125 on the lid 42 can have an interference fit with a groove on the housing 126. The length of the detent lever 127 and amount of interference with the housing can allow the force to be tuned to a low enough level appropriate for a user to open the lid 42 when desired, but remain high enough to keep the lid in place during normal use. Ledges 128 can allow the user to gain additional leverage when releasing the detent 125 from the housing 62. FIG. 13B is an isometric view of the same mechanism. The detent 125 can be on a single side of the housing 62, or on both sides.

Figure 14A:
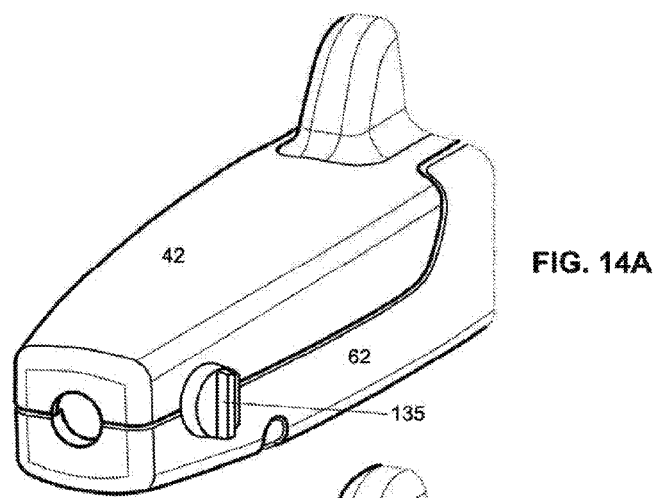
FIG. 14A is an isometric view of another locking mechanism for locking the lid of the delivery mechanism of FIGS. 1-3 according to embodiments of the invention.
Figure 14B:
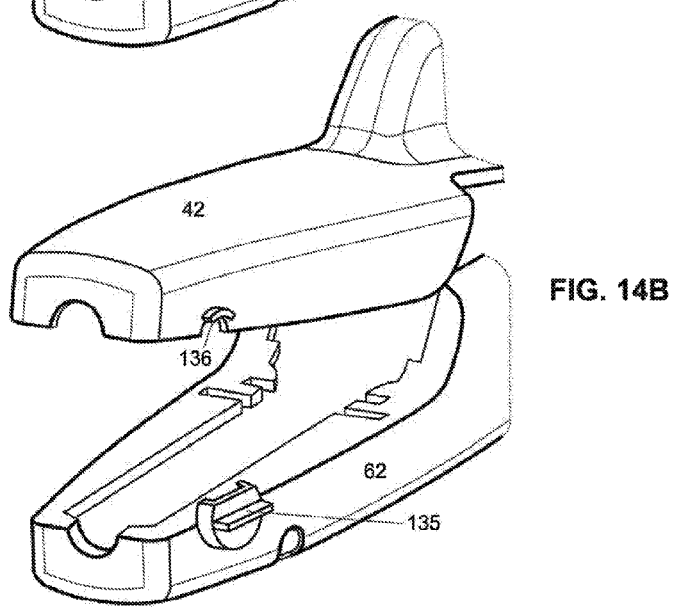
FIG. 14B is an isometric view of the locking mechanism of FIG. 14A unlocked and the lid of the delivery mechanism shown as open according to embodiments of the invention.

Alternately, other locks can be used, e.g., a two piece locking mechanism can allow the user to twist a knob to the "locked" position to hold the lid in place, and can be twisted to an "unlocked" position when the lid 42 can be released. FIG. 14A shows this mechanism with a lock knob 135 twisted into the locked position. FIG. 14B shows this mechanism with a lock knob 135 twisted into the unlocked position, and the lid 42 in an open position such that a syringe 48 may be loaded. Lock knob 135 can engage with lip 136 to hold the lid 42 in place. Additional features added to the housing 62 may limit the movement of the lock knob 135 such that the user may be able to find the unlocked and locked positions, and avoid over or under rotation. Magnets or other methods may also be used to secure the lid 42.

Figure 15:
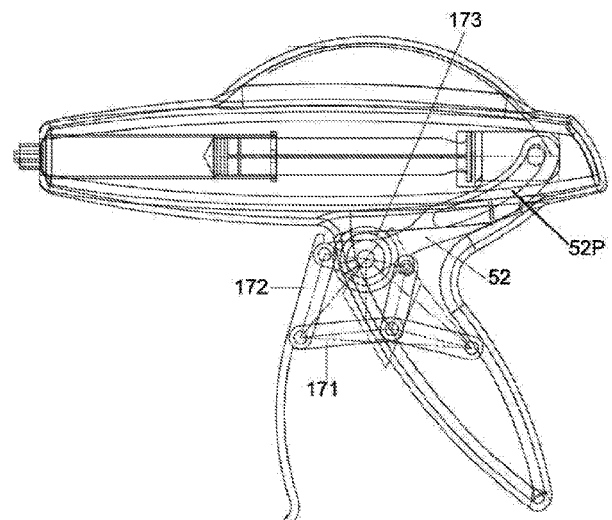
FIG. 15 is a cross-sectional view of a delivery mechanism having a four-bar advancement system shown in a retracted position of its shuttle mechanism ready for dispensing fluid from a syringe according to embodiments of the invention.
Figure 16:
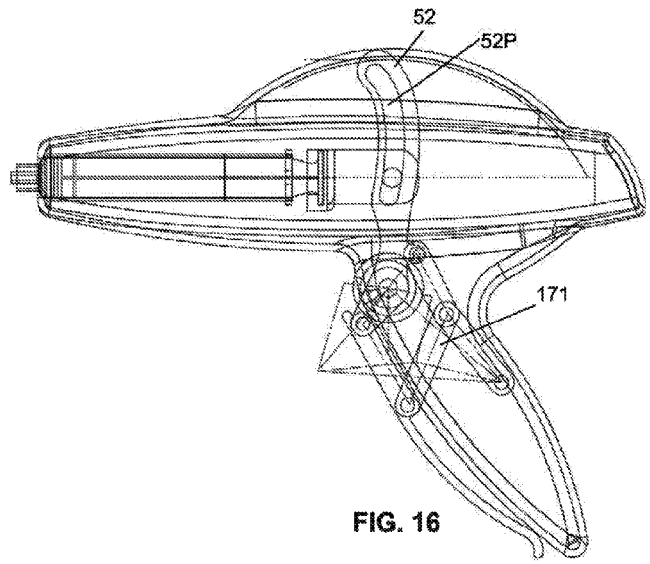
FIG. 16 is a cross-sectional view of the delivery mechanism of FIG. 15A, shown with the four-bar advancement system shown in its shuttle-advanced position after dispensing fluid from a syringe according to embodiments of the invention.

FIG. 15 depicts a mechanical system with a four bar linkage system. The actuation lever 172 can be connected to the lever 52 with a cam path 52P, and a cross link 171. Cross link 171 can be connected to a fixed pivot point and a second cross link. The cam path 52P can rotate about a second fixed point 173. FIG. 16 depicts the same system in a closed configuration.

Figure 17:
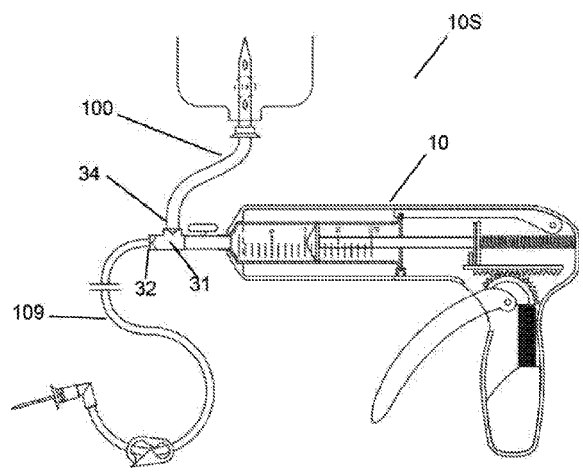
FIG. 17 is a cross-sectional view of a delivery system with tubing and fluid bag attached for use according to embodiments of the invention.
Figure 18:
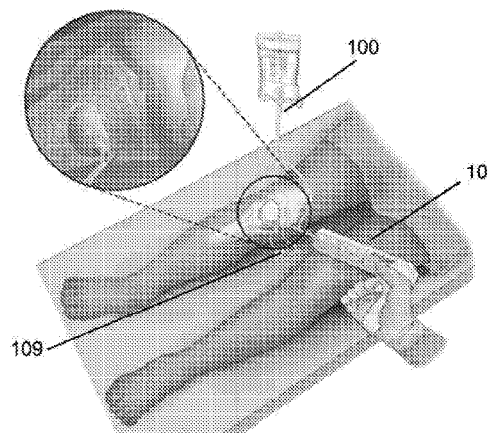
FIG. 18 is a view depicting the delivery system of FIG. 17 in use in a clinical environment according to embodiments of the invention.

FIGS. 17 and 18 depict a system in use in a clinical environment. The patient is shown lying on a table in FIG. 18. Tubing 100 can connected from a fluid bag to the patient, and the housing 62 is shown in the user's hand in FIG. 18. In this case the fluid is delivered through the patient's tibial plateau through an intraosseous port. A cross sectional view in FIG. 18 shows an illustration of the fluid perfusion through the trabecular bone of the tibial plateau. Other configurations for connections to the patient may include, but are not limited to, using the system to connect directly to a peripheral catheter. Additionally, the system can be used for wound irrigation or other methods where direct connection to the patient is not required. The system shown in FIGS. 17-18 generically represents any of the above described embodiments.

Figure 19A:
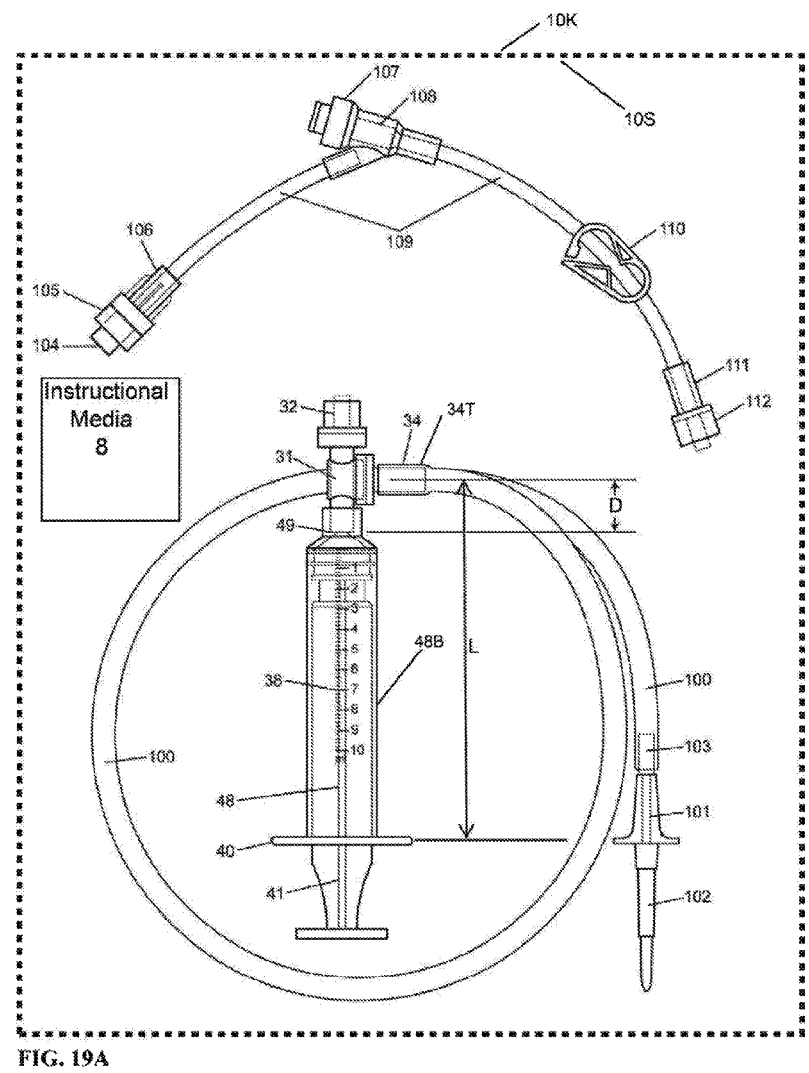
FIG. 19A is a top view of an example embodiment of a basic tubing set for an infusion device according to embodiments of the invention.
Figure 19B:
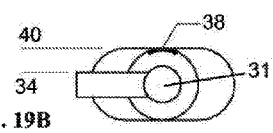
FIG. 19B is an enlarged end view of the inlet tube relative to the syringe valve according to embodiments of the invention.

FIG. 19A is a top view of an example embodiment of a basic tubing set 10S for an infusion device 10 according to embodiments of the invention. FIG. 19B is an enlarged front view of the inlet tube 34 relative to the syringe 48 valve. An exemplary tubing set 10S which includes a single-spike inlet tubing set 100 is described below. A 10 ml syringe 48 (or other sizes, such as 5 ml, 20 ml, or 30 ml, not shown) can be directly connected (e.g. pre-attached) to a dual check valve 31, comprising two valves, an inlet valve 34 and an output valve 32. The syringe 48 has a syringe body 48B, a plunger 41 and a flange 40. Large bore inlet tubing 100 with a length of about 2-12 feet can be attached directly to the inlet valve 34, typically about 5 feet. In some embodiments, for example, lesser lengths or greater lengths may be used. Examples of bore tubing 100 lengths include 2.5, 3, 3.5, 4, 4.5, 5, 5.5, 6, 6.5, 7, 7.5, 8, 8.5, 9, 9.5, 10, 10.5, 11, 11.5, 12 feet, or greater. In some embodiments, the ID of the large bore inlet tubing 100 can be about 3.5 mm, about 4 mm, about 4.5 mm, about 5 mm, or about 6 mm. In some particular embodiments, the ID is about 4.3 mm. The other end of the inlet tubing 100 can be attached to an inlet spike 102, which is compatible with standard IV fluid bags, among other containers, and includes a finger grip 101, and inlet spike connection 103. The output of the dual check valve 32 may be or comprise a male luer connection, which can allow connection to a multitude of currently available tubing. The inlet portion 34 of the dual check valve 31 can be lined up to be parallel with the indicia 38 on the syringe body 48. The indicia 38 may provide visual indicia of a volume of the syringe 48. In some embodiments, the visual indicia 38 of the volume of the syringe 48 may be a marking or other indicator in a graduated scale on an outer surface of the syringe 48. The alignment of the indicia may allow the housing 62 to orient the inlet tubing 100 and/or inlet valve 34 such that the indicia 38 may be visible to the operator during use, to allow precise control of the amount of fluid infused into the patient. The inlet tube 34T may be parallel and oriented to extend outward from either the right or left side. In the embodiment shown, the inlet tubing 100 is oriented to extend perpendicularly outward from the housing to the right. If the provider is standing on the right side of the patient and the fluid bag is near the patient's feet, this configuration can minimize clashing or looping of the inlet tubing 100 with the other activities being performed on the patient. Additional asymmetries may be present on the syringe body 48, the check valve 31, or tubing 100 to assist the user when aligning the syringe 48 into the housing 62. Without this alignment feature, it may be possible for the user to place the indicia 38 on the syringe 48 such that they are not visible during use. This may go unnoticed during set-up, and the user may be reluctant to disassemble the system in order to make the indicia 38 visible if set-up incorrectly. Because this may be a usability concern, and usability is typically a concern for both the FDA and the International Organization for Standardization (ISO) when getting clearance for the use of medical devices, facilitating and/or forcing proper alignment during insertion of the syringe 48 as part of the design can avoid/address this issue.

Precisely controlling the distance between the syringe body 48 and the inlet tube 34T with the inlet tubing 100 may allow for the housing 62 to encapsulate at least a sub-segment of the inlet tube 34T attached to the inlet tubing 100 and/or valve tube holding the inlet tubing, and prevent the assembly of the device in an incorrect orientation. In the configuration shown, the inlet tube 34T with the inlet tubing 100 can be at a distance D of between about 0.5 inches and about 0.9 inches from the end of the syringe. That is, an axially extending centerline of the inlet tube 34T can be a distance D of between about 0.5 inches and about 0.9 inches from the discharge end of the syringe 48 which is attached to the check valve 31. In some embodiments, the distance D is about 0.7 inches. Also shown in FIG. 19A, the inlet tube 34T with the inlet tubing 100 can be at a distance L of between about 2 inches and about 5 inches from the flange 40 of the syringe 48, typically between about 3.25 inches and 4.25 inches. That is, an axially extending centerline of the inlet tube 34T can be a distance L of between about 2 inches and about 5 inches from the flange 40 of the syringe 48. In some embodiments, the distance L is about 3.75 inches. This configuration may additionally prevent, inhibit or reduce rotation of the tubing 100 during use, which can allow the user to avoid the clashing or catching of the inlet tubing 100 while performing other tasks related to the resuscitation of the patient.

Figure 19C:
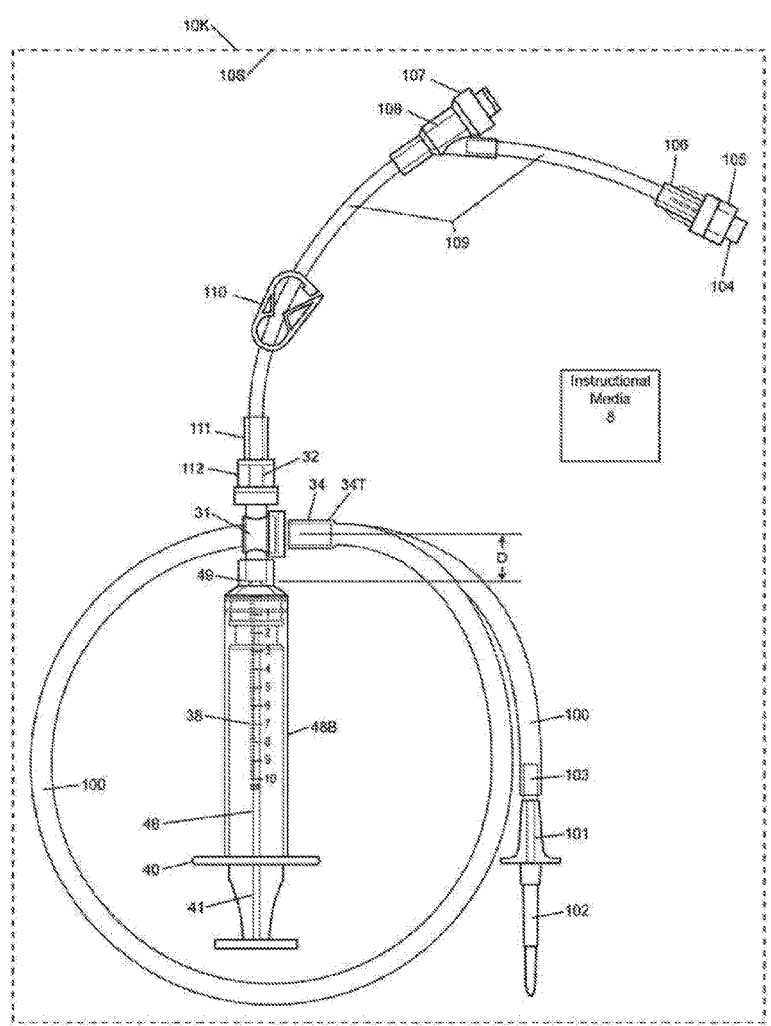
FIG. 19C is a top view of the tubing set of FIG. 19A illustrating connected adaptor tubing according to embodiments of the invention.

To facilitate easier connections to the IV or IO needle, a set of adaptor tubing 109 may be used. This set of adaptor tubing 109 may be about 6 inches to 12 inches in length, in the configuration shown here, although longer lengths may also be used. In order to allow the injection of other fluids beyond the fluid in the previously mentioned IV fluid bag, a second set of adaptor tubing 109 may also be pre-attached or provided separately to connect to the output port 32 of the dual check valve 31. The adaptor tubing can include a female luer connection 104, which may be a needleless female luer connection, connected via a tubing pocket connection 106 to small bore tubing 109. The female luer 104 may be connected directly to the output 32 of the check valve 31. The small bore tubing 109 may connect directly to a male luer 112, via another tubing pocket connection capable of withstanding high pressures. This male luer connection 112 can connect directly to an IV or IO placed into a patient. Alternatively, as shown in this figure, a Y connector 108 may be used. The Y connector 108 may contain a needleless female luer connection 107. The Y connector 108 can allow direct connection to a syringe containing other fluids which may be injected into the patient, or may also be used for a gravity feed IV line. FIG. 19C is a top view of the tubing set of FIG. 19A illustrating adaptor tubing 109 connected to the output 32 of the check valve 31.

One or more thumb clamps 110 may be present to stop the flow of fluid. If needed, the set of adaptor tubing 109 described above may be removed from the infusing tubing, and remain with the patient when transferring from an ambulance to a hospital, or other situations.

The tubing set 10S can be provided in a ready-to-use kit 10K. The kit 10K can include at least one package that holds the tubing set 10S in a sterile condition. The kit 10K can include instructional media 8. The instructional media 8 can be provided either electronically and/or in paper form that facilitates proper use, assembly, and/or training of the tubing set 10S. The media can include a suitably descriptive title and/or label identifying the content as instructions/training material for the tubing set 10S. Electronic instructional media 8 can include a video or electronic instructional manual that can be shown on a display. The instructional media 8 can be provided via the Internet such as at a hosted internet portal/site, via an APP for a smart phone, computer, electronic notebook or tablet and the like, typically via the use of an icon with defined functionality as is known to those of skill in the art. Paper instructional media 8 can include a paper user manual or booklet such as an instructional manual showing proper usage of the tubing set 10S.

Figure 19D:
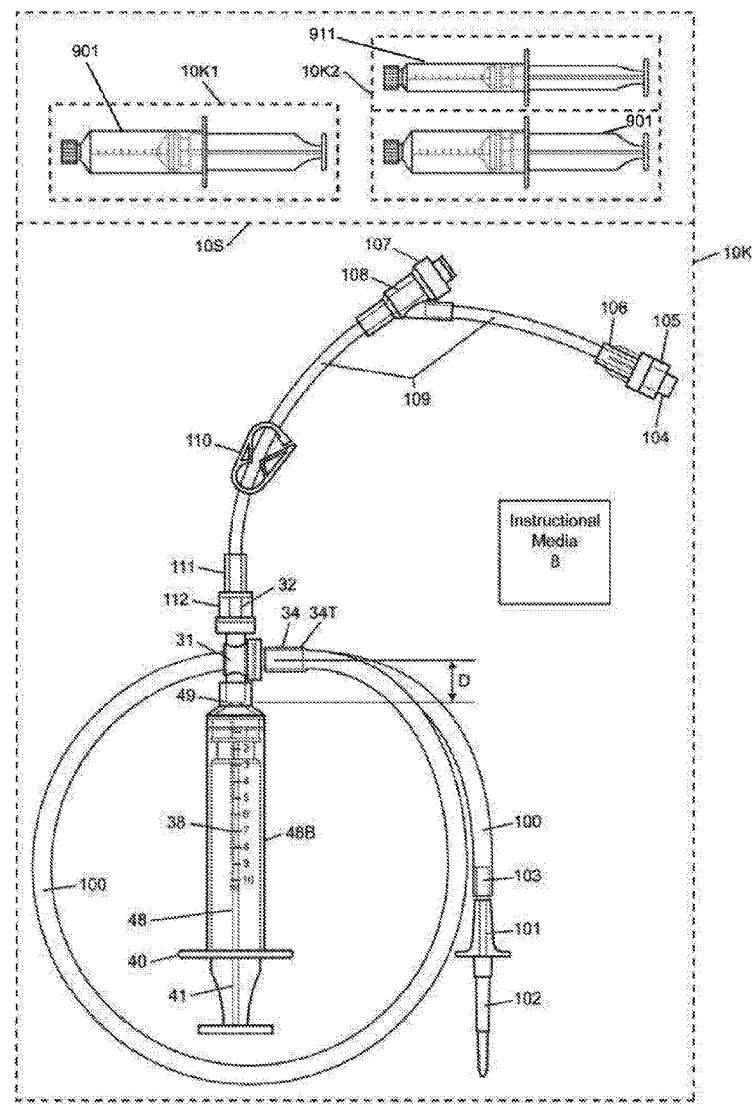
FIG. 19D is a top view of a set of components useful for treating a respective patient which can be provided in one or more packages according to embodiments of the invention.

FIG. 19D is a top view of a set of components useful for treating a respective patient which can be provided in one or more packages, typically in a single external package holding multiple internal sterile kit packages 10K1, 10K2. As shown, the set of components can include at least one pre-filled syringe 901, which can optionally comprise first and second separate pre-filled syringes 901,911 of different substances along with a tubing set having or attachable to the infusion syringe 48 according to embodiments of the invention. In some embodiments, the set of components can be provided as a kit 10K that can comprise a first sterile package which provides the tubing set 10S and at least one other (i.e., a second) sterile kit package with the at least one pre-filled syringe 901 and/or 911 comprising medication that can be administered to a respective patient with the tubing set 10S. The at least one pre-filled syringe 901 can comprise a local anesthetic. Where more than one pre-filled syringe 901, 911 is included, the second pre-filled syringe 911 can comprise a buffering agent that can be mixed in situ with the local anesthetic and delivered via outlet tubing of the tubing set 10S to a patient.

The pre-filled syringes 901, 911 may be provided in one package within a single kit 10K, or may be provided in separate packages which are external to, separate from, or attached to a package of the kit 10K holding the tubing set 10S. In some embodiments, the kit may comprise one sterile package (indicated by the broken line perimeter about the set of components) which includes both the syringes 901, 911 and the tubing set 10S. In some embodiments, the kit 10K may comprise a first sterile package 10K1 with the tubing set 10S and a separate second sterile package 10K2 with a pre-filled syringe 901 for local pain relief, optionally with the buffering agent pre-filled syringe 911 in the second package 10K2 or in a third package holding only the buffering agent syringe 911. One or more pre-filled syringes 901 can comprise lidocaine, or other local anesthetic, and may be packaged in a single kit package 10K1 along with the tubing set 10S. In some embodiments, the kit 10K can provide a kit package 10K1 for the tubing set 10S and a separate at least one kit package 10K2 containing one, or both, pre-filled syringes 901, 911, at least one of which is a pre-filled syringe 901 containing a local anesthetic, such as lidocaine, and at least one of which is a pre-filled syringe 911 containing a buffering agent, such as sodium bicarbonate.

Figure 20:
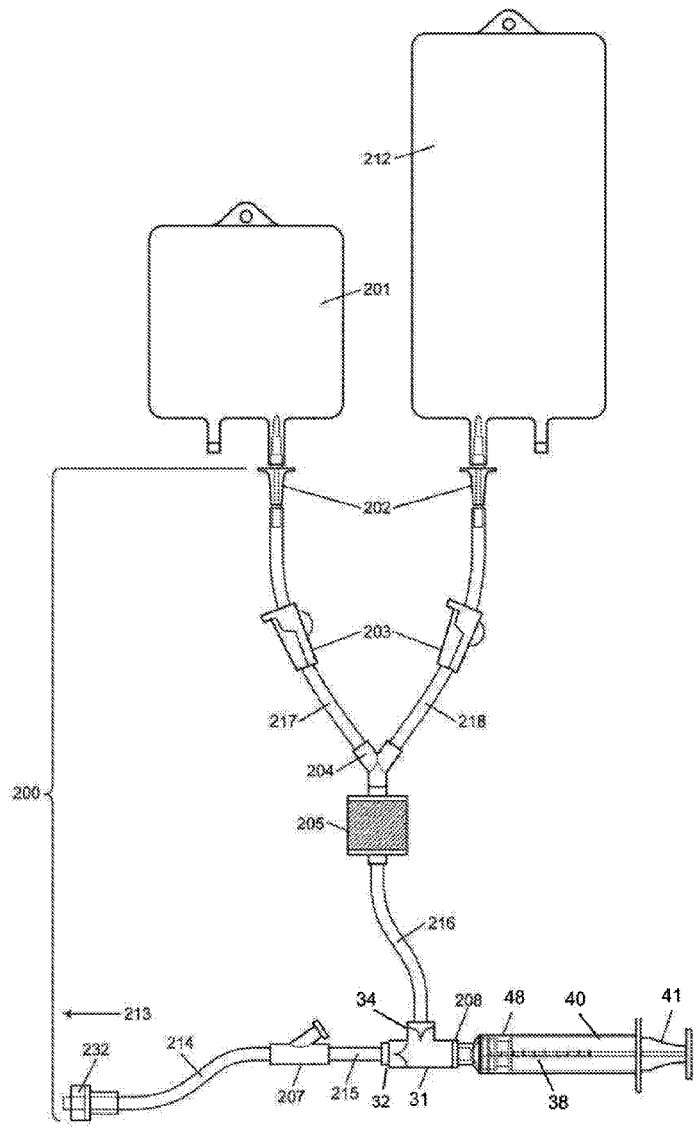
FIG. 20 is a schematic illustration of an example embodiment of saline and blood product administration tubing according to embodiments of the invention.

FIG. 20 is a schematic illustration of an example embodiment of saline and blood product administration tubing according to embodiments of the invention. When transferring blood into a patient, additional configurations of tubing sets 200 may be used. In the configuration shown, tubing set 200 is capable of transferring blood and blood products to a patient. Two inlet spikes 202 are connected to two fluid bags, 201 and 212. One bag 201 can contain blood or blood products, while a second bag 212 contains saline or other similar fluids. As used herein, blood products can include products derived from blood including platelets, plasma, plasma derivatives, cryoprecipitated antihemophilic factor, and red blood cells, though the present invention is not limited thereto. In order to selectively isolate each bag, two clamps 203 and 211 can be provided, one on each inlet line 217 and 218. These clamps 203, 211 may be roller clamps which can both limit and fully shut off the tubing, and/or a thumb clamp which can only be fully opened or fully closed. The inlet tubing 217 and 218 may be large bore tubing, typically about 4.3 mm inner diameter. The two inlet tubes 217, 218 may be joined at a Y connection 204, which may be configured to have reduced or no restrictions to flow. The fluid may then pass through a filter 205 and may continue through a common inlet tube 216 to the dual check valve 31. In the configuration shown, a large bore connection 208 with little or no narrowing (e.g., a constant inner diameter connection) may be present between the dual check valve 31 and the syringe 48. The fluid can exit the outlet 215, which is a male luer connection. This connection may be connected to adaptor tubing 109 (FIG. 19A) previously described.

This tubing 216 can be primed with saline by connecting one inlet spike 202 to a bag of saline 212 or similar fluid, and opening all clamps and allowing fluid to flow through the entire system, using both gravity and cycling the syringe plunger 41. After the system is (fully) primed, the second inlet spike 202 can be placed into a bag containing blood products 201. The user can then select either the blood or, for example, saline to infuse, and open the appropriate clamp, 203 or 211. If roller clamps 203 are used, the user may set the clamps such that a tunable mixture of both blood and, for example, saline is pulled into the inlet tubing 216. Once the bag of blood products 201 is fully emptied the bag of saline or other fluid 212 may be used to flush the remaining blood products present in the tubing 216. A new bag of blood 201 and/or saline or other similar fluid may be attached to the system via a sterile technique, if desired by the user.

Figure 21:
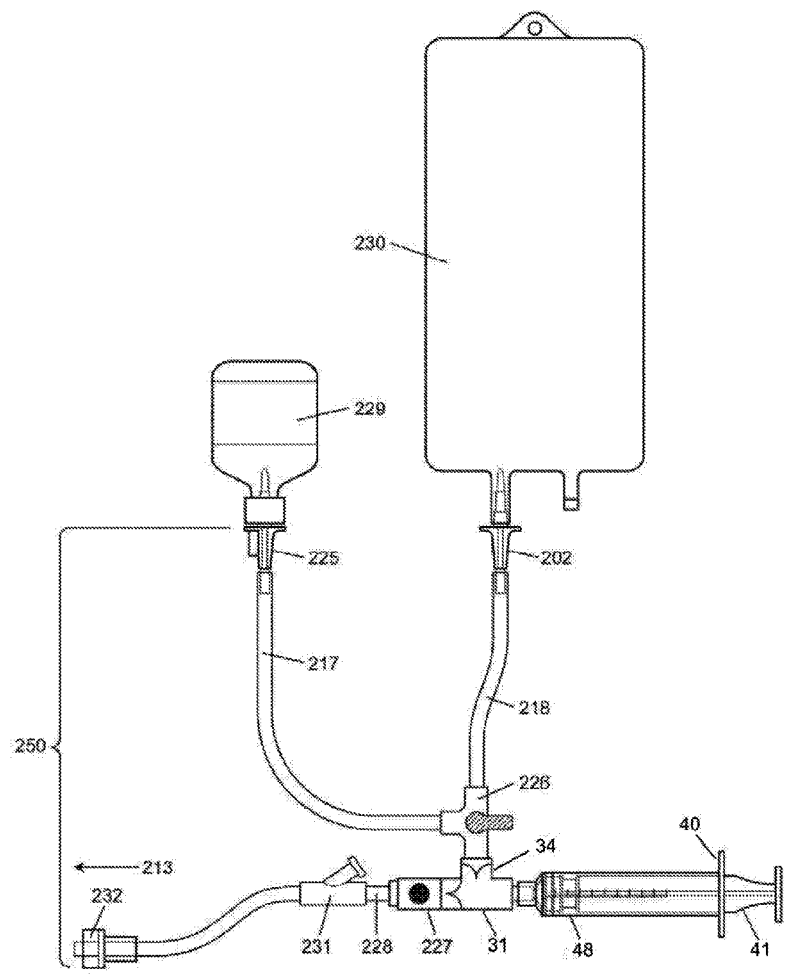
FIG. 21 is a schematic illustration of an example embodiment of saline and contrast media tubing according to embodiments of the invention.

FIG. 21 is a schematic illustration of an example embodiment of saline and contrast media tubing according to embodiments of the invention. A manually-activated syringe 48 with a connection for saline and contrast media can be used in interventional cardiology procedures to administer contrast media when performing heart surgery through the use of catheters. In this embodiment, contrast tubing 250 can include two large bore inlet tubes 217 and 218. In another embodiment, inlet tube 217 may be small bore tubing. Inlet tube 217 can be connected to a container of contrast media 229 via a vented spike 225. Contrast media is typically provided in hard glass bottles of about 150 ml. A second inlet spike 202 can connect to a fluid bag filled with saline or other products 230. The two inlet tubes 217,218 can connect at a two way selector valve 226. This two-way selector valve 226 can allow the user to select between the two different fluids when infusing into the patient. In some embodiments, the two-way selector valve 226 can reside to the side of the dual check valve 31. In some embodiments, the two-way selector valve 226 can be present on the side of the housing 62, within closer reach of the actuation mechanism (e.g. trigger 37, FIG. 22) on the housing 62. This configuration can have a further length of inlet tubing which can fluidly couple the two-way selector valve 226 to the dual check valve 31. The dual check valve 31 can be connected to a syringe 48, which can be between 30 ml and 5 ml in size. At the exit of the dual check valve 31 a pressure transducer 227 can be present to measure the pressure of the fluid. Smaller diameter (smaller than the inlet tubing) exit tubing 228 can transfer the fluid to a needleless Y valve 231, and then to a male luer connection 232. The male luer connection 232 can be used to connect to a cardiac catheter.

Figure 22:
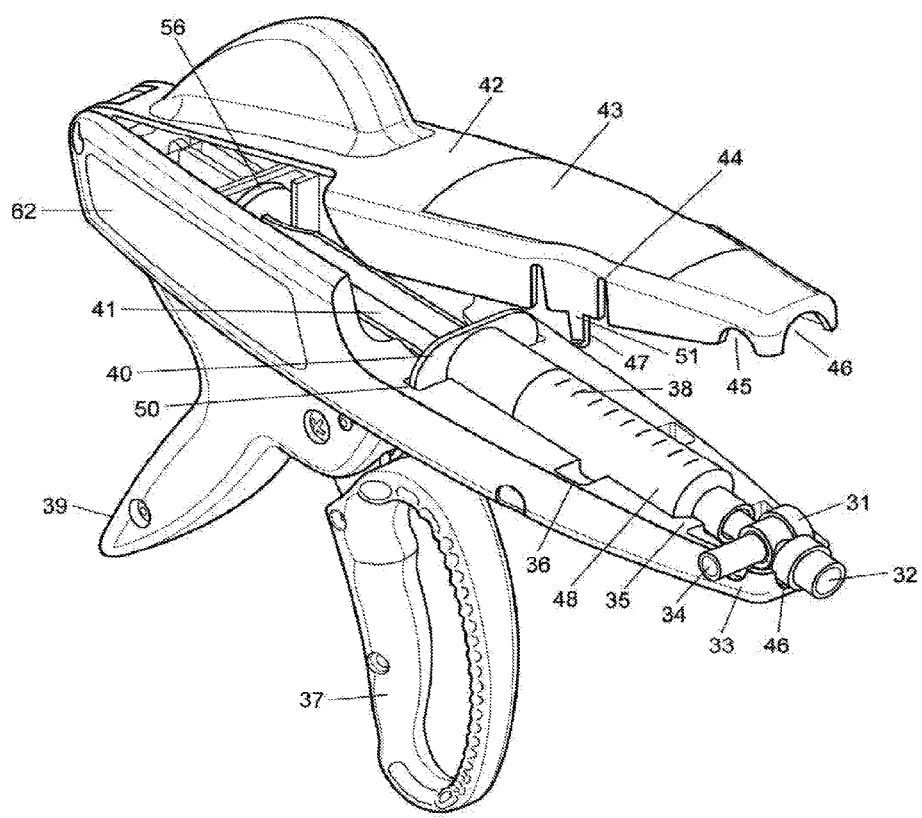
FIG. 22 is a side perspective view of an example embodiment of an infusion device according to embodiments of the invention.

FIG. 22 is a side perspective view of an example embodiment of an infusion device according to embodiments of the invention. The inlet portion 34 of the dual check valve 31 can be lined up to be parallel with the volume indicia 38 on the syringe body 48. This alignment allows the housing 62 to orient the tubing set such that the volume indicia 38 is visible to the operator during use, to allow precise control of the amount of fluid infused into the patient. The inlet portion 34 may be oriented to extend out of either the right or left side. In the configuration shown, the inlet tubing is oriented to the right. The syringe 48 fits in slots in the housing 62, with the plunger 41 captured in the shuttle 56. Additional asymmetries may be present on the syringe body 48, the dual check valve 31, or tubing to assist the user when aligning the syringe 48 into the housing 62. Without this alignment feature, it may be possible for the user to place the volume indicia 38 on the syringe 48 such that the volume indicia 38 are not visible during use. As noted above, this may go unnoticed during set-up, and the user may be reluctant to disassemble the system in order to make the indicia 38 visible. Because this is a usability concern, and usability is typically a concern for both the FDA and ISO when getting clearance for the use of medical devices, facilitating or forcing proper alignment during insertion of the syringe 48 as part of the design can address this issue.

In some embodiments, precisely controlling the distance between the syringe body 48 and the inlet tube 34T with the inlet tubing 100 can allow for the housing 62 to encapsulate at least a sub-segment or portion of the inlet tube 34T with the inlet tubing 100, and can inhibit or prevent the assembly of the device from resulting in an incorrect orientation. In the configuration shown, the inlet tube 34T with the tubing 100 is at a distance of between inches and 0.9 inches from the end of the syringe 48. This configuration can also inhibit or prevent rotation of the tubing during use which allows the user to avoid clashing or catching of the inlet tubing 100 while performing other tasks related to the resuscitation of the patient.

FIG. 22 shows the check valve 31 of the tubing set 10S loaded within the housing 62, and the lid 42 open. A dual check valve assembly 31 with an inlet 34 and outlet 32 is connected to a syringe 48. The connection between the syringe 48 and check valve 31 may be a male/female luer connection, or it may be a large bore custom connection. The inlet 34 is aligned to be parallel with the flange 40 of the syringe 48, and positioned such that the volume indicia 38 are visible when viewed from above, and the inlet tubing 100 extends out to the right. Alternate configurations include having the inlet tubing 100 extending out to the left, or at the bottom of the housing 162. There can be specific cutouts 33, 46 in the housing 62 to receive the syringe 48 and check valve 31. One housing cutout 33 (to be clear "cutout" refers to an aperture or access opening) in the sidewall can encircle inlet tubing 34, a second cutout 46 in the tip can reside about outlet 32. The cutouts can be entirely in the lower housing 162, entirely in the lid 42, or provided as pairs of cutouts in the lid 42 and lower housing 162 that face each other. The sidewall aperture for the inlet tube 34T can be circular (typically semi-circular in the upper and lower housing members) and can be on a right and/or left side. In some embodiments, the apertures can be other shapes, such as, for example, rectangular, triangular, oval, and the like. The sidewall aperture can be larger or smaller than the tip aperture for outlet 32.

There can be corresponding cutouts 45, 46 in the lid 42 which, together with the lower housing 162 cutouts, can completely encircle the inlet tube 34T and the valve outlet 32, and can ensure the desired orientation of the inlet tubing 100, indicia 38 and syringe 48 when assembled. There can be additional features in both the lower housing 162 and lid 42 to receive and secure the syringe 48. A slot 50 in the housing 62, typically the lower housing 162, can receive the flange 40. A circular cutout 35 can be sized and configured to receive the connection between the check valve body 31 and syringe 48. There can be corresponding cutouts in the lid 42 to receive these two features as well. As shown, the lid 42 can have latch features 47 which secure the lid 42 to the housing 62 via latch points 36. When latched, the lid 42 can hold the syringe 48 securely in place in one orientation, and also can protect and orient the check valve 31. The lid can prevent rotation of the syringe 48 by trapping the flange 40. The latch 47 can be released by a user when desired by squeezing the two latch extensions 51 simultaneously, allowing the latch 47 to release the corresponding latch points 36. The latch extensions 51 can be visually evident to the user by one or more features. Shown in FIG. 22 is a scalloped cut in the lid 42 at the location of the latch extension 51, and two downwardly extending slots 44. The slots 44 can serve a second purpose, to reduce the bending force required to release the latches. The lid 42, can be visually transmissive, typically transparent, and may have a highly polished window 43 which may allow easy visualization of the syringe 48 and its contents during use. The syringe 48 can be activated by moving a trigger 37, while holding a grip 39. The trigger 37 can be connected via a cam path 52P to a shuttle 56, which can actuate the plunger 41.

Figure 23C:
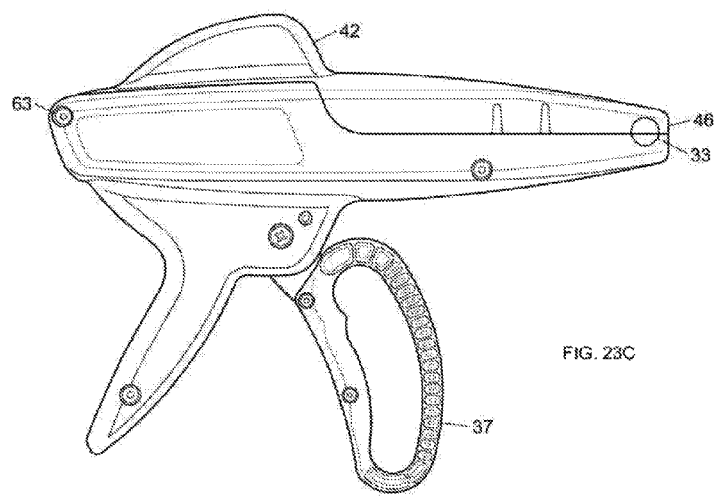
FIG. 23C is a side view of an example embodiment of a housing without an attached tubing set according to embodiments of the invention.

FIG. 23A is a top view of an example embodiment of a housing 62 without a lid 42 according to embodiments of the invention. FIG. 23B is a bottom view of an example embodiment of the lid 42 of the housing 62. FIG. 23C is a side view of an example embodiment of a housing 62 without an attached tubing set. These illustrations show the features that interact with and restrain the syringe 48, check valve 31, and inlet tubing 100 during use. As shown in FIG. 23A, the receiving slot 50 for the syringe flange 40 can be seen in the housing 62. Support ribs 193 located on the lid 42 can also serve to locate and restrain the syringe flange 40. Flats present on both the receiving slot 50 and support ribs 193 serve to prevent rotation of the syringe flange 40. Adjacent to this slot 50 is a circular recess 48C for the body of the syringe 48. Latch points 36 can also be seen in this view, as well as the cutout 35 that receives the syringe tip. A chamber 31C surrounds the dual check valve 31 and can provide protection and orientation guidance. This chamber 31C can have three exits, syringe neck or tip cutout 35, inlet cutout 33 and exit cutout 46, which can allow the syringe tip, dual check valve inlet 34 and dual check valve outlet 32 to pass through. A midline of the inlet cutout 33 may be a distance L from the receiving slot 50. In some embodiments, the distance L may be between about 2 and about 5 inches, typically between about 3.25 inches and 4.25 inches. In some embodiments, L is 3.75 inches. Some or all of same features can be located on the lid 42 as well. Shuttle 56 can move back and forth to move the syringe plunger 41 during use. The syringe plunger 41 can fit into receiving slot 64, and the shuttle 56 may be moved by the lever 52, which can transfer movement from the user's hand. A cam path 52P on the lever 52 can transfer force through a glide pin bushing 190B, into a glide pin 190, and then into the shuttle 56. A fixed pivot 63 can allow for rotation of the lid 42 through a pivot point 63P.

In this embodiment, syringe tip cutout 35, receiving slot 50, and the support ribs 193 are the main points of contact which can mechanically restrain the tubing set 10S during use.

Figure 24:
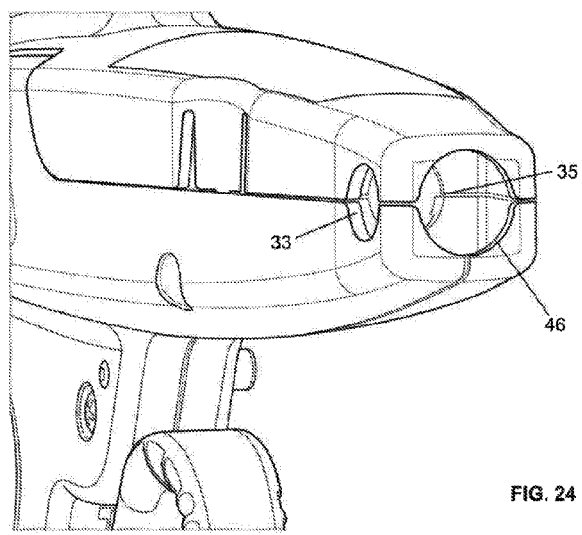
FIG. 24 is an oblique front view of an example embodiment of a housing and lid according to embodiments of the invention.

FIG. 24 is an oblique front view of an example embodiment of a housing and lid according to embodiments of the invention. In this oblique isometric view the opening for the inlet valve 33, opening for dual check valve exit 46 and cutout 35 for syringe tip are visible from a different angle, without the tubing present.

Figure 25:
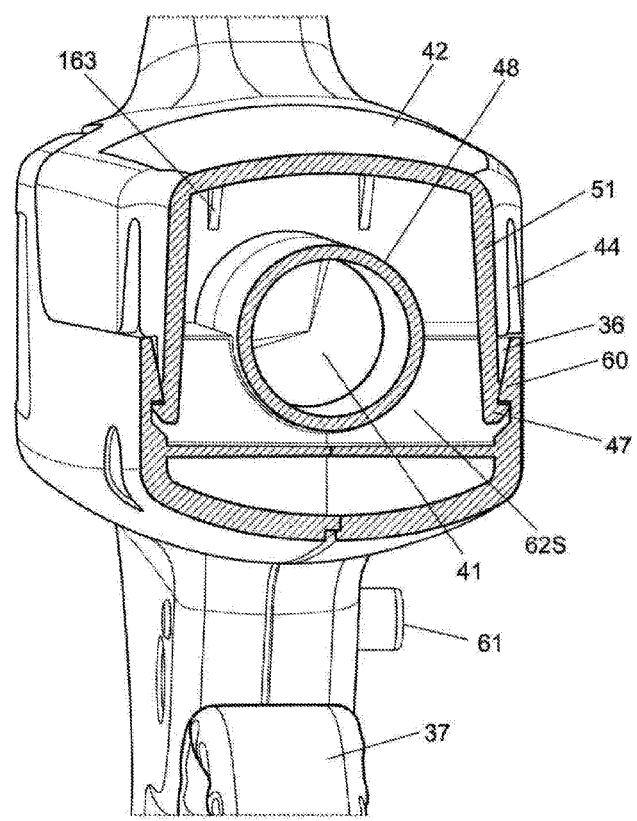
FIG. 25 is a cross-sectional view of an example embodiment of a housing illustrating a latching mechanism according to embodiments of the invention.

FIG. 25 is a cross-sectional view of an example embodiment of a housing illustrating a latching mechanism according to embodiments of the invention. The lid latch 47 can overlap engagement catch 60 such that a vertical force or side force will not inadvertently open the lid 42. Latch extensions 51 can allow users to press on the sides of the latches to release. Side slots 44 may be used to decrease the force required to release the latch 47. The tabs 163 which can hold the syringe flange 40 in place can also be seen in this view. The plunger 41 of the syringe 48 is also visible in the view. These can be supported by a support rib 62S in the housing 62. A side view of the pin lock 61 is also visible.

Figure 26A:
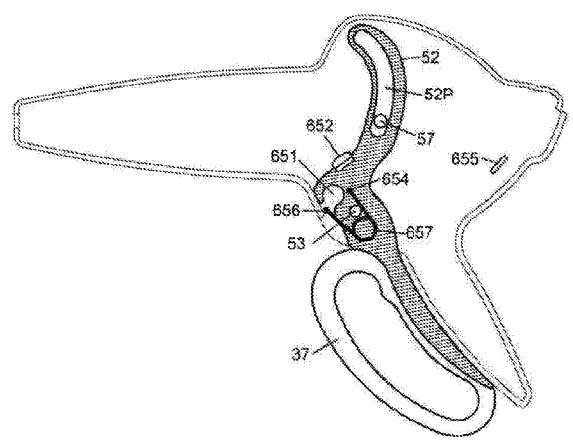
FIG. 26A is a schematic illustration of an infusion housing with a torsion spring and travel stop indicators of the housing according to embodiments of the invention.
Figure 26B:
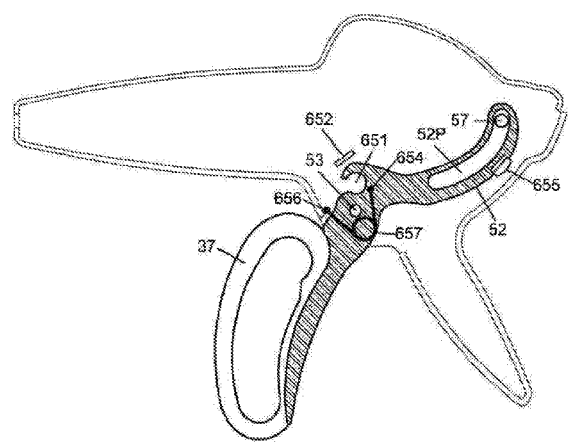
FIG. 26B is a side view of the infusion device shown in FIG. 26A according to embodiments of the invention.

FIGS. 26A and 26B show side views with an embodiment containing a torsion spring 157 instead of an extension spring. FIG. 26B is another side view of the torsion spring 657 and travel stop indicators of the housing 62. As shown, the torsion spring 657 can have one anchor point 654 on the lever 52, and another point on the handle 656. The central loop of the torsion spring 657 is shown outside of the trigger pivot 53, but it may also be centered around the trigger pivot 53. It may also be useful for the user to get audible and/or tactile feedback when the trigger 37 reaches full open and full closed position. There are multiple ways to accomplish this. An embodiment illustrated in these figures is the use of small tabs 655, 652 which can interfere with the actuation trigger. The rectangular tabs can be stiff, but can allow buckling at a certain amount of deflection, this buckling can provide both an audible and tactile feedback. One tab can indicate full open 655 or full closed positions 652, or any other desired position within the range of travel of the actuation trigger 37. Other detent designs or alternatives may also be used to indicate these positions. Two configurations are shown in these figures: full open (FIG. 26B) and full closed (FIG. 26A). In the full open position, the full open tab 655 is shown in the deflected state, and the torsion spring 657 is shown in the fully compressed state. In the full closed position, the full closed detent 652 is shown deflected and the torsion spring 657 is partially compressed.

In some embodiments, a cutout 651 for a lock, such as lock 24 illustrated in FIG. 1, can facilitate locking of the actuation trigger 37.

Figure 27A:
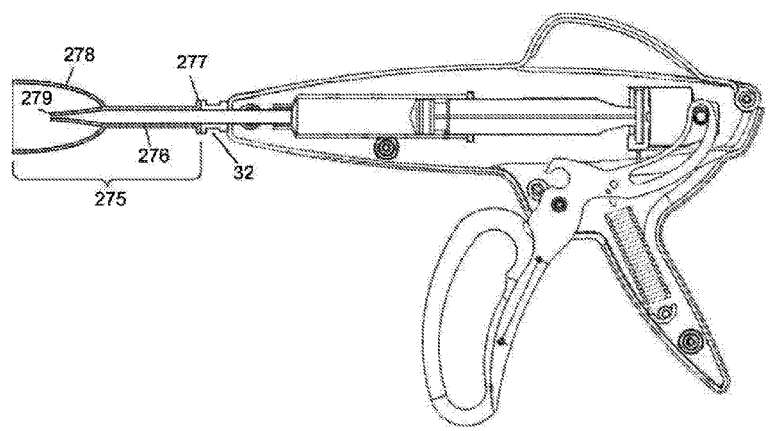
FIG. 27A is a schematic illustration of an example embodiment of a pulse lavage extension according to embodiments of the invention.
Figure 27B:
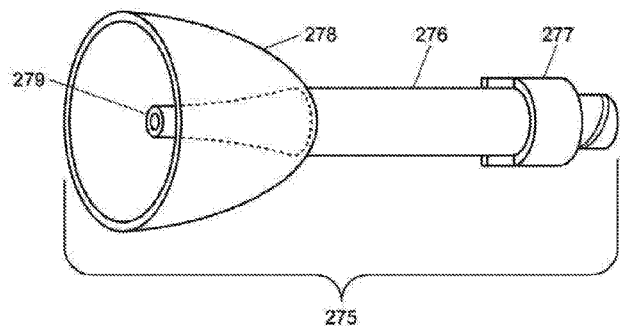
FIG. 27B is a schematic illustration of an example embodiment of the pulse lavage extension illustrated in FIG. 27A.

FIG. 27A is a schematic illustration of an example embodiment of a pulse lavage extension according to embodiments of the invention. FIG. 27B is a schematic illustration of an example embodiment of the pulse lavage extension illustrated in FIG. 27A. A pulse lavage system 275 may be attached to an IV bag and can be actuated by the dispenser housing 62. A female luer connection 277 can be compatible with the dual check valve outlet port 32. This can be connected by either flexible or rigid extension tubing 276 to fluidly couple the dual check valve 31 to the exit nozzle 279. The exit nozzle 279 includes a gradually narrowing opening configured to accelerate fluid to a high velocity at exit, to assist with lavage of tissue. The shape of this exit nozzle 279 may be a simple circular opening or an oblong oval shape, depending on user desire. A protective nose cone 278 can prevent splash back from exiting the target area. The handle of the device can be squeezed, which can force water or other sterile fluid through the exit nozzle 279, resulting in a high pressure flow. The high pressure flow can be directed at a wound requiring debridement. The trigger 37, 37' can be repeatedly cycled to refill automatically through the attached IV bag, connected to the inlet tubing via a spike (not shown).

Figure 28:
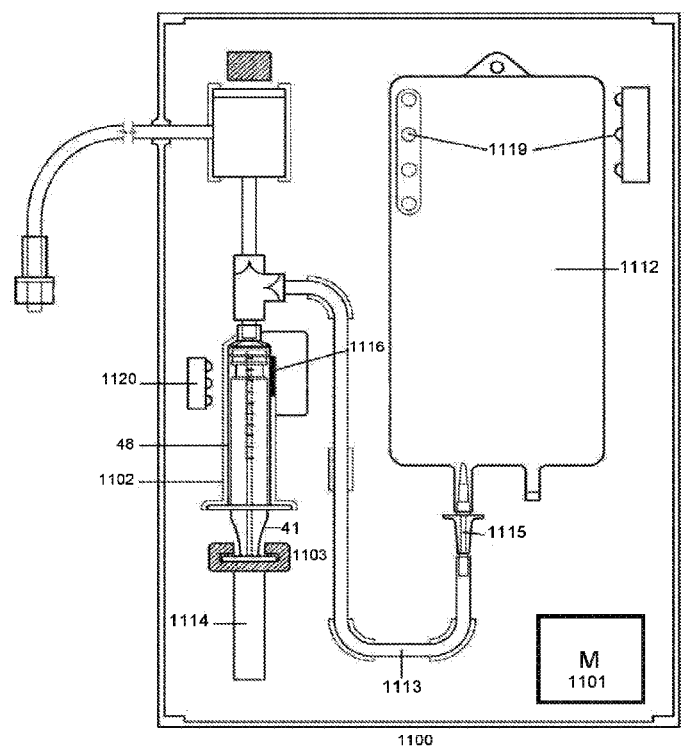
FIG. 28 is a schematic illustration of an example embodiment of an automated pump schematic according to embodiments of the invention.

FIG. 28 is a schematic illustration of an example embodiment of an automated pump schematic according to embodiments of the invention.

Other embodiments contemplate a motorized version of the infusion system 1100, utilizing a syringe 48 and tubing 100, but the plunger 41 is moved linearly by the action of a motor rather than manually. In some embodiments, the tubing set may be identical to the previously disclosed tubing set 10S (FIG. 19A), having an inlet spike 102, large bore tubing 100 about 5 feet in length, a dual check valve 31 and a syringe 48 (e.g., having a volume between 5 ml to 30 ml), which may or may not be connected to extension tubing. In some embodiments, the tubing set may have much shorter inlet tubing 1113 (0.5 feet-3 feet) and the inlet tubing may be large bore, or may be traditional smaller bore tubing. In other embodiments, two bags of fluid may be connected to a single syringe pump, with a Y joint and clamps to selectively control which bag provides fluid at any one time.

A motor pack 1101 may be used to actuate the plunger 41 on the syringe 48. The motorized system 1100 can have a slot 1102 for retaining the syringe 48, and an asymmetric orientation to ensure the tubing is properly oriented when placing for use. The syringe 48 can be held in a vertical position to facilitate the elimination of air bubbles while the system is being primed. The syringe 48 can be actuated by a motor linked by gears to create linear motion of the plunger 41. The motor output can drive an actuator 1103 up and down an actuator track 1114. The motor output may be controlled with several different control methods. In one embodiment the motor can be displacement controlled such that the motor torque output can be adjusted continuously to achieve a known fluid delivery rate. In another embodiment the motor may be current controlled such that it applies a known torque which generates a constant vacuum pressure and constant output pressure. In this case, the fluid infusion rate can vary, but the user can know that fluid is being infused at a known pressure, and can know if the line is blocked or not placed properly in the patient. It may also be possible to vary the torque applied so that the vacuum pressure created by motor retracting the syringe 48 can be at a different set point than the output pressure, created by the motor advancing the syringe 48. It may be advantageous to allow user selection of the desired output pressure, while maintaining a single vacuum pressure for maximum refill rate.

When using the motorized device the user can insert the inlet spike 1115 into a bag of fluid 1112 (saline, blood products, or other necessary fluid). The syringe 48 can be placed into the slot 1102 on the motorized system 1100. In one embodiment, the bag 1112 can be placed with the outlets pointing down in a traditional manner. In another embodiment, the bag of fluid 1112 can be placed with the spike 1115 facing upwards in the motorized system 1100, which can allow the user to purge the air from the system while all components were secured into the system. The system may have a sensor which detects the presence of a syringe 48 loaded into the slot 1102. They system may also have an RFID 1116, barcode, or other information on the body of the syringe which can provide information to the motorized system 1100 about the type of tubing inserted. The lid, lids, or other retaining features, can be closed to secure the fluid bag 1112 and the syringe 48. The lid, lids or other retaining features can have sensors which detect the proper closure of the system. Once the system detects that a certain tubing set has been properly secured, lights 1119 can illuminate the fluid bag 1112 to assist in the visual identification of any air bubbles present in the bag. A "purge" button may be depressed, which can cycle the plunger 41 at a slow and low torque until the user determined that all air had been removed from the fluid bag 1112, and the user can then release the purge button. Lights 1120 can then illuminate the vertical syringe 48. The user can again depress the purge button 1131 until all air bubbles are eliminated from the syringe 48 and any attached tubing. The tubing can then be connected to the patient, and infusion can begin.

In some embodiments, the fluid bags 1112 may be hung outside the motorized system 1100, and the entire unit placed on a stand near the patient, or hung from an IV pole near the patient.

Figure 29:
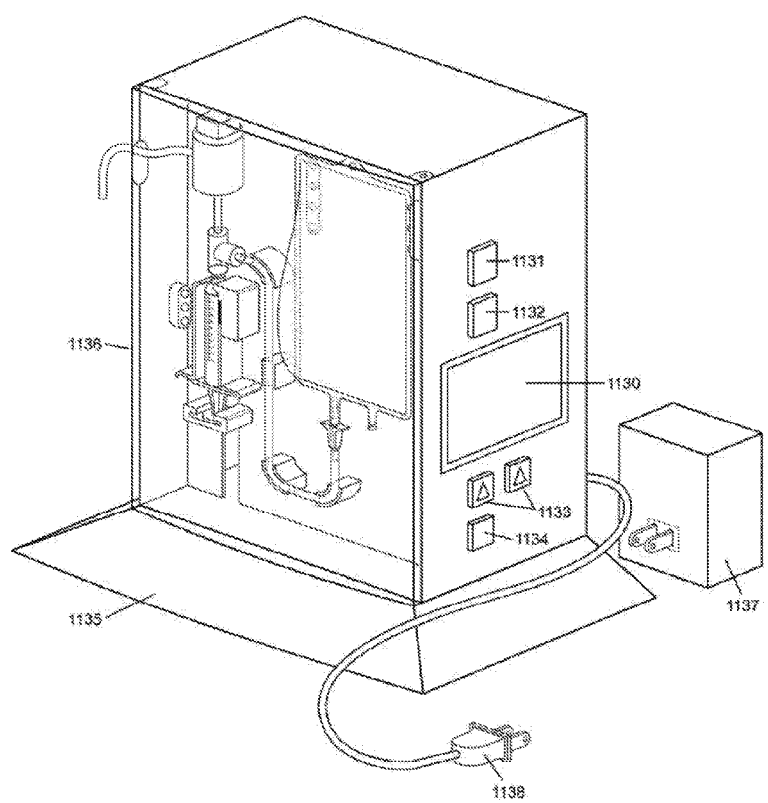
FIG. 29 is a schematic illustration of an example embodiment of a motorized enclosure with an internal fluid bag according to embodiments of the invention.
Figure 30:
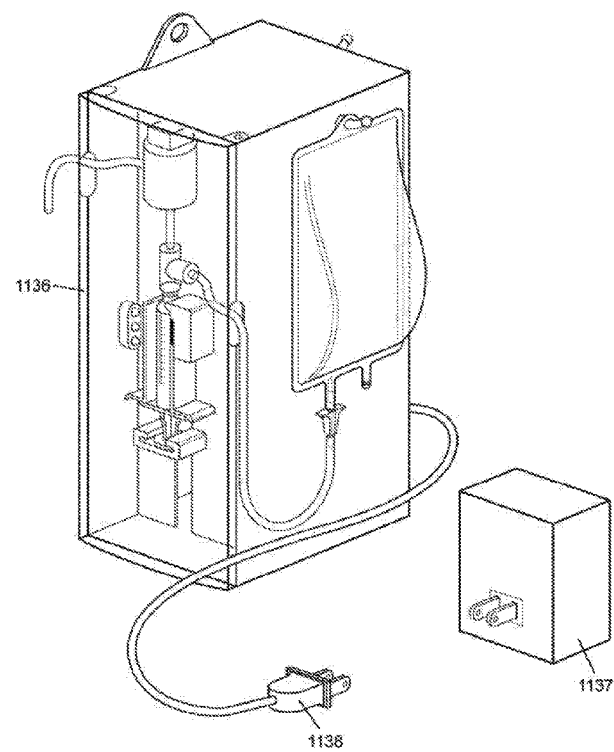
FIG. 30 is a schematic illustration of an example embodiment of a motorized enclosure with an external fluid bag according to embodiments of the invention.

FIG. 29 is a schematic illustration of an example embodiment of a motorized enclosure with an internal fluid bag according to embodiments of the invention. FIG. 30 is a schematic illustration of an example embodiment of a motorized enclosure with an external fluid bag according to embodiments of the invention.

In one embodiment, the user may select a known infusion rate, and/or a known infusion volume in the input screen 1130, and press the "infuse" button 1132. In another embodiment, the user can manually hold the infuse button 1132 down in order to keep fluid flowing.

In some embodiments, a user may manually select a desired input pressure and total infusion volume in the input screen 1130 and press the infuse button 1132. In a fourth embodiment, the user may select the type of access present on the patient, such as IV, IO, central line, and then select the size of the appropriate access type (i.e. IV—20 gauge, or Central line—4 French). In this case, the computer (e.g., at least one processor) can select an appropriate input pressure based on preprogrammed set points which correspond to each access type. While the system is infusing a display screen 1130 may indicate one or more of the following: total fluid infused, current infusion pressure, current infusion rate, average infusion rate, patient access type and size selected, tubing type present in system, among other pertinent information.

Other embodiments may include the use of a counter that automatically tracks the amount of fluid infused and operates with a "setpoint" 1133 that provides an audible and visual alarm when the desired setpoint is reached. A "reset" button 1134 may also be used to re-zero the counter, if some fluid was used for priming or other purposes that did not reach the patient. A display 1130 showing the setpoint and current amount infused, next to a set of up/down buttons for the setpoint 1133 and a reset button 1134, can provide this functionality.

In some embodiments, a motorized enclosure can receive power from a battery pack 1137 and/or a power connector 1138. The enclosure may include a stand 1135 and/or a cover 1136.

Figure 31:
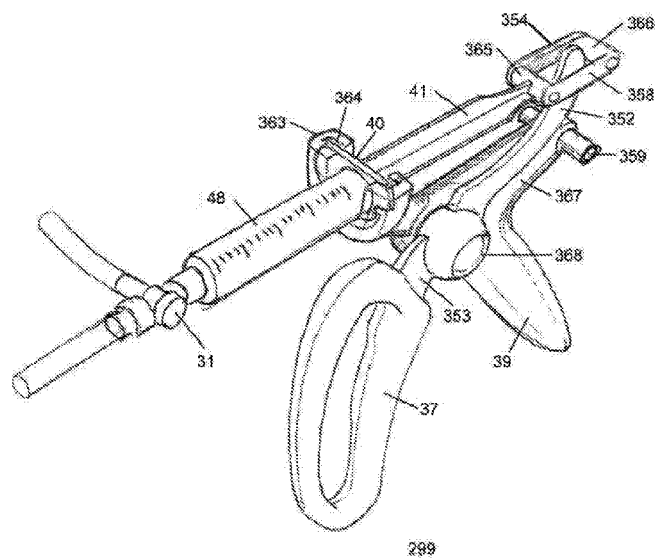
FIG. 31 is an isometric view of an example embodiment of a compact housing according to embodiments of the invention.

Another configuration may have fewer components and have a smaller profile. FIG. 31 is an isometric view of an example embodiment of a compact housing according to embodiments of the invention. FIG. 31 shows system 299. This system can include a syringe 48 and dual check valve 31. Other two-valve systems may be used instead of a dual check valve 31. The syringe 48 can have a flange 40, and a plunger 41. The plunger 41 can have a feature at the distal end with a cross bar 365 and a second cross bar 366, held together by two connecting ribs 358. These features and/or components can create a bracket 354 with an opening which can allow a curved actuation member 352 to move the plunger 41 linearly in and out, as a result of a rotational movement of actuation lever 353 generated by the user grabbing loop trigger 37. The cross bars 365, 366 can be cylindrical to allow sliding with minimal friction when sliding against the actuation member 352. This configuration can eliminate the need for a separate piece acting as a shuttle. The cross bars 365, 366 may be alternately constructed of, for example, a lubricious plastic, a plastic core with a metal sleeve on the exterior, a metal rod surrounded by a plastic exterior, and/or a solid metal piece.

The actuation lever 353 can be connected via a pivot point to the rigid grip 39. A torsion spring 355 can bias the actuation lever 353 to the open position. The torsion spring 355 may be covered by a torsion spring cover 368 to keep contamination out of the torsion spring, or the torsion spring may be exposed. Alternately, or additionally, a leaf spring may be used to bias open the actuation lever 353. The leaf spring may connect to the bottom of the loop trigger 37 and also the bottom of the rigid grip 39, and contain a joint near the pivot point created by the grip 39 and actuation lever 353. The rigid grip 39 can be continuously connected to a holding mount 363, which can have a receiving slot 364. The receiving slot 364 may be sized to receive the syringe flange 40. The receiving slot 364 and syringe flange 40 may have an asymmetry present to force the user to assemble the housing and tubing assemblies together in a single orientation. There may be a rotating tab or other locking feature which can trap the syringe 48 inside the holding mount 363 when the locking feature is deployed by the user. The rigid grip 39 may also have an extension 367 which allows stop pins 359, to provide a consistent stopping point for the actuation lever 353. The location of the stop pins 359 can be correlated with a desired syringe volume. The stop pins 359 can also be used as a pivot point for the housing.

Figure 32A:
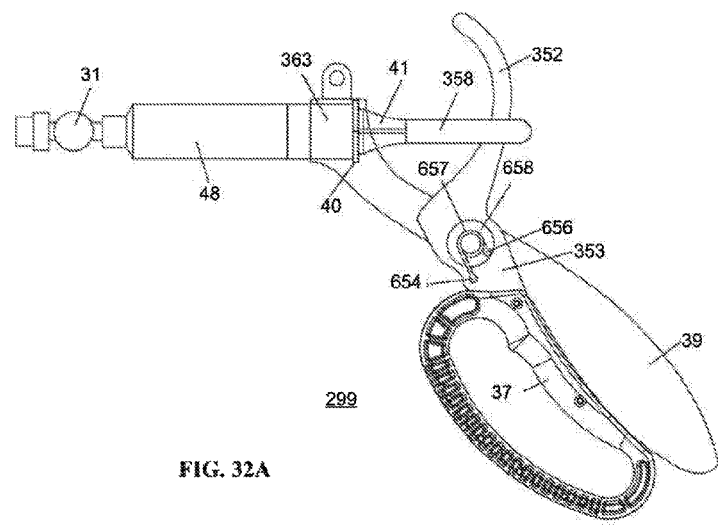
FIG. 32A is a side view of an example embodiment of a compact housing in the open position according to embodiments of the invention.
Figure 32B:
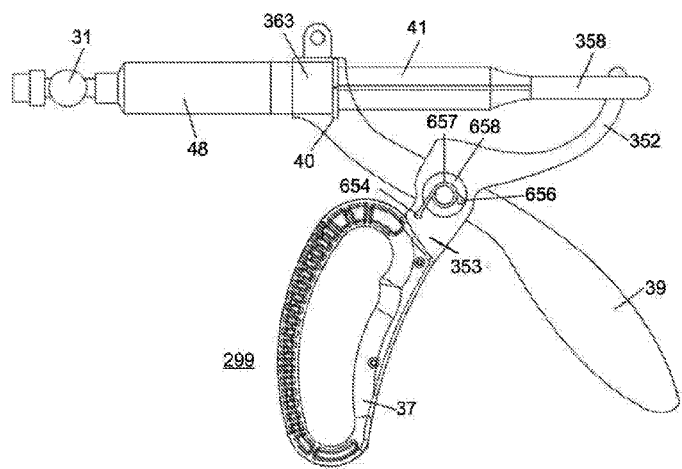
FIG. 32B is a side view of the example embodiment shown in FIG. 32A according to embodiments of the invention.

FIG. 32A is a side view of an example embodiment of a compact housing in the open position according to embodiments of the invention. FIG. 32B is a side view of the example embodiment shown in FIG. 32A according to embodiments of the invention. These figures show detailed views of the torsion spring 657. A protrusion of the rigid handle 658 can form the pivot point for the actuation lever 353. A first leg 656 of the torsion spring 657 is anchored in the pivot protrusion 658, and a second leg 654 is anchored in the actuation lever 353. The torsion spring 657 biases the actuation lever 353 into the open position. In both of these views the extension 367 and stop pins 359 are not shown.

FIG. 33A is a schematic illustration of another example embodiment of a compact housing according to embodiments of the invention. The outer cover 370 can have holes 371 which receive the stop pins 359. The cover 370 can pivot about these pins 359, and this can allow the user to place the syringe 48 into the receiving slots 364 when the cover 370 is pivoted open, and can capture and hold the syringe 48 in place when closed. Locking tabs 372 or other features can be used to hold the outer cover 370 in place. FIG. 33C is an enlarged view of an example embodiment for optional locking tabs 372 for the compact housing of FIG. 33A according to embodiments of the invention. The locking tabs 372 may be located near or on the holding mount 363. The outer cover 370 may be removed entirely if desired for the user for greater access, or for cleaning between procedures through a variety of methods. The user may pry apart the outer cover 370 at the holes 371, which can allow the cover 370 to be removed from the stop pins 359. FIG. 33D is an enlarged view of an example embodiment for optional detents 373 of the compact housing of FIG. 33A according to embodiments of the invention. In these embodiments, the holes 371 may have channels with detents 373, which can allow the user to pull the outer cover 370 off when pivoted to the open position. FIG. 33A also shows a torsion spring cover 368.

FIG. 33B is an enlarged view of an example embodiment for the compact housing of FIG. 33A of a syringe flange 40 according to embodiments of the invention. FIG. 33B shows one possible asymmetry 372 which may be present in the syringe flange 40, and can be used to control orientation during use. A corresponding mating feature can be present in the receiving slot 364.

Figure 34:
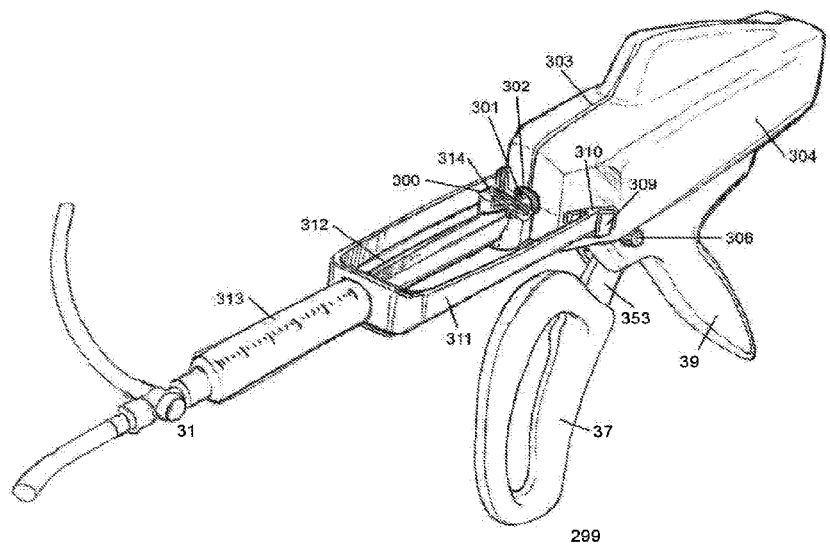
FIG. 34 is an isometric view of an example embodiment of an additional compact housing configuration according to embodiments of the invention.

FIG. 34 is an isometric view of an example embodiment of an additional compact housing configuration according to embodiments of the invention. This configuration can have a loop trigger 37 and grip 39. The grip 39 can be part of a housing 304. The housing 304 can include two halves which may be sealed together via a seal 303. The shuttle 300 is shown on the exterior of the housing 304. As in other configurations the shuttle 300 can have a receiving slot 314 which receives the plunger 312 of a syringe 313. However the shuttle 300 can be connected by a cylinder 301 to the driving mechanism within the housing 304. The cylinder 301 can be sealed by an o-ring 302 or other component which can prevent or reduce water and other fluids from entering the housing 304. The syringe flange can have a feature which includes leg extensions 311 and placement tabs 310. The placement tabs can be configured to fit into receiving tabs 309 present on the exterior of the housing 304. The receiving tabs 309 can hold the syringe 313 in place during use, and the leg extensions 311 can provide a natural boundary when the shuttle 300 is moving linearly to cycle the syringe plunger 312. The user can drop the syringe 313 vertically into both the receiving slot 314 and receiving tabs 309 before use. A pin lock 306 may be used to hold the loop trigger 37 and actuation lever 353 in a desired position, which can result in the shuttle 300 being pre-aligned with the plunger 312. A variety of previously disclosed actuation mechanisms may be used to actuate the shuttle motion.

Figures 35A, 35B:
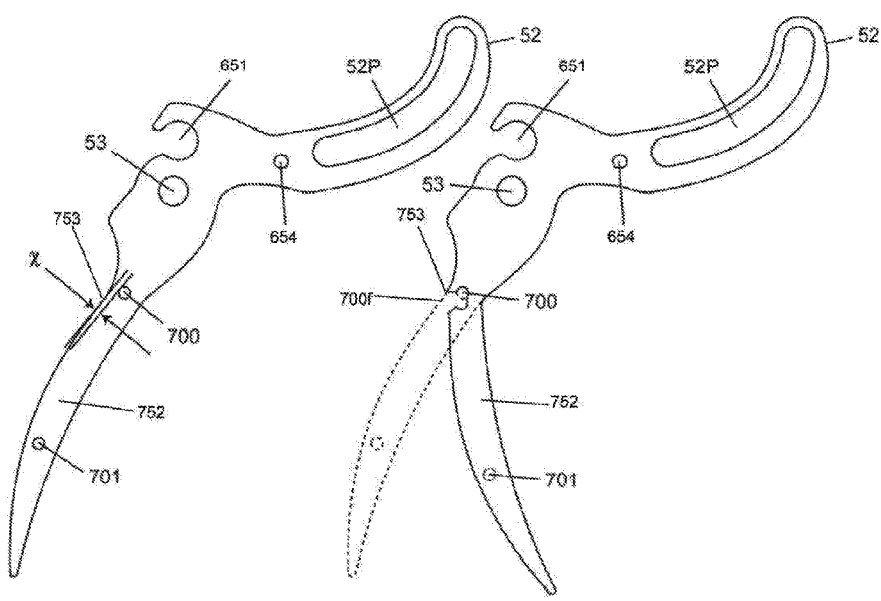
FIG. 35A is a side view of an example embodiment of a lever of an infusion device in operative position, according to embodiments of the invention.
FIG. 35B is a side view of the lever shown in FIG. 35A, after breaking due to exertion of a force above a defined amount, according to embodiments of the invention.

FIG. 35A is a side view of an example embodiment of a lever 52 of an infusion device in operative position, according to embodiments of the invention. The lever 52 engages the shuttle mechanism as described above. FIG. 35A depicts the lever 52 with a narrow segment of material 753 having a defined width dimension X measured from an outer perimeter of the lever 52 to a line drawn tangent to an aperture 700. The dimension X of the narrow segment of material 753 may range from 0.01 inches to 0.15 inches though the present invention is not limited thereto. The narrow segment of material 753 may extend between an upper segment of the lever 52 and a lower segment 752 in or attached to the lever 52 which can disengage, break, and/or deform if an input force greater than a defined threshold is applied by a user. This force can correlate to an infusion pressure provided by the infusion device and the disengagement, breaking, and/or deformation of the lower segment 752 may inhibit overpressure of the fluid delivery by the infusion device. The greater than desired force can be above 10 lbf, typically above 50 lbf, 60 lbf, 70 lbf, or 80 lbf, though the present invention is not limited thereto. In some embodiments, the force at which the lever 52 can disengage, break, and/or deform may be defined so as to limit the pressure at which fluid is delivered by the infusion device to below a defined pressure from 5.8 PSI to 325 PSI, typically 5.8 PSI, 10 PSI, 50 PSI, 100 PSI, 200 PSI, 300 PSI, or 320 PSI, though the present invention is not limited thereto. The lower segment 752 can be integral to the lever 52 or can be attached to the lever 52. In some embodiments, the dimension "X" of the narrow segment of material 753 is associated with an upper aperture 700 positioned under the pivot point 53. A second aperture 701 may also serve to hold the lever 52 in place in the housing, but may not participate in determining the force for disengaging, breaking, and/or deforming the lower segment 752 of the lever 52. Also illustrated in FIG. 35A, the lever 52 can attach or define the trigger pivot 53, the return spring anchor point 654, and/or the pin lock cutout 651. When the user applies a greater than desired amount of force to the infusion device via the trigger 37, the segment of material 753 adjacent the upper aperture 700 can fracture, and the lower segment 752 of the lever 52 may extend rearward relative to its intact configuration during normal operation as a result of the undue input force. Though the lever 52 is described as having a segment that can break, it will be understood by those of skill in the art that breaking of the lever 52 may include other types of structural disengagement, deformation and/or derivatives thereof that render the lever 52 with a diminished ability to operate the shuttle of the housing.

FIG. 35B is a side view of the lever 52 shown in FIG. 35A, after breaking due to exertion of a force above a defined amount, according to embodiments of the invention.

FIG. 35B depicts the lever 52 after an input force has been exceeded a defined threshold value. The lower segment 752 of the lever 52 extends more rearward relative to its intact configuration during normal operation, and the narrow segment of material 753 near upper aperture 700 has separated. In some embodiments, this separation may deform or otherwise alter the aperture 700 of FIG. 35A to define a deformation zone 700f in the lever 52. The thickness of dimension X can be varied as desired to increase or reduce the force at which the lower segment 752 of the lever 52 disengages, breaks, and/or deforms. In some embodiments, when the lower segment 752 of the lever 52 disengages, breaks, and/or deforms, this action can provide a tactile response to the user. This allows the user to detect the overpressure condition of the undue applied force without direct visualization, such as in loud or distracting environments. Additionally, when disengaged, broken, and/or deformed, the lever 52 will no longer travel through the full range of linear stroke motion, providing another tactile and visual signal to the user that the infusion device has exceeded the force threshold.

In some embodiments, the dimension X of the narrow segment 753 may be approximately 0.07 inches in an aluminum lever 52 which is approximately 0.12 inches thick, though the present invention is not limited thereto. This configuration may result in a break-away force of approximately 70 lbf. This break-away force can be tuned greater or lesser depending on the desired function of the device. The break-away force may be controlled using only dimension X if desired. Additionally, the material thickness, material type or aperture 700 location may also be varied as desired. The breakaway force can be checked through finite element modeling (FEA). In some embodiments, the break-away force may be tuned relative to the output pressure of the fluid exiting the infusion device, rather than, or in addition to, the input force. Input force and output pressure may be linearly correlated, and can be calculated as desired. It will be understood that a break-away force may include force which only deform or otherwise alter the lever 52 or a segment attached thereto and that a full breakage is not required to achieve the objectives of the present invention.

Figure 36A:
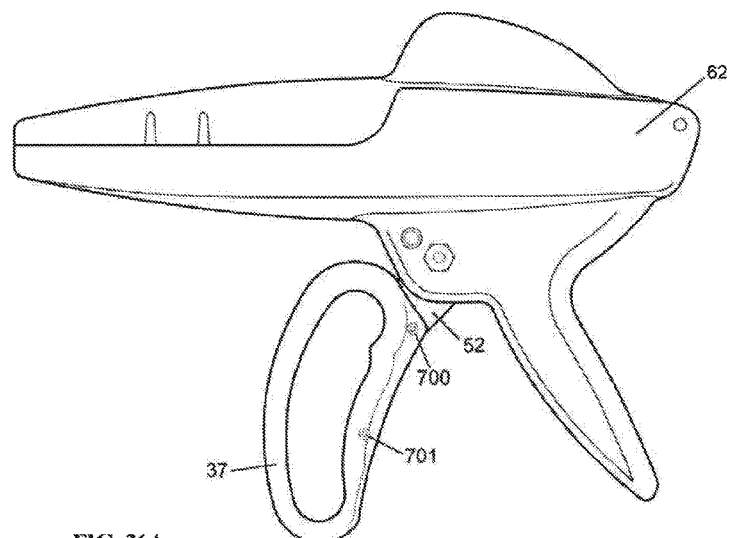
FIG. 36A is a side view of an example embodiment of a housing with the lever shown in FIG. 35A before the lever breaks according to embodiments of the invention.
Figure 36B:
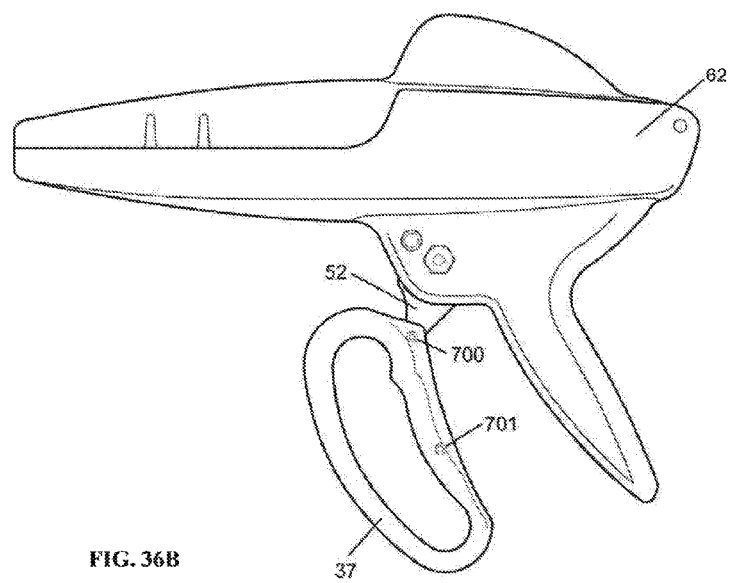
FIG. 36B is a side view of an example embodiment of the housing shown in FIG. 36A after the lever breaks according to embodiments of the invention.

FIG. 36A is a side view of an example embodiment of a housing 62 with the lever 52 shown in FIG. 35A before the lever 52 breaks according to embodiments of the invention. FIG. 36B is a side view of an example embodiment of the housing 62 shown in FIG. 36A after the lever 52 breaks according to embodiments of the invention. These figures illustrate the breakage of the lever 52 of FIGS. 35A & 35B as viewed when assembled with a trigger 37 and housing 62. The connectors through upper aperture 700 and lower aperture 701 that can hold the trigger 37 onto lever 52 are visible in this view.

Figures 37A, 37B:
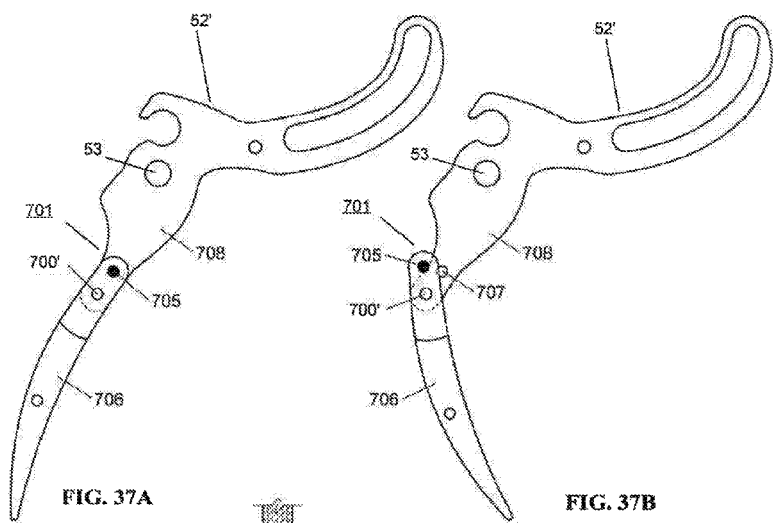
FIG. 37A is a side view of an example embodiment of a lever with a resettable hinge according to embodiments of the invention.
FIG. 37B is a side view of the lever shown in FIG. 37A with the resettable hinge, after disengaging, according to embodiments of the invention.
Figure 37C:
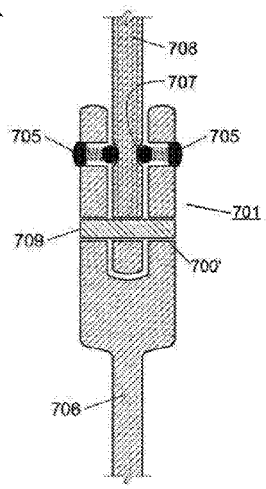
FIG. 37C is a cross-sectional view of the example embodiment of the lever with the resettable hinge shown in FIG. 37A, according to embodiments of the invention.

FIG. 37A is a side view of an example embodiment of a lever 52' with a resettable hinge 701 according to embodiments of the invention. FIG. 37B is a side view of the lever 52' shown in FIG. 37A with the resettable hinge 701, after disengaging, according to embodiments of the invention. FIG. 37C is a cross-sectional view of the example embodiment of the lever 52' with the resettable hinge 701 shown in FIG. 37A, according to embodiments of the invention. In some embodiments, the lever 52' may include a lower segment 706 that can disengage without permanent damage thereto. FIGS. 37A & 37B illustrate an example embodiment of the resettable lever 52' in a normal and disengaged position, respectively. In some embodiments, the resettable lever 52' may include an upper segment 708 and a lower segment 706 under pivot point 53, which can be a primary pivot point. In some embodiments, the lower segment 706 can be attached to the upper segment 708 via a secondary pivot point 700', which may allow the lower segment 706 to disengage if a defined force is exceeded. The lower segment 706 may normally be held rigidly in place relative to the upper segment 708. In some embodiments, the lower segment 706 may be held rigidly in place relative to the upper segment 708 by two spring loaded ball plungers 705 which form a detent. The ball plungers 705 may seat into two recesses 707 which can allow purchase against the upper segment 708, during normal use of the lever 52'. A secondary pivot pin 709 may extend through both the upper segment 708 and the lower segment 706, through the secondary pivot point 700'. The amount of force required to disengage the lower segment 706 can be dependent on the spring force of the ball plungers 705, and the amount of interference with the recesses 707. If the defined force is exceeded, a user may return the lower segment 706 to be rigidly connected to the upper segment 708 of the lever 52', by pulling the lower segment 706 outward. The edges of the upper segment 708 may be chamfered or radiused to allow the force used to reset the lower segment 706 to be lower than the force required to disengage the lower segment 706. The force at which the lower segment 706 will disengage may be above 10 lbf, typically above 50 lbf, 60 lbf, 70 lbf, or 80 lbf, though the present invention is not limited thereto. In some embodiments, the force at which the lower segment 706 will disengage may be defined so as to limit the pressure at which fluid is delivered by the infusion device to below a defined pressure from 5.8 PSI to 325 PSI, typically 5.8 PSI, 10 PSI, 50 PSI, 100 PSI, 200 PSI, 300 PSI, or 320 PSI, though the present invention is not limited thereto. In some embodiments, a metal loop may be positioned by the user such that that no movement may be possible around the secondary pivot point 700'. This may allow the user to use the device at greater pressures in urgent situations, and then return to normal use as desired. In some embodiments, fixation devices may also be used instead of ball plungers 705 to rigidly hold the lower portion 706 of the lever 52' to the upper portion 708. In some embodiments, a resettable hinge 701 with a fixed detent, or pairs of magnets, may be used instead of, or in addition to, ball plungers 705. Those of ordinary skill in the art will appreciate that additional configurations to achieve the resettable hinge 701 of the lever 52' may be possible as contemplated by the present invention.

FIG. 37D is a side view of an example embodiment of a lever 52" with a resettable hinge 701' with a magnetic latch according to embodiments of the invention. FIG. 37E is a side view of the lever 52" shown in FIG. 37D with the resettable hinge 701', after disengaging, according to embodiments of the invention. FIG. 37F is a partial cross-sectional view of the example embodiment of the lever 52" with the resettable hinge 701' shown in FIG. 37D, according to embodiments of the invention. In some embodiments, the resettable hinge 701' may include at least one magnet within a part of the lever 52" which secures an upper segment 708' to a lower segment 706'. Thus, the upper segment 708' of the lever 52" may releasably engage the lower segment 706' of the lever 52" via magnetic force. In some embodiments, the magnetic force may be applied by an upper magnet 714 that may be connected to the upper segment 708' of the lever 52" and a lower magnet 715 that may be connected to the lower segment 706' of the lever 52". Upper segment 708' and/or lower segment 706' may include fastening means for elements of the housing, such as, for example, screw holes 716 and 717. A return spring, such as torsion spring 157 illustrated in FIG. 26A may be connected to the lever 52" via attachment points, such as spring attachment hole 718. When in use, the upper segment 708' and the lower segment 706' of the lever 52" may remain connected via the magnetic force so as to pivot the lever 52" about the pivot point 53, which may be a primary pivot point, in response to user input. When a force exceeding a defined force is applied to the lever 52", the lower segment 706' may disengage from the upper segment 708' of the lever 52". The lower segment 706' may pivot about the secondary pivot point 700", and the upper segment 708' may no longer move in response to user input to stop the plunger of the syringe from further movement and thereby stop further liquid delivery from the syringe. FIG. 37E depicts the lower segment 706' after separation from the upper segment 708'. The desired force to achieve this breakaway may be tuned by varying the composition, diameter, thickness and/or separation distance of magnets, such as magnets 714 and 715, connected to the upper and lower segments 708'/706' of the lever 52". Though two magnets are illustrated in FIGS. 37D and 37E, other configurations of magnets are possible without deviating from the invention. In some embodiments, a magnet 714 or 715 can be attached to one of the lower or upper segment 706'/708' and the other segment 708'/706' may be metal. In some embodiments, a single magnet may be used between two steel plates (or other metal) to increase the separation force.

In some embodiments, the location of a magnetic element may be adjusted to increase or decrease the lever between the magnetic element and the secondary pivot point 700". Moving the magnets further from the secondary pivot point 700" may decrease the magnetic force required to maintain the resettable magnetic hinge 701'. In some embodiments, a rare earth magnet and/or ferromagnetic material may be used to generate the force required. In some embodiments, neodymium magnets may be used to generate the force required. In some embodiments, the defined force at which the resettable magnetic hinge 701' will disengage may be 100 lbf in order to limit the pressure in the syringe to approximately 100 PSI. If the magnets 714/715 are located 0.75 inches from the secondary pivot point 700", and the center distance of the input force is 0.25 inches from the secondary pivot point 700" a magnetic force of 33 lbs is required. FIG. 37F shows a partial cross section view of the secondary pivot point 700", and the upper 708' and lower 706' segments of the lever 52". Those of ordinary skill in the art will appreciate that additional configurations to achieve the resettable hinge 701' of the lever 52" may be possible as contemplated by the present invention.

Figure 38:
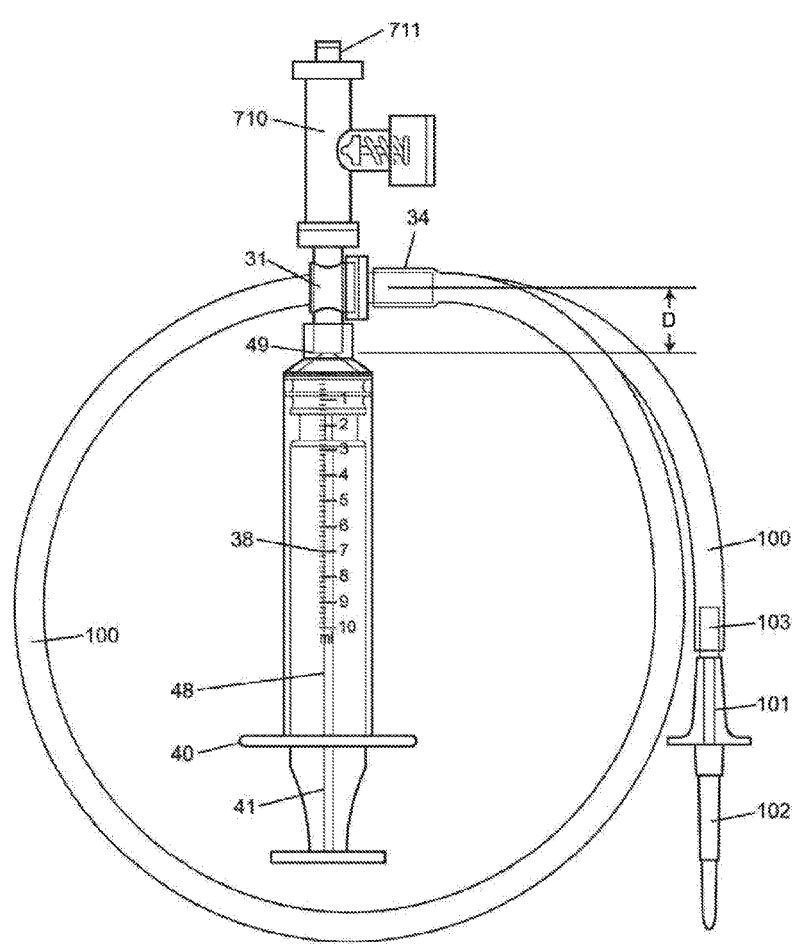
FIG. 38 is a top view of an example embodiment of an outlet tubing set with a pressure relief valve that can be connected to a valve, according to embodiments of the invention.

FIG. 38 is a top view of an example embodiment of an outlet tubing set 100 with a pressure relief valve 710 that can be connected to a valve 31, according to embodiments of the invention. The tubing set 100 may be similar to the tubing set 100 illustrated in FIG. 19A with the addition of the pressure relief valve 710. The pressure relief valve 710 may limit the fluidic pressure which can be applied to the patient. In some embodiments, the pressure relief valve 710 may open to release fluids being dispensed through the output tubing when pressure as determined at the pressure relief value 710 exceeds a defined limit. In some embodiments, the pressure relief valve 710 may reduce or block fluids being dispensed through the output tubing when pressure as determined at the pressure relief value 710 exceeds a defined limit. The pressure relief valve 710 may be connected directly to the outlet of the dual check valve 31, and there may be a male luer connection 711 on the outlet side of the pressure relief valve 710. In some embodiments, there may also be a length of small bore outlet tubing between the outlet of the dual check valve 31 and the pressure relief valve 710. The pressure relief valve 710 may be set as desired to a clinically relevant pressure. Some "high pressure" infusers have a maximum pressure of 300 or 320 PSI, and this may be used as a set point. Other set pressure points may also be chosen as desired. One example of a pressure relief valve which may be used in some embodiments includes the "T" pressure relief valve provided by Halkey-Roberts Corporation of Saint Petersburg, Florida. In some embodiments, the pressure relief value 710 can be mechanically combined with a pressure transducer, such as the pressure transducer 93 of FIG. 9 and/or the pressure transducer 227 of FIG. 21.

In some embodiments, a user may choose to override the pressure relief valve 710 if required by the clinical situation. A screw-on cap, a retaining lever, or other device may be actuated by the user to mechanically close the pressure relief valve 710. This may allow the user to continue to apply greater pressures if needed. This override may require positive action from the user in order to override the pressure limit.

Figure 39A:
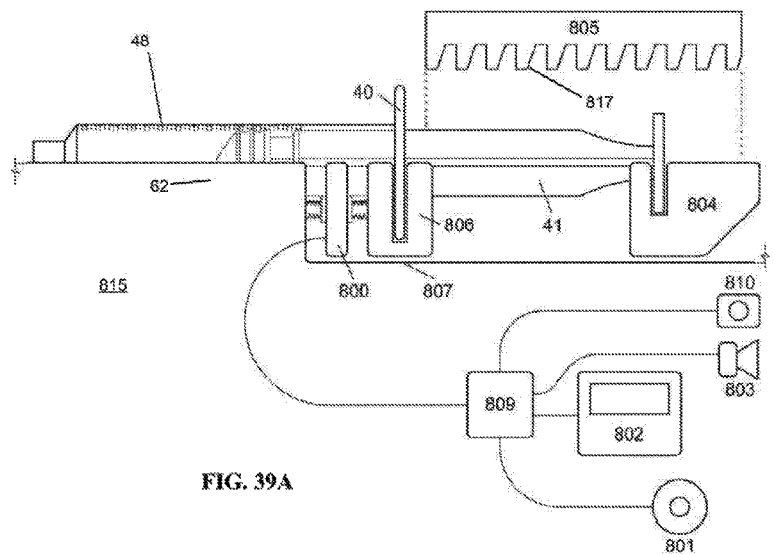
FIG. 39A is a partial schematic side view of an example embodiment of a pressure monitoring system, according to embodiments of the invention.
Figure 39B:
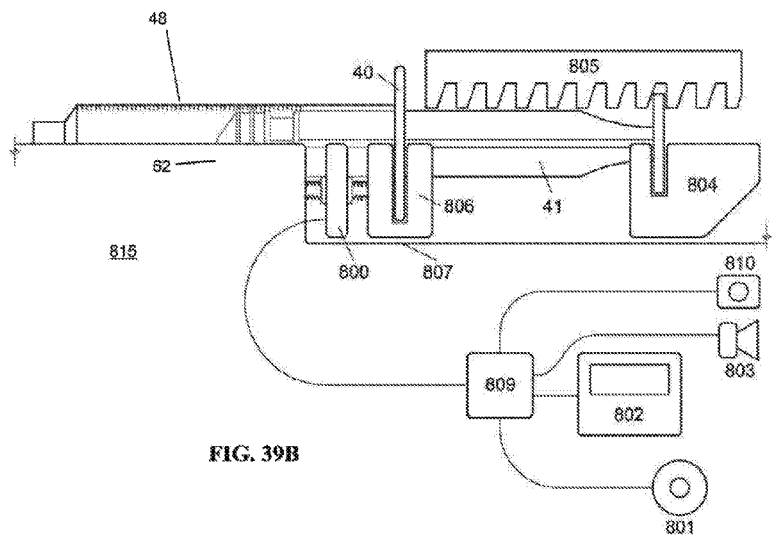
FIG. 39B is a partial schematic side view of the pressure monitoring system of FIG. 39A shown in a locked position, according to embodiments of the invention.

FIG. 39A is a partial schematic side view of an example embodiment of a pressure monitoring system 815, according to embodiments of the invention. FIG. 39B is a partial schematic side view of the pressure monitoring system of FIG. 39A shown in a locked position, according to embodiments of the invention This pressure monitoring system 815 may allow a user to know the pressure being applied to the pressure monitoring system 815 at various points during infusion, and may be used to alert the user if a pressure limit is exceeded. In some embodiments, the pressure monitoring system 815 may lock out the infusion system so greater than desired fluidic pressures cannot be applied to the patient. A load cell 800 may detect the force applied between the syringe flange 40 and the housing 62, when a trigger, such as trigger 37 of FIGS. 36A & 36B, is being actuated and fluid is being forced into or out of the syringe 48. The trigger may apply a force through a series of linkages to the shuttle 804 which moves the plunger 41. Fluid pressure may be generated when a force is applied to the plunger 41 and the flange 40 resists movement. The syringe flange 40 may impart axial force within the housing 62. The housing 62 may impart some vertical forces on the syringe 48 through the length of the syringe 48, and some incidental frictional forces in the axial direction. Some embodiments may use the distal tip of the syringe 48, or other parts of the syringe 48, plunger 41, or valve assembly to measure these forces.

The axial force on the syringe flange 40 can be translated into a pressure measurement, if the diameter of the syringe plunger 41 is known [Pressure=(Measured Force)/(Area of Plunger)]. The force may be measured by a button load cell or other load cell 800 mounted between the housing 62 and a mounting bracket 806. There may be one centrally mounted load cell 800 below and mid-line on the syringe 48, two load cells placed at lateral sides of the mounting bracket 806, or more than two load cells 800 placed in multiple locations. If two or more load cells 800 are used, the total measured force may be summed between all load cells 800. A cut-out 807 present in the housing 62 may provide a defined channel to keep the mounting bracket 806 in-line with the load cells 800. In some embodiments, bushings, linear bearings, and/or other methods may be used to reduce friction between the mounting bracket 806 and the housing 62. The load cell 800 may be a button load cell, which registers compressive forces as the plunger 41 is depressed. In some embodiments, the load cell 800 may be screwed into both the housing 62 and the mounting bracket 806, which may allow both tension and compression to be measured.

In some embodiments, a display 802 on the outside of the housing 62 may show the current pressure being applied to the fluid in the syringe 48. The display 802 may be similar to the display 90 illustrated in FIG. 9 and may include a screen and user interface input such as the screen 91 (which can be a touchscreen) and/or input buttons 92 of FIG. 9. The display 802 can display information including, but not limited to, maximum pressure, current pressure, average pressure, and/or not-to-exceed pressure. The not-to-exceed pressure threshold may be set by the user and/or pre-programmed. Some examples of pre-programmed limits, based on the size of the IV/IO attached are included in Table 1. This data is correlated with a 10 ml syringe.

TABLE 1

Pressure Alarm Limits

| IV/IO access size | Upper Alarm Limit (PSI) | Lower Alarm Limit (PSI) |
|---|---|---|
| 15 G IO needle | 55.8 | 0.0 |
| 16 G | 40.0 | 9.5 |
| 22 G | 94.0 | 21.1 |
| 22 G Central Line | 110.6 | 30.0 |

A user may input an IV/IO size using an input and/or display similar to the display 90 (FIG. 9), or by other input means such as, for example, a touchscreen with graphics. The system 815 may then select an alarm limit based on the table above. If no IV/IO is selected the system 815 may proceed without alarm limits, or may be locked to prevent any motion of the syringe plunger 41 until an IV/IO size is selected. In some embodiments, the not-to-exceed pressure threshold may be the upper alarm limit as illustrated in Table 1. In some embodiments, the upper alarm limit may be a percentage of the not-to-exceed pressure, such as 80% or 90%.

The display 802 may an independent display 802. In some embodiments, the display 802 may be multi-purpose and show volume of fluid transfused and/or other metrics. The display 802 may be connected to the load cell 800 via a processer 809 to translate the signal from the load cell 800. The processer 809 may be connected to a speaker 803, which may be programmed to sound an audible alarm when the pressure reaches or exceeds the not-to-exceed threshold. In some embodiments, the audible alarm may be generated when the pressure reaches or exceeds a level lower than the not-to-exceed threshold, such as the lower alarm limit illustrated in Table 1. The processor 809 may be connected to a pivot point lock 801, a solenoid and/or other device which extends or retracts with force into the trigger to prevent the user from being able to impart any additional force to the trigger and plunger until the force is reduced below the not-to-exceed threshold. In some embodiments, a plunger lock 805 may be advanced by a solenoid or other mechanism and prevent any subsequent plunger 41 movement once a not-to-exceed pressure is reached. The plunger lock teeth 817 may be angled to slightly retract the plunger 41 as the plunger lock 805 engages. This may reduce the applied pressure as the lock is applied. Locking mechanisms may be released by the user pressing a release button 810, which may electronically signal the processer 809. In some embodiments, the processor 809 may release a lock mechanism after a pre-determined amount of time has elapsed.

Figure 40:
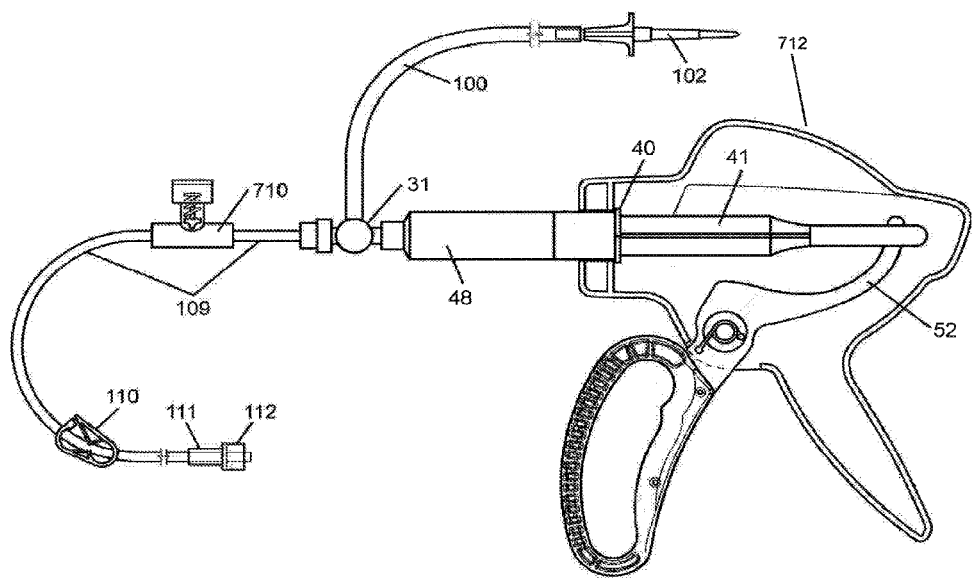
FIG. 40 is a side view of an example embodiment of an infusion device with a syringe inside a housing, according to embodiments of the invention.

FIG. 40 is a side view of an example embodiment of an infusion device with a syringe 48 inside a housing 712, according to embodiments of the invention. In this view, the flange 40 of a syringe 48 and the syringe plunger 41 may be within a housing 712. The housing 712 may have a smaller axial extent that encloses the plunger 41 and flange, while the syringe body 48 may be external. A plunger 41 which interfaces directly with the lever 52 is depicted here, but other configurations of plunger 41 and lever 52 may be used. In some embodiments, the housing 712 may be pre-loaded with the syringe 48, and may be locked or sealed so as to inhibit, prevent, or make the housing 712 difficult to open by the user. This may reduce set-up and/or the potential for use errors, because the system requires little assembly by the user. The syringe 48 may be attached to a dual check valve 31. A spike 102 may be connected to large bore inlet tubing 100, which leads to the inlet of the dual check valve 31. Outlet tubing 109 may lead to a pressure relief valve 710. Also shown is a thumb clamp 110 and male luer outlet 111. Additional tubing features such as a needleless Y valve may also be incorporated in some embodiments of the configuration. As shown in this embodiment, the syringe body 48 may be external to the housing 712 and directly visible to the user. As described above, other embodiments may include a housing 712 which encapsulates the entire syringe body 48, and may have a clear canopy to view the syringe body 48. In some embodiments, this canopy may not be able to pivot open during use. Other embodiments may incorporate or integrate the body of the syringe 48 directly into the housing 712, such that the syringe body 48 and the body of the housing 712 may be a single integrated piece. This may further reduce assembly time and/or manufacturing costs.

Figure 41A:
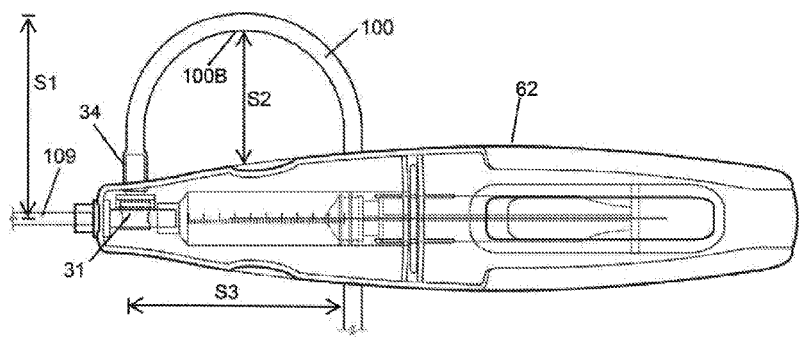
FIG. 41A is a top view of an example embodiment of an infusion device with a housing with integrated or attached inlet tubing management features, according to embodiments of the invention.
Figure 41B:
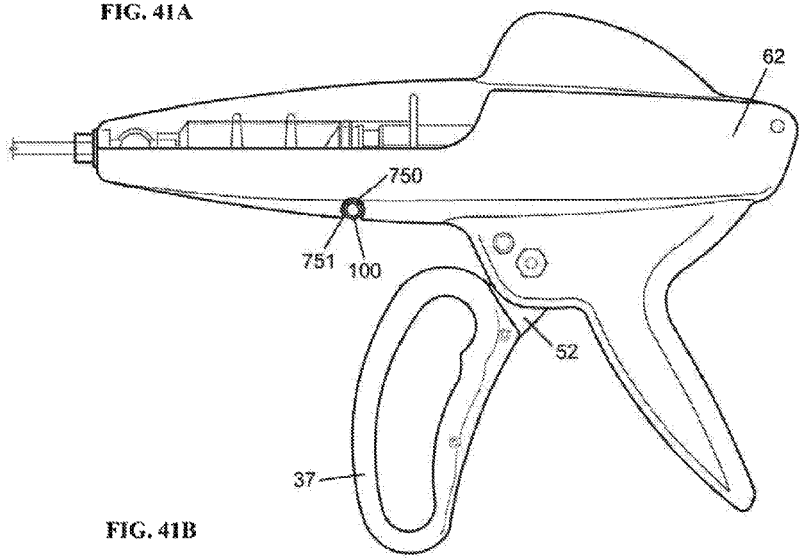
FIG. 41B is a side view the infusion device shown in FIG. 41A, according to embodiments of the invention.
Figure 41C:
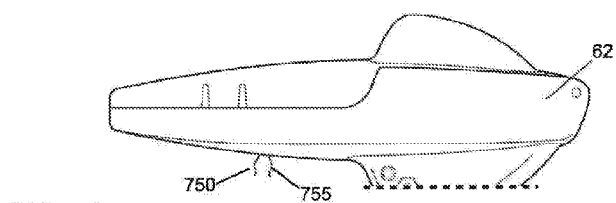
FIG. 41C is a side view of an infusion device similar to that shown in FIG. 41A, according to other embodiments of the invention.

FIG. 41A is a top view of an example embodiment of an infusion device with a housing with integrated or attached inlet tubing management features 750, according to embodiments of the invention. FIG. 41B is a side view the infusion device shown in FIG. 41A, according to embodiments of the invention. FIG. 41C is a side view of an infusion device similar to that shown in FIG. 41A, according to other embodiments of the invention. In some embodiments, the tubing management feature 750 may comprise a retaining feature. The inlet tubing management feature 750 may be a semi-circular cross-channel or opening 751 which has a large enough diameter to receive inlet tubing 100, but a small enough opening 751 to retain the inlet tubing 100 during normal use. The inlet tubing 100 may deform as it is pressed into the tubing management feature 750 and may remain trapped until the user pulls it free. This opening 751 may be used if the inlet tubing 100 is exiting to the right (as illustrated in FIG. 41A), but the user may wish to connect the inlet tubing 100 to a bag of fluid which is to the left of the user. The tubing 100 may be looped underneath the housing 62, and held in place by the tubing management feature 750. The tubing management feature 750 may orient the inlet tubing 100 in such a way as to generate a bend 100B in the tubing 100. The bend 100B in the tubing 100 may be a distance S1 from a centerline of an outlet tubing 109 of the housing 62. In some embodiments, the distance S1 may be between about 2 and about 10 inches. The bend 100B in the tubing 100 may be a distance S2 from an edge of the housing 62. In some embodiments, the distance S2 may be between about 1 to about 9 inches. The tubing management feature 750 may orient the inlet tubing 100 so as to cross the housing 62 at a distance S3 from an inlet portion 34 of the dual check valve 31. In some embodiments, the distance S3 may be between about 1 to about 8 inches. In some embodiments, the tubing management feature 750 may be a clamp 755 held under the housing 62 as illustrated in FIG. 41C.

Figure 42:
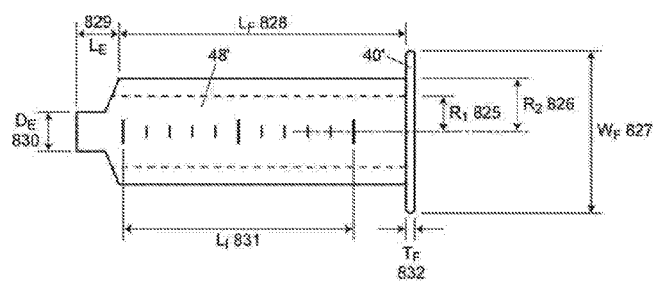
FIG. 42 is a side view of example syringe bodies with varying volumes but with a constant stroke for infusion devices according to embodiments of the invention.

FIG. 42 is a side view of example syringe bodies with varying volumes but with a constant stroke for infusion devices according to embodiments of the invention. FIG. 42 depicts two different syringes bodies that have the same overall length, but which hold varying volumes of fluids. The syringe body 48' may have indicia which cover a fixed length $L_1$ 831. The inner radius can have multiple sizes such as, for example, $R_1$ 825 or $R_2$ 826. The thickness $(T_F)$ 832, the height (not shown), and width $(W_F)$ 827 of the flange 40' may be fixed, as well as the location of the flange $(L_F)$ 828 relative to the most proximal indicia mark. The diameter of the exit $(D_E)$ 830 may also remain constant, and may be sized to receive a female luer fitting. The exit may also be a fixed distance $(L_E)$ 829 from the most proximal indicia. To allow the stroke length to remain constant irrespective of the volume of the syringe 48', a radius R of the syringe body 48' can follow the following formula:

$$R = \sqrt{V/(L\pi)}$$

where v is me syringe volume, and L is the fixed length of the indicia. For example, using this formula a 10 cc syringe 48' with a fixed length of 5 cm may have an inner radius of 0.798 cm, while a 20 cc syringe with the same fixed length may have an inner radius of 1.128 cm.

Figure 43:
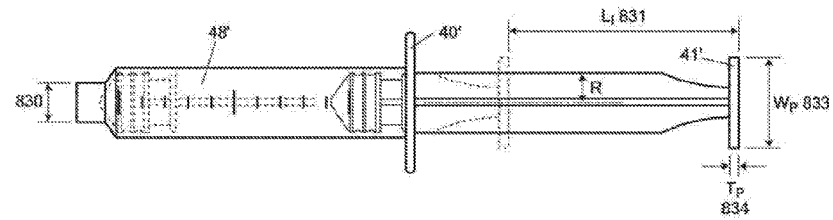
FIG. 43 is a side view of a syringe such as those shown in FIG. 42, illustrated with the plunger shown in the fully depressed and fully retracted (broken line) positions, according to embodiments of the invention.

FIG. 43 is a side view of a syringe such as those shown in FIG. 42, illustrated with the plunger shown in the fully depressed and fully retracted (broken line) positions, according to embodiments of the invention. The fully depressed position illustrates where the plunger 41' has been pushed forward and the fluid evacuated from the syringe body 48'. The fully retracted position illustrates where the plunger 41' has been pulled back to the greatest volume shown on the syringe indicia. The plunger 41' that fits within a syringe 48' that meets this formula may have the same travel distance $(L_I)$ 831 as the length of the indicia on the syringe 48'. The width $(W_P)$ 833 and thickness $(T_P)$ 834 of the plunger 41' may also be fixed, and the radius (R) of the plunger 41' may match the radius of the syringe 48'.

Figure 44:
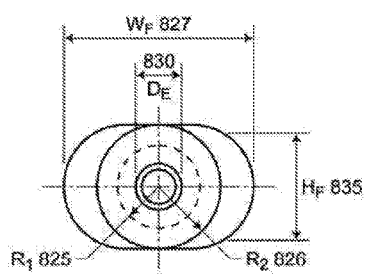
FIG. 44 is a front view of example syringe bodies with different sizes for use in a common infusion device, according to embodiments of the invention.

FIG. 44 is a front view of example syringe bodies with different sizes for use in a common infusion device, according to embodiments of the invention. An example of a syringe with a smaller diameter $R_1$ 825 configuration is shown as a dotted line, and an example of a syringe with a larger diameter $R_2$ 826 configuration is shown as a solid line. In some embodiments, both configurations may have the same size syringe flange 40' and/or exit 830. In some embodiments, the width $(W_F)$ 827, and height $(H_F)$ 835 of the flange 40' may be fixed.

Figure 45A:
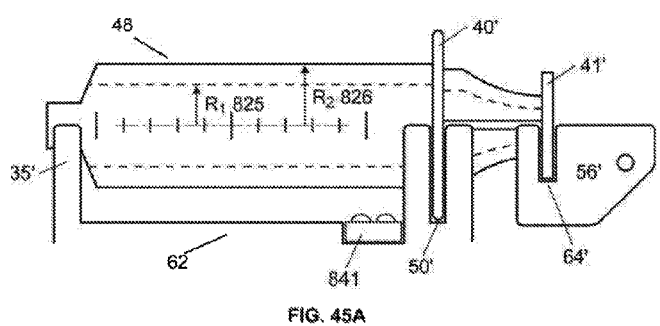
FIG. 45A is a partial schematic side view of an infusion device that can serially and interchangeably hold syringes with different volumes, according to embodiments of the invention.

FIG. 45A is a partial schematic side view of an infusion device that can serially and interchangeably hold syringes with different volumes, according to embodiments of the invention. In some embodiments, the infusion device may detect a volume of a syringe 48 placed within the housing 62. In some embodiments, the detection may be automatic. One or more syringe detection sensors 841, such as, for example, an infrared proximity sensor, other proximity sensor, a pressure sensor, an optical sensor, and/or RFID reader, may detect objects placed in the housing 62. In some embodiments, the proximity sensor 841 may be directed at the syringe 48. The proximity sensor 841 may be used to measure the distance between the housing and the syringe body 48, when placed on the centerline of the syringe body 48. A larger distance between the proximity sensor 841 and the syringe 48 may indicate the presence of a smaller syringe (e.g. 10 ml), and a smaller distance between the proximity sensor 841 and the syringe 48 may indicate a larger syringe (e.g. 20 ml). Additionally or alternatively, multiple sensors may be used at once to determine syringe size and location.

Figure 45B:
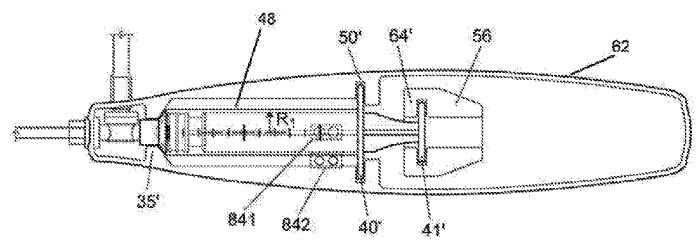
FIG. 45B is a top view of the infusion device in FIG. 45A containing a syringe of a first size and a syringe detection sensor configuration according to embodiments of the invention.

FIG. 45B is a top view of the infusion device in FIG. 45A containing a syringe 48 of a first size and a syringe detection sensor configuration 841/842 according to embodiments of the invention. In this view, two sensors, a midline sensor 841, and a lateral sensor 842, are shown. In some embodiments, when a syringe 48 with a radius $R_1$ is held in the housing 62, the mid-line sensor 841 may indicate that an object is present, and the lateral sensor 842 may not indicate that an object is present. This may indicate that a smaller syringe 48 was being used (10 ml, as one example). This dual sensor configuration may have the advantage of utilizing a presence detection sensor as compared to a distance detection sensor such as the single midline sensor 841 of FIG. 45A.

Figure 45C:
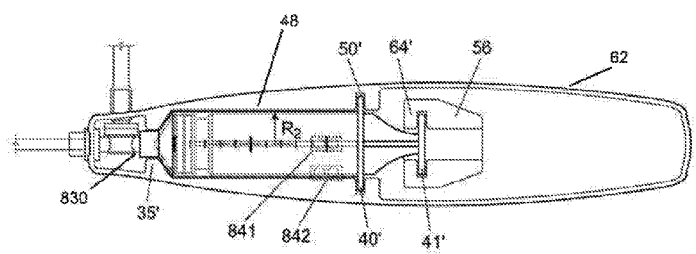
FIG. 45C is a top view of the infusion device from FIG. 45A containing a syringe of a second size different from the syringe of the first size shown in FIG. 45B, according to embodiments of the invention.

FIG. 45C is a top view of the infusion device from FIG. 45B containing a syringe 48 of a second size different from the syringe 48 of the first size shown in FIG. 45B, according to embodiments of the invention. In this view two sensors are shown, a midline sensor 841 and a lateral sensor 842. In some embodiments, when a larger syringe 48 with a radius $R_2$ is held in the housing 62, the mid-line sensor 841 may indicate that an object is present, and the lateral sensor may also indicate that an object is present. This may indicate that a larger syringe was being used (20 ml, as one example). In some embodiments, additional sets of sensors may be used at different axial and/or radial locations to better characterize the syringe location and size.

Variable syringe sizes may impact both pressure and volume transfused. In some embodiments, the sensors 841 and 842 may provide a pre-programmed syringe size to a processor 158" of a volume calculation system 818, to calculate the volume infused. Table 2 illustrates volume calculations for example syringe sizes.

TABLE 2

Volume Infused Based on Syringe Volume

| Syringe Volume | Full stroke Volume (ml) | 50% stroke volume (ml) | 25% stroke volume (ml) |
|---|---|---|---|
| 10 ml | 10 | 5 | 2.5 |
| 20 ml | 20 | 10 | 5 |
| 30 ml | 30 | 15 | 7.5 |

In Table 2, three example syringe size are shown indicating the housing 62 can serially and interchangeably hold at least these three different sizes of syringe 48. However, two, four, or other syringe sizes may also be possible. The applied pressure may also vary based on plunger diameter. The previous example demonstrated two syringe plunger diameters (e.g. $R_1$ and $R_2$) which may be possible if used in this configuration. For example, a 10 ml syringe 48 with a fixed length of 5 cm may have an inner radius of 0.798 cm, while a 20 ml syringe with the same fixed length may have an inner radius of 1.128 cm. The user input force F, would result in various fluid pressures within the syringe, according the following formula:

$$P = \frac{F*C}{\pi R^2},$$

where P is the fluid pressure in the syringe, F is the user input force applied to the handle, C is a constant based on the mechanical advantage of the lever connecting the user input force to the syringe plunger, and R is the radius of the syringe plunger. Example values for this formula are shown Table 3 below, where C is given as 0.9. The column "Linear Plunger Force" is the horizontal force applied to the plunger resulting from a given user input on the lever.

TABLE 3

Pressure Based on Input Force

| User Input Force (LBF) | Linear Plunger Force (LBF) | 10 ml Syringe Pressure (PSI) | 20 ml syringe Pressure (PSI) |
|---|---|---|---|
| 50 | 45 | 90 | 45 |
| 70 | 63 | 126 | 63 |
| 100 | 90 | 180 | 90 |
| 150 | 135 | 270 | 135 |
| 167 | 150 | 300 | 150 |

By constraining the body of the syringe 48 at two points, the flange 40' and the exit 830, a variety of syringe sizes may be used within a single housing 62 with only one set of receiving slots. For example, in some embodiments 5 cc, 10 cc, 20 cc, 30 cc, 50 cc and/or 60 cc syringes may be used, though the present invention is not limited thereto. A receiving slot 50' in the housing 62 body may restrain the syringe flange 40', while the circular cutout 35' may restrain the syringe exit 830. The receiving slot 50' may provide an axial restraint. If the plunger 41' also remains a constant size, a receiving slot 64' in the shuttle 56' may be used to control the plunger 41' movement on a variety of syringe sizes. Because the indicia length may be the same between a variety of syringes, the same actuation trigger can work to actuate any of the syringes used in this system 818. This can allow the use of multiple syringe sizes with a single housing 62 design. As illustrated in FIG. 45B compared to FIG. 45C, the smaller diameter syringes $R_1$, may have a larger gap between the walls of the syringe 48 and the housing 62, but may still be fully constrained by the exit 830, syringe flange 40', and plunger 41'.

Figure 45D:
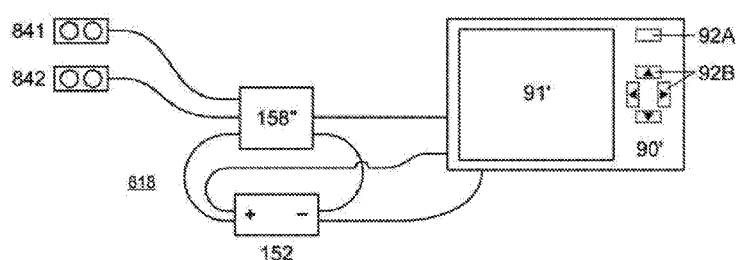
FIG. 45D is a schematic view of a monitoring system for the infusion device of FIGS. 45A-45C configured to determine a size of a respective syringe, according to embodiments of the invention.

FIG. 45D is a schematic view of a monitoring system 818 for the infusion device of FIGS. 45A-45C configured to determine a size of a respective syringe, according to embodiments of the invention. The system 818 of FIG. 45D may include a display 90' similar to the one illustrated in FIG. 9, a processor 158", a power source 152, and/or one or more sensors 841/842. The display 90' may include a screen 91' and buttons 92A/92B. The screen 91' may allow a use of the infusion device to view the pressure being applied at any given moment. The buttons 92A/92B may allow the user to interact with the monitoring system to perform functions such as, for instance, manually entering a syringe size in use. The display may be connected to a processor 158" which may provide an indication of pressure. The indication of pressure by the processor 158" may be based in part on input from sensors, such as sensors 841 and 842. The processor 158" may be powered by a power source 152. The power source 152 may be a battery or other power source such as a plug-in cord configured to be connected to a power receptacle, but the present invention is not limited thereto. The processor 158" may also direct a locking of the infusion device, such as that of the embodiment illustrated in FIGS. 39A and 39B. In some embodiments, the processor 809 of FIGS. 39A and 39B may be the same or similar as the processor 158" illustrated in FIG. 45D.

Figure 46A:
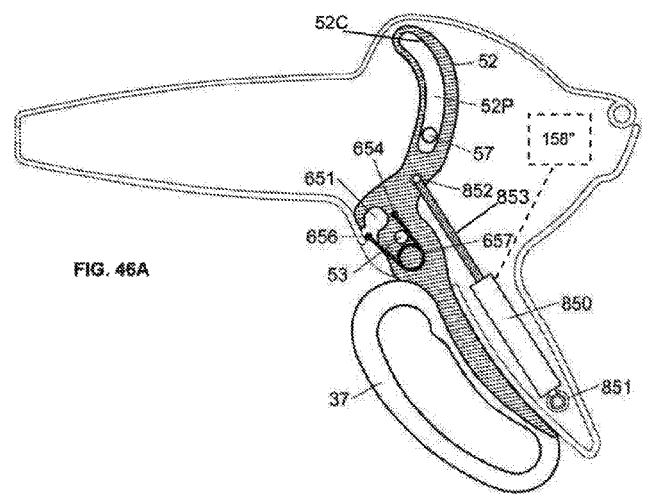
FIG. 46A is a side view of an infusion device incorporating an electromechanical actuation member, according to embodiments of the invention.
Figure 46B:
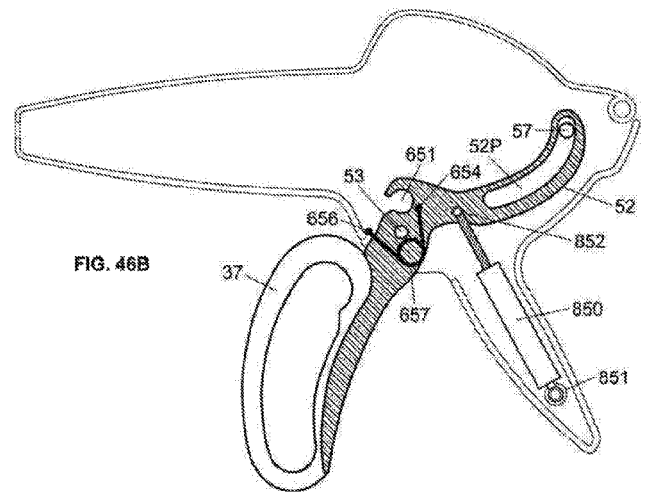
FIG. 46B is a side view of the infusion device of FIG. 46A with the trigger extended, according to embodiments of the invention.

FIG. 46A is a side view of an infusion device incorporating an electromechanical actuation member 850, according to embodiments of the invention. FIG. 46B is a side view of the infusion device of FIG. 46A with the trigger 37 extended, according to embodiments of the invention. As described herein a pin 57 may travel along a cam surface 52C within a path 52P of the lever 52 as the lever 52 rotates. In some embodiments, lever 52 of the infusion device may be mechanically coupled to electromechanical actuation member 850. The electromechanical actuation member 850 may comprise a linear actuator or lead screw motor and may be activated continuously to move a plunger 853 in response to input by the user. This electromechanical actuation member 850 may serve as an alternate actuation member for the system previously disclosed in FIG. 11. In some embodiments, the infusion device may include a force sensor which detects user input force and the electromechanical actuation member 850 may assist the user, allowing use of the device with decreased force. In some embodiments, the actuation member 850 may control substantially all motion and force provided to the syringe. In some embodiments, the trigger portion 37 of the lever 52 may be embodied as a button as illustrated in FIG. 11. The electromechanical actuation member 850 may be anchored to the housing by housing attachment point 851, and may be coupled to the lever 52 by lever attachment point 852. Either or both attachment points 851/852 may allow pivoting about the attachment point 851/852.

The electromechanical actuation member 850 may also comprise solenoid which may be actuated as determined by a processor 158". The solenoid may retract with force, to inhibit the user from being able to impart additional force to the trigger 37 and plunger 853 until the force is reduced below the not-to-exceed threshold. Locking devices may be released by the user pressing a release button, which may electronically signal the processer 158". In some embodiments, the processor 158" may release a lock device after a pre-determined amount of time has elapsed.

One of ordinary skill in the art will recognized that other devices and configurations of motors may be used to actuate the lever 52 without deviating from the present invention.

Figure 47A:
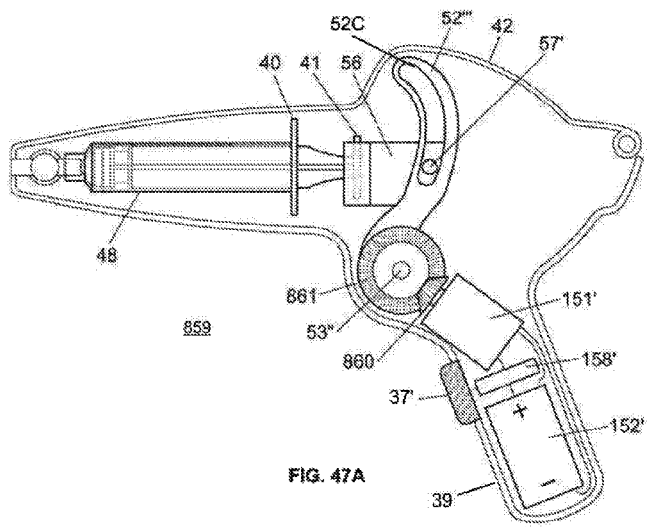
FIG. 47A is a side view of an embodiment of a handheld infusion device incorporating a motor, according to embodiments of the invention.
Figure 47B:
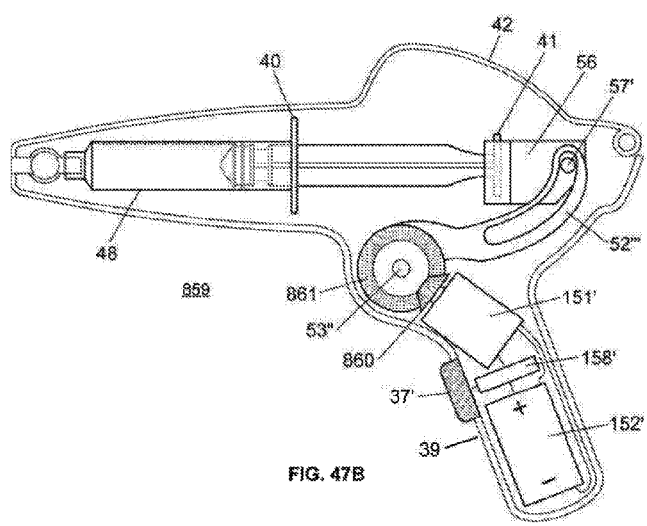
FIG. 47B is a side view of the infusion device of FIG. 47A in a retracted position, according to embodiments of the invention.

FIG. 47A is a side view of an embodiment of a handheld infusion device incorporating a motor 151', according to embodiments of the invention. FIG. 47A depicts a rotational motor 151' which has a bevel gear 860 on the end of a shaft. FIG. 47A illustrates the syringe 48 with the plunger 41 fully advanced. FIG. 47B is a side view of the infusion device of FIG. 47A in a retracted position, according to embodiments of the invention. FIG. 47B illustrates the plunger 41 of the syringe 48 fully retracted by the rotational motor 151'. As described herein a pin 57' may travel along a cam surface 52C within the lever 52''' to advance the shuttle 56 as the lever 52''' rotates. A mating bevel gear 861 may be integrated into the lever 52''' of the infusion device and centered around the pivot point 53". The motor 151' may be a stepper or other motor and/or may use a processor 158' in order to automatically advance and retract the shuttle 56 and plunger 41 to the desired point. A battery 152' may provide electrical power to the motor 151'. A trigger 37' can be an electronic control button or switch. The control button 37' may allow the user to control the flow of fluid through the operation of the motor 151'. Additional user inputs may be present to provide additional control inputs, such as pressure and/or volume targets and/or limits.

Figure 48A:
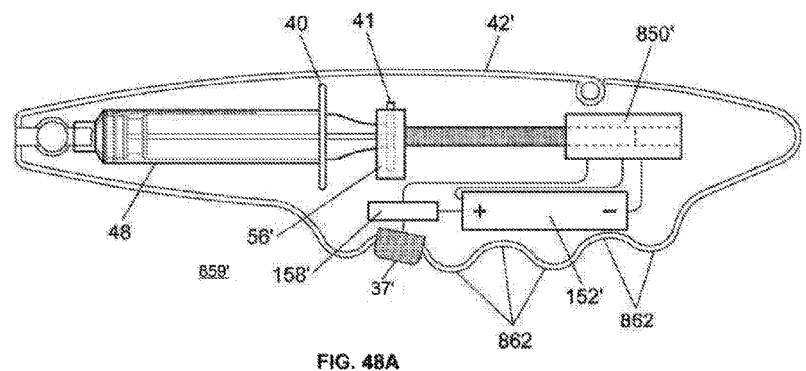
FIG. 48A is a side view of an embodiment of a handheld infusion device incorporating a linear actuator, according to embodiments of the invention.
Figure 48B:
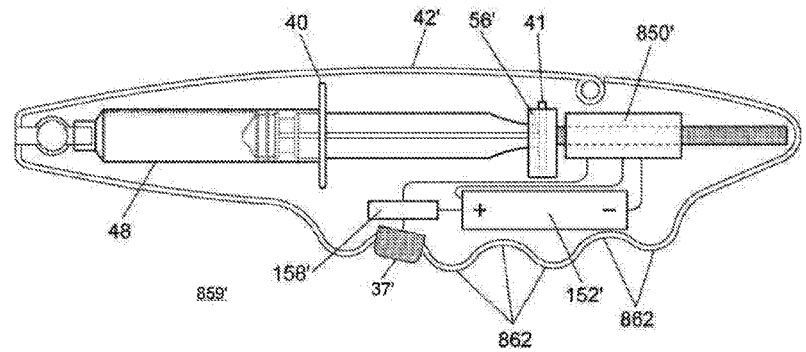
FIG. 48B is a side view of the infusion device of FIG. 48A in a retracted position, according to embodiments of the invention.

FIG. 48A is a side view of an embodiment of a handheld infusion device 859' incorporating a linear actuator 850', according to embodiments of the invention. FIG. 48A depicts the linear actuator 850' which is connected axially to a shuttle 56'. FIG. 48A shows the syringe 48 with the plunger 41 fully advanced. FIG. 48B is a side view of the infusion device 859' of FIG. 48A in a retracted position, according to embodiments of the invention. FIG. 48B shows the syringe 48 with the plunger 41 fully retracted. The linear actuator 850' may be controlled by a processor 158' in order to advance and retract the shuttle 56' and plunger 41 to the desired point. This embodiment is shown with an in-line handle, and may have indentations 862 for the user's fingers to rest during actuation of the control button 37'. A battery 152' may provide electrical power to the system. A trigger 37' can be an electronic control button or switch. The control button 37' may allow the user to control the flow of fluid through the operation of the linear actuator 850'. Additional user inputs may be present to provide additional control inputs, such as pressure and/or volume targets and/or limits. In some embodiments, the canopy 42' may not have a protrusion, as illustrated in this configuration.

FIGS. 48A and 48B show generally how the infusion device 859 of FIGS. 47A and 47B can be implemented in an infusion device 859' with an inline configuration. Similarly, while certain embodiments herein are illustrated with a pistol grip configuration, these embodiments may be configured to have an in-line handle or "pen-like" body with a trigger/lever.

As also illustrated herein, embodiments of the infusion device may be automated or manual, and each may be configured in the alternative. In some embodiments, the trigger may be a manual trigger such as, for example, trigger 37 illustrated in FIG. 22. In some embodiments, the trigger may be an automatic trigger, such as, for example, trigger 37' in FIG. 47A.

While the embodiments presented herein are well suited for use with IO infusion, they may be used in a similar manner to infuse fluids through an intravenous access point as well. By using universal connectors such as male/female luer connection, a wide variety of devices may be connected to the tubing. These devices may also work well with narrow gauge IV needles, which can sometimes cause existing transfusion pumps to function poorly.

Figure 49:
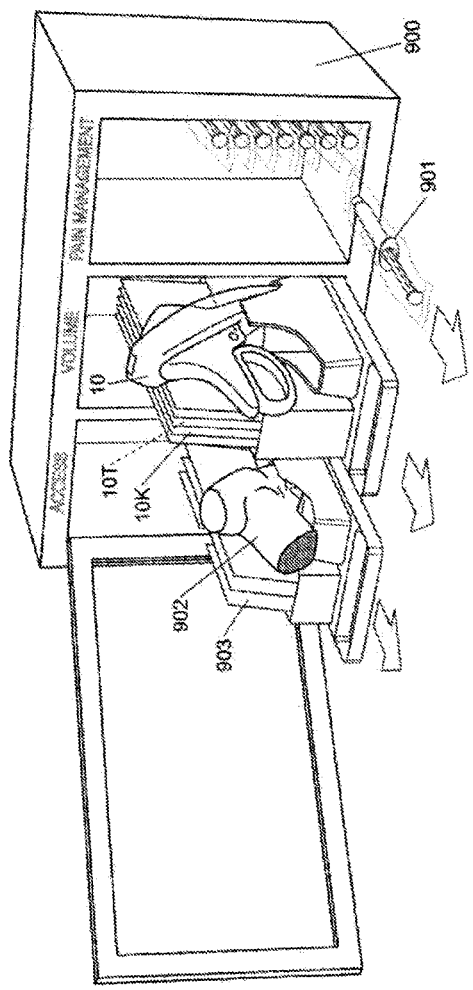
FIG. 49 is an isometric view of a container incorporating an infusion device, pain medication and an interosseous access system according to embodiments of the invention.

FIG. 49 is an isometric view of a container 900 incorporating an infusion device pain medication 901 and an interosseous access system 902/903 according to embodiments of the invention. The container 900 may contain an interosseous access system, a volume delivery system, and pain management. The interosseous (IO) access system may include a sterile IO needle 903 and a delivery system 902. Some examples of sterile IO needles 901 and delivery systems 902 include the EZ-IO access system from Teleflex of Morrisville, NC, FAST1 from Pyng Medical of British Columbia, Canada, Jamshidi Intraosseous Needles from Carefusion of Waukegan, IL, and Bone Injection Gun (B.I.G.) from Persys Medical of Houston, TX. The volume delivery system may consist of an infusion device 10, and a basic tubing set 10S, which may be included as part of a sterile tubing kit 10K. The pain management system may contain pre-filled syringes 901 of local anesthetic, such as lidocaine. In some embodiments, the pain management system may also include pre-filled syringes 901 of local anesthetic and prefilled syringes 911 of buffering agent, such as sodium bicarbonate. The container 900 may have a door which allows easy access for users to obtain any of the three elements, as needed, in an emergency. In some embodiments, the container 900 may be configured to be placed on a counter. In some embodiments, the container 900 may be configured to be mounted on a wall. In other embodiments, the container 900 may be configured to be placed in a drawer, mounted to a trolley, hospital cart or other medical device, or under a bed, though the present invention is not limited thereto.

Figure 50:
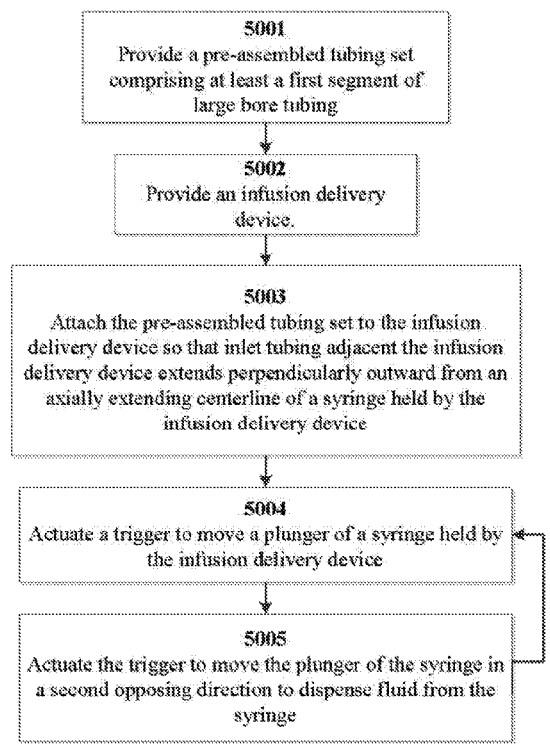
FIG. 50 illustrates exemplary operations for infusing fluid to a subject according to embodiments of the invention.

FIG. 50 illustrates exemplary operations for infusing fluid to a subject according to embodiments of the invention The method of infusing fluid to a subject may include providing a pre-assembled tubing set comprising at least a first segment of large bore tubing with a length between 3-12 feet with one end portion comprising a spike (block 5001), providing an infusion delivery device (block 5002), attaching the pre-assembled tubing set to the infusion delivery device so that inlet tubing adjacent the infusion delivery device extends perpendicularly outward from an axially extending centerline of a syringe held by the infusion delivery device so that the inlet tubing adjacent the infusion delivery device is parallel to a flange of the syringe to place volume indicia of the syringe facing upward (block 5003). Further, the method may include repetitively, serially actuating a trigger to move a plunger of a syringe held by the infusion delivery device in a first direction to intake fluid into a syringe (block 5004), and then actuating the trigger to move the plunger of the syringe in a second opposing direction to dispense fluid from the syringe (block 5005).

In some embodiments, the actuating steps may be carried out to intake and dispense at least once to prime a fluid flow path extending between the large bore tubing and the syringe, then infusing the fluid from the syringe to a subject based on the actuating steps from a fluid source through the syringe into small bore tubing attached to the infusion delivery device to deliver the infusion fluid to a subject.

In some embodiments, the pre-assembled tubing set (e.g., tubing set 10S of FIG. 19A) may include the first segment of large bore tubing attached to a pouch of saline and a second segment of large bore tubing attached to a pouch of blood or blood product or contrast agent, the first and second segments merging into a third segment of large bore tubing that is attached to an inlet tube extending out a sidewall of a housing of the infusion delivery device.

In some embodiments, the method may further include providing a length of small bore tubing with a Y connection attached to an exit port of a dual check valve held by the infusion delivery device, and injecting fluids or other medications into a port of the small bore tubing prior to infusing the fluid to the subject.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

The invention claimed is:

1. A system, comprising:
    a tubing set including:
        inlet tubing couplable to a source of fluid;
        a valve having a valve inlet coupled to the inlet tubing and a valve outlet;
        a syringe coupled to the inlet tubing via the valve, the syringe having a syringe body and a plunger translatable relative to the syringe body to draw fluid into the syringe body and expel fluid from the syringe body, and
        outlet tubing coupled to the valve outlet, the valve configured to allow fluid to be drawn from the source of fluid via the inlet tubing into the syringe body and to be expelled from the syringe body and through the outlet tubing, the valve configured to prevent fluid from being drawn from the outlet tubing into the syringe body and to prevent fluid expelled from the syringe body from flowing through the inlet tubing;

a drive assembly including a housing defining an interior and a drive mechanism at least partially disposed within the interior, the drive assembly configured to releasably receive the tubing set such that the tubing set is disposed outside of the housing and the drive mechanism is operably coupled to the plunger to reciprocally translate the plunger relative to the syringe body, the drive mechanism including a pinion configured to engage with a rack fixedly coupled to the plunger; and an enclosure configured to be releasably coupled to an outer surface of the housing such that the syringe body and the valve are disposed between the outer surface of the housing and the enclosure, the enclosure defining an opening configured to receive a portion of at least one of the valve inlet and the inlet tubing such that the portion of at least one of the valve inlet and the inlet tubing is retained between the enclosure and the outer surface of the housing.

2. The system of claim 1, wherein the outer surface defines a first receiving aperture configured to retain a portion of the valve and a second receiving aperture configured to retain a portion of the syringe body, the valve and the syringe body configured to be simultaneously received in the first receiving aperture and the second receiving aperture, respectively, via a lateral displacement of the valve and the syringe body relative to the outer surface, the plunger configured to be operatively coupled to the drive mechanism via the lateral displacement.

3. The system of claim 1, wherein the enclosure is configured to be magnetically coupled to the housing.

4. The system of claim 1, wherein the enclosure includes a lid rotationally coupled to the housing via a hinge.

5. The system of claim 1, wherein the drive assembly includes a motor configured to drive the drive mechanism.

6. The system of claim 1, wherein the drive mechanism includes a shuttle configured to engage with the plunger.

7. The system of claim 1, wherein the drive assembly includes an actuation lever rotationally coupled to the housing and the drive mechanism such that rotation of the actuation lever causes translation of the plunger.

8. The system of claim 7, wherein the actuation lever defines a cam path and the drive mechanism includes a shuttle configured to engage with the plunger, the shuttle including a pin disposed within the cam path and configured to travel within the cam path relative to an end of the actuation lever.

9. The system of claim 7, wherein the drive assembly includes a spring arranged to apply a force to the actuation lever to urge a trigger of the actuation lever from a retracted position to an extended position, the force being greater when the trigger is in the retracted position than when the trigger is in the extended position.

10. The system of claim 1, wherein a central axis of the valve inlet and a central axis of the valve outlet are disposed in a plane disposed parallel to the outer surface of the housing of the drive assembly.

11. The system of claim 1, wherein the drive mechanism is configured such that rotation of the pinion causes translation of the rack and the plunger relative to the syringe body, the rack and the plunger configured to translate along parallel axes.

12. A system, comprising:
a tubing set including:
inlet tubing couplable to a source of fluid,
a valve coupled to the inlet tubing,
a syringe coupled to the inlet tubing via the valve, the syringe having a syringe body and a plunger translatable relative to the syringe body to draw fluid into the syringe body and expel fluid from the syringe body, and
outlet tubing coupled to the valve, the valve configured to allow fluid to be drawn from the source of fluid via the inlet tubing into the syringe body and to be expelled from the syringe body and through the outlet tubing, the valve configured to prevent fluid from being drawn from the outlet tubing into the syringe body and to prevent fluid expelled from the syringe body from flowing through the inlet tubing;

a rack; and a drive assembly including a motor and a drive mechanism, the drive assembly configured to releasably receive the tubing set such that the drive mechanism is coupled to the plunger via the rack, the drive mechanism including a pinion configured to be coupled to the rack, the motor configured to drive rotation of the drive mechanism to reciprocally translate the rack, reciprocal translation of the rack causing the plunger to reciprocally translate relative to the syringe body and along an axis parallel to a central axis of the rack.

13. The system of claim 12, wherein the rack is coupled to the plunger via a connecting portion fixed to and extending perpendicularly from an end of the rack.

14. The system of claim 12, wherein the drive assembly includes a housing, and further comprising an enclosure configured to be releasably coupled to an outer surface of the housing of the drive assembly such that the syringe body and the valve are disposed between the outer surface of the housing and the enclosure.

15. The system of claim 12, wherein the drive assembly includes a housing defining an interior, the motor at least partially disposed within the interior.

16. The system of claim 15, wherein the drive mechanism is at least partially disposed within the interior of the housing.

17. The system of claim 12, wherein the rack is fixedly coupled to the plunger.

18. The system of claim 12, wherein the drive assembly includes a housing having an outer surface, the drive assembly configured to releasably receive the tubing set such that the syringe body and the valve are retained in a fixed position relative to the outer surface of the housing during reciprocal translation of the plunger.

19. A system, comprising:
a tubing set including:
inlet tubing couplable to a source of fluid;
a valve having a valve inlet coupled to the inlet tubing and a valve outlet;
a syringe coupled to the inlet tubing via the valve, the syringe having a syringe body and a plunger translatable relative to the syringe body to draw fluid into the syringe body and expel fluid from the syringe body, and
outlet tubing coupled to the valve outlet, the valve configured to allow fluid to be drawn from the source of fluid via the inlet tubing into the syringe body and to be expelled from the syringe body and through the outlet tubing, the valve configured to prevent fluid from being drawn from the outlet tubing into the syringe body and to prevent fluid expelled from the syringe body from flowing through the inlet tubing;

a drive assembly including a housing defining an interior and a drive mechanism at least partially disposed within the interior, the drive assembly configured to releasably receive the tubing set such that the tubing set is disposed outside of the housing and the drive mechanism is operably coupled to the plunger to reciprocally translate the plunger relative to the syringe body; and an enclosure configured to be releasably coupled to an outer surface of the housing such that the syringe body and the valve are disposed between the outer surface of the housing and the enclosure, the enclosure defining an opening configured to receive a portion of at least one of the valve inlet and the inlet tubing such that the portion of at least one of the valve inlet and the inlet tubing is retained between the enclosure and the outer surface of the housing, the outer surface defining a first receiving aperture configured to retain a portion of the valve and a second receiving aperture configured to retain a portion of the syringe body, the valve and the syringe body configured to be simultaneously received in the first receiving aperture and the second receiving aperture, respectively, via a lateral displacement of the valve and the syringe body relative to the outer surface, the plunger configured to be operatively coupled to the drive mechanism via the lateral displacement.

20. A system, comprising:
a tubing set including:
   inlet tubing couplable to a source of fluid,
   a valve coupled to the inlet tubing,
   a syringe coupled to the inlet tubing via the valve, the syringe having a syringe body and a plunger translatable relative to the syringe body to draw fluid into the syringe body and expel fluid from the syringe body, and
   outlet tubing coupled to the valve, the valve configured to allow fluid to be drawn from the source of fluid via the inlet tubing into the syringe body and to be expelled from the syringe body and through the outlet tubing, the valve configured to prevent fluid from being drawn from the outlet tubing into the syringe body and to prevent fluid expelled from the syringe body from flowing through the inlet tubing;
a rack coupled to the plunger via a connecting portion fixed to and extending perpendicularly from an end of the rack; and
a drive assembly including a motor and a drive mechanism, the drive assembly configured to releasably receive the tubing set such that the drive mechanism is coupled to the plunger via the rack, the motor configured to drive rotation of the drive mechanism to reciprocally translate the rack, reciprocal translation of the rack causing the plunger to reciprocally translate relative to the syringe body and along an axis parallel to a central axis of the rack.

* * * * *